United States Patent
Komers et al.

(10) Patent No.: US 11,207,299 B2
(45) Date of Patent: Dec. 28, 2021

(54) BIPHENYL SULFONAMIDE COMPOUNDS FOR THE TREATMENT OF TYPE IV COLLAGEN DISEASES

(71) Applicant: Travere Therapeutics, Inc., San Diego, CA (US)

(72) Inventors: Radko Komers, San Diego, CA (US); Celia Jenkinson, San Diego, CA (US)

(73) Assignee: Travere Therapeutics, Inc., San Diego, CA (US)

(*) Notice: Subject to any disclaimer, the term of this patent is extended or adjusted under 35 U.S.C. 154(b) by 30 days.

(21) Appl. No.: 16/592,633

(22) Filed: Oct. 3, 2019

(65) Prior Publication Data

US 2020/0147050 A1    May 14, 2020

Related U.S. Application Data

(60) Provisional application No. 62/741,270, filed on Oct. 4, 2018, provisional application No. 62/853,904, filed
(Continued)

(51) Int. Cl.
*A61K 31/422* (2006.01)
*A61P 27/16* (2006.01)
*A61K 9/00* (2006.01)

(52) U.S. Cl.
CPC .......... *A61K 31/422* (2013.01); *A61K 9/0053* (2013.01); *A61P 27/16* (2018.01)

(58) Field of Classification Search
CPC ...... A61K 31/422; A61K 9/0053; A61K 9/00; A61K 45/06; A61P 27/16; A61P 31/12
(Continued)

(56) References Cited

U.S. PATENT DOCUMENTS 6,638,937 B2   10/2003   Murugesan et al.
6,835,741 B2   12/2004   Murugesan et al.
(Continued)

FOREIGN PATENT DOCUMENTS

WO   00/01389       1/2000
WO   01/44239 A2    6/2001
(Continued)

OTHER PUBLICATIONS

Adler et al., "Glomerular type IV collagen in patients with diabetic nephropathy with and without additional glomerular disease," *Kidney International* 57:2084-2092, 2000.
(Continued)

*Primary Examiner* — Taylor V Oh
(74) *Attorney, Agent, or Firm* — Seed Intellectual Property Law Group LLP

(57) ABSTRACT

Methods of treating Alport syndrome and other diseases associated with a type IV collagen deficiency, and preventing hearing loss associated the same, are provided, comprising administering a compound having structure (I),
(Continued)

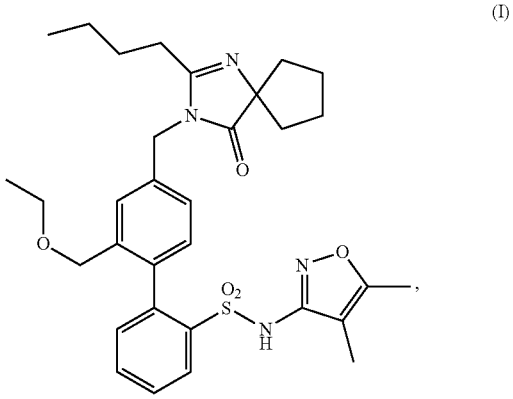

(I)

or a pharmaceutically acceptable salt thereof, or administering a pharmaceutical composition comprising the compound of structure (I) or pharmaceutically acceptable salt thereof.

22 Claims, 30 Drawing Sheets

Related U.S. Application Data on May 29, 2019, provisional application No. 62/894,559, filed on Aug. 30, 2019.

(58) Field of Classification Search
USPC ......................................................... 514/380
See application file for complete search history.

(56) References Cited

U.S. PATENT DOCUMENTS

| | | | |
|---|---|---|---|
| 9,662,312 | B2 | 5/2017 | Zhang et al. |
| 9,993,461 | B2 | 6/2018 | Zhang et al. |
| 10,864,197 | B2 * | 12/2020 | Komers ................. A61P 43/00 |
| 2002/0143024 | A1 | 10/2002 | Murugesan et al. |
| 2004/0106833 | A1 | 6/2004 | San et al. |
| 2015/0164865 | A1 | 6/2015 | Zhang et al. |
| 2015/0175695 | A1 | 6/2015 | Cosgrove |
| 2018/0344705 | A1 | 12/2018 | Zhang et al. |
| 2019/0262317 | A1 | 8/2019 | Komers et al. |

FOREIGN PATENT DOCUMENTS

| | | |
|---|---|---|
| WO | 2010/135350 A2 | 11/2010 |
| WO | WO2018/071784 A1 * | 4/2018 |
| WO | 2020/132594 | 6/2020 |

OTHER PUBLICATIONS

Barton, "Therapeutic potential of endothelin receptor antagonists for chronic proteinuric renal disease in humans," *Biochimica et Biophysica Acta* 1802: 1203-1213, 2010.

Barton et al., "Endothelin and the podocyte," *Clin Kidney J.* 5: 17-27, 2012.

Cameron, "Focal segmental glomerulosclerosis in adults," *Nephrol. Dial. Transplant.* 18 [Suppl 6]: vi45-vi51, 2003.

D'Agati et al., "Focal Segmental Glomerulosclerosis," *The New England Journal of Medicine* 365(25): 2398-2411, Dec. 22, 2011.

Delimont et al., "Laminin α2-Mediated Focal Adhesion Kinase Activation Triggers Alport Glomerular Pathogenesis," *PLOS One, Podocyte FAK Activation in Alport Syndrome* 9(6): e99083, 2014 (14 pages).

Dhaun et al., "Blood Pressure-Independent Reduction in Proteinuria and Arterial Stiffness After Acute Endothelin-A Receptor Antagonism in Chronic Kidney Disease," *Hypertension* 54: 113-119, 2009.

Dhaun et al., "Selective Endothelin-A Receptor Antagonism Reduces Proteinuria, Blood Pressure, and Arterial Stiffness in Chronic Proteinuric Kidney Disease," *Hypertension*: 712-719, Apr. 2011.

Doi, "Diagnosis and Treatment of Diabetic Nephropathy—The Current Status of Management and Its Problem," *The Journal of the Japanese Society of Internal Medicine* 96(3):453-458, 2007. (w/English Abstract).

Duet Study "The effects of FSGS are more than just physical," Internet http://www.fsgsduetstudy.com/#page 1, Retrieved Oct. 4, 2016 (4 pages).

Dufek et al., "Endothelin A receptor activation on mesangial cells initiates Alport glomerular disease," *Kidney International* 90: 300-310, 2016.

Fervenza et al., "Idiopathic Membranous Nephropathy: Diagnosis and Treatment," *Clin. J. Am. Soc. Nephrol.* 3: 905-919, 2008.

Gipson et al., "Clinical Trial of Focal Segmental Glomerulosclerosis in Children and Young Adults," *Kidney International* 80: 868-878, 2011.

González-Albarrán et al., "Role of Systolic Blood Pressure on the Progression of Kidney Damage in an Experimental Model of Type 2 Diabetes Mellitus, Obesity, and Hypertension (Zucker Rats)," AJH, 2003, vol. 16, No. 11, p. 979-985.

Gross et al., "Preemptive ramipril therapy delays renal failure and reduces renal fibrosis in COL4 A3-knockout mice with Alport syndrome1," *Kidney International* 63:43 8-446, 2003.

Ikeda et al., "Next generation ARBs: Going Beyond Modulation of the Renin-Angiotensin System," *Int. Heart J.* 585-586, 2015.

Inker et al., "Early Change in Urine Protein as a Surrogate End Point in Studies of IgA Nephropathy: An Individual-Patient Meta-analysis," *Am. J. Kidney Dis.* 68(3): 392-401, 2016.

Inker et al., "Early Change in Urine Protein as a Surrogate End Point in Studies of IgA Nephropathy: An Individual-Patient Meta-analysis," *Am. J. Kidney Dis.* 68(3): 392-401, 2016, Supplemental Pages (12 pages).

Jaipaul, "Diabetic Nephropathy," Merck Manual Professional Version, pp. 1-5, 2018.

Kangovi et al., "Renin-Angiotensin-aldosterone system inhibitors in pediatric focal segmental glomerulosclerosis," *Pediatr Nephrol*, 2011 (7 pages).

Kiffel et al. "Focal Segmental Glomerulosclerosis and Chronic Kidney Disease in Pediatric Patients," *Adv. Chronic Kidney Dis.* 18(5):332-338, 2011.

Kitiyakara et al., "Twenty-One-Year Trend in ESRD Due to Focal Segmental Glomerulosclerosis in the United States," *American Journal of Kidney Diseases* vol. 44, No. 5 (November): 815-825, 2004.

Kohan et al., "Addition of Atrasentan to Renin-Angiotensin System Blockade Reduces Albuminuria in Diabetic Nephropathy," *J. Am. Soc. Nephrol.* 22(4): 763-772, 2011.

Kohan et al., "Endothelin and Endothelin Antagonists in Chronic Kidney Disease," *Kidney International* 86:896-904, 2014.

Komers et al.: "Antihypertensive Effects of Sparsentan, a Dual Angiotensin II and Endothelin Type A Receptor Antagonist," [Abstract], *J Am Soc Nephrol* 27, 2016: 788A.

Komers et al., "Dual inhibition of renin-angiotensin-aldosterone system and endothelin-1 in treatment of chronic kidney disease," *Am. J. Physiol. Regul. Integr. Comp. Physiol.* 310:R877-R884, 2016.

Komers et al., "Efficacy and Safety of Sparsentan Compared With Irbesartan in Patients With Primary Focal Segmental Glomerulosclerosis: Randomized, Controlled Trial Design (DUET)," *Kidney International Reports* 2:654-664, 2017.

Kowala et al., "Novel Dual Action $AT_1$ and $ET_A$ Receptor Antagonists Reduce Blood Pressure in Experimental Hypertension," *The Journal of Pharmacology and Experimental Therapeutics* 309(1):275-284, 2004.

Leach et al.: "Renal Pharmacology and Preclinical Attributes of Sparsentan, a Dually Active Endothelin A and Angiotensin 1 Receptor Antagonist," [Abstract], *J Am Soc Nephrol* 27, 2016: 132A.

(56) References Cited

OTHER PUBLICATIONS

Mann et al., "Avosentan for Overt Diabetic Nephropathy," *J. Am. Soc. Nephrol.* 21: 527-535, 2010.
Meehan et al., "Endothelin-1 mediated induction of extracellular matrix genes in strial marginal cells underlies strial pathology in Alport mice," *Hearing Research* 347:100-108, 2016.
Murugesan et al., "Dual Angiotensin II and Endothelin A Receptor Antagonists: Synthesis of 2'-Substituted N-3-Isoxazolyl Biphenylsulfonamides with Improved Potency and Pharmacokinetics," *J Med. Chem.* 48: 171-179, 2005.
Neutel et al., "Abstract 4420: Results of A Double Blind Placebo Controlled Study to Evaluate the Efficacy and Safety of PS433540 in Human Subjects with Hypertension," *Circulation* 118:S_886, 2008, 1 page.
Neutel et al., "Results of a double blind, placebo controlled study to evaluating PS433540, a novel dual acting receptor antagonist in stage I and II hypertenives," *J. Am. Soc. Nephrol.* 19 2008, 2 pages.
New Drug Approvals "Sparsentan (PS433540,RE-021)," retrieved from https://newdrugapprovals.org/2015/10/12/sparsentan-ps433540-re-021/on Dec. 17, 2019 (10 pages).
O'Riordan, "Dual-acting receptor antagonist reduces systolic blood pressure: No safety signals raised in phase 2a trial," *Heartwire*, May 19, 2008, retrieved from https://www.medscape.com/viewarticle/574699, on Aug. 28, 2019, 2 pages.
Pan-Zhou et al.: "Pharmacokinetics of Sparsentan in Healthy Subjects: In Vitro Metabolism and Effects of Food, Gender, Age, and Multiple-Dose Escalation," [Abstract]. *J Am Soc Nephrol* 27, 2016: 746A.
Pharmacopeia, "Investor Presentation PS433540 Phase 2a Study Results," May 16, 2008, retrieved from http://www.sec.gov/Archives/edgar/data/1273013/000110465908033876/a08-142532ex99d2.htm, 12 pages.
Praga et al., "Treatment of IgA Nephropathy with ACE Inhibitors: A Randomized and Controlled Trial," *J. Am. Soc. Nephrol.* 14: 1578-1583, 2003.
Reich et al., "Remission of Proteinuria Improves Prognosis in IgA Nephropathy," *J. Am. Soc. Nevhrol.* 18: 3177-3183, 2007.
Retrophin, Inc., "Randomized, Double-Blind, Safety and Efficacy Study of RE-021 (Sparsentan) in Focal Segmental Glomerulosclerosis (DUET)," ClinicalTrials.gov, ClinicalTrials.gov Identifier: NCT01613118, 2012 (3 pages).
Retrophin, Inc., "Retrophin Announces Positive Top-Line Results from Phase 2 DUET Study of Sparsentan in Patients with Focal Segmental Glomerulosclerosis," Press Release, Sep. 7, 2016, 3 pages.
Ritz et al., "Endothelin Antagonist as Add-on Treatment for Proteinuria in Diabetic Nephropathy: Is There Light at the End of the Tunnel?" *J Am. Soc. Nephrol.* 22: 593-595, 2011.
Schieppati et al., "Prognosis of Untreated patients with Idiopathic Membranous Nephropathy," *The New England Journal of Medicine* 329(2):85-89, 1993.
Shacter et al., "Chronic Inflammation and Cancer," *Cancer Network* 16(2): 1-8, 2002.
Thompson Pharma Integrity, Entry 307300 for Drug Name "PS433540," Retrieved Jun. 8, 2013, 2 pages.
Tobe et al., "Endothelin Receptor Antagonists: New Hope for Renal Protection?" *Curr. Hypertens Rep.* 17: 57, 2015 (7 pages).
Trachtman et al.: "Efficacy and Safety of Sparsentan, a Dual Angiotensin II (Ang II) and Endothelin (ET) Type A Receptor Antagonist, in Patients with Focal Segmental Glomerulosclerosis (FSGS): A Phase 2 Trial (DUET)," [Abstract], *J Am Soc Nephrol* 27, 2016: 2B.
Trachtman, "Investigational drugs in development for focal segmental glomerulosclerosis," *Expert Opinion on Investigational Drugs* 26(8):945-952, 2017.
Troost et al.: "A Clinical Outcome Assessment of Proteinuria in Patients with Focal Segmental Glomerulosclerosis," [Abstract], *J Am Soc Nephrol* 27, 2016: 62A.
van der Loop et al., "Autosomal dominant Alport syndrome caused by a COL4A3 splice site mutation," *Kidney International* 58:1870-1875, 2000.
Wenzel et al., "Avosentan Reduces Albumin Excretion in Diabetics with Macroalbuminuria," *J. Am. Soc. Nephrol.* 20: 655-664, 2009.
Yuzawa, "Pathophysiology, Diagnosis and Treatment of Primary Nephrotic Syndrome," *The Journal of the Japanese Society of Internal Medicine*, 2009, vol. 98, No. 5, p. 1016-1022, with English abstract.
Abbate et al., "How Does Proteinuria Cause Progressive Renal Damage," *J Am Soc Nephrol* 17:2974-2984, 2006.
Abbate et al., "Transforming Growth Factor-β1 Is Up-Regulated by Podocytes in Response to Excess Intraglomerular Passage of Proteins," *American Journal of Pathology* 161(6):2179-2193, 2002.
Arif et al., "Glomerular Filtration Barrier Assembly: An insight," *Postdoc J.* 1(4):33-45, 2013 (HHS Public Access Author manuscript, available in PMC Aug. 29, 2016) (14 pages).
Campbell et al., "Protecting Podocytes: A Key Target for Therapy of Focal Segmental Glomerulosclerosis," *Am J Nephrol* 47(suppl 1): 14-29, 2018, Published online May 31, 2018.
Cosgrove et al., "The Dual Endothelin/Angiotensin II Receptor (ETAR/ATIR) Antagonist Sparsentan Slows Renal Disease, Improves Lifespan, and Attenuates Hearing Loss in Alport Mice: Comparison with Losartan and Atrasentan," Presented at the German Society of Nephrology 12th Annual Virtual Congress 2020, Oct. 1-4, 2020 (1 Page).
Gipson et al., "Clinical trials treating focal segmental glomerulosclerosis should measure patient quality of life," *Kidney International* 79:678-685, 2011.
Jefferson et al., "The Pathogenesis of Focal Segmental Glomerulosclerosis," *Adv Chronic Kidney Dis.* 21(5):408-416, 2014 (NIH Public Access Author Manuscript, available in PMC Sep. 1, 2015) (20 pages).
Kashtan et al., "Alport syndrome: a unified classification of genetic disorders of collagen IV α345: a position paper of the Alport Syndrome Classification Working Group," *Kidney International* 93:1045-1051, 2018.
Korbet, "Treatment of Primary FSGS in Adults," *J Am Soc Nephrol* 23:1769-1776, 2012.
Miner, "Glomerular basement membrane composition and the filtration barrier," *Pediatr Nephrol* 26(9):1413-1417, 2011 (NIH Public Access Author Manuscript, available in PMC Sep. 1, 2012) (7 pages).
Miner et al., "The 2014 International Workshop on Alport Syndrome," *Kidney International* 56:679-684, 2014.
Reitsma et al., "The endothelial glycocalyx: composition, functions and visualization," *Pflugers Arch—Eur J Pysiol* 454:345-359, 2007.
Rosenberg et al., "Focal Segmental Glucomerulosclerosis," *Clin J Am Soc Nephrol* 12:502-517, 2017.
Schell et al., "The Evolving Complexity of the Podocyte Cytoskeleton," *J Am Soc Nephrol* 28:3166-3174, 2017.
Siragy et al., "Role of the Intrarenal Renin-Angiotensin-Aldosterone System in Chronic Kidney Disease," *Am J Neprol* 37:541-550, 2010, Published online May 18, 2010.
Trachtman et al., "DUET: A Phase 2 Study Evaluating the Efficacy and Safety of Sparsentan in Patients with FSGS," *J Am Soc Nephrol* 29: 2745-2754, 2018.
U.S. Appl. No. 17/100,095, filed Nov. 20, 2020.
U.S. Appl. No. 17/096,637, filed Nov. 12, 2020
Savige et al., "Expert Guidelines for the Management of Alport Syndrome and Thin Basement Membrane Nephropathy," *J Am Soc Neprhol* 24:364-375, 2013.

* cited by examiner

BIPHENYL SULFONAMIDE COMPOUNDS FOR THE TREATMENT OF TYPE IV COLLAGEN DISEASES

BACKGROUND

The present disclosure relates to the use of biphenyl sulfonamide compounds that are dual angiotensin and endothelin receptor antagonists in the treatment of diseases associated with type IV collagen deficiency or abnormalities, such as Alport syndrome.

Angiotensin II (AngII) and endothelin-I (ET-1) are two of the most potent endogenous vasoactive peptides currently known and are believed to play a role in controlling both vascular tone and pathological tissue remodeling associated with a variety of diseases including diabetic nephropathy, heart failure, and chronic or persistently elevated blood pressure. Angiotensin receptor blockers (ARBs), which block the activity of AngII, have been used as a treatment for diabetic nephropathy, heart failure, chronic, or persistently elevated blood pressure. There is also a growing body of data that demonstrates the potential therapeutic benefits of ET receptor antagonists (ERAs) in blocking ET-1 activity. Additionally, AngII and ET-1 are believed to work together in blood pressure control and pathological tissue remodeling. For example, ARBs not only block the action of AngII at its receptor, but also limit the production of ET-1. Similarly, ERAs block ET-1 activity and inhibit the production of AngII. Consequently, simultaneously blocking AngII and ET-1 activities may offer better efficacy than blocking either substance alone. In rat models of human chronic or persistently elevated blood pressure, the combination of an ARB and an ERA has been shown to result in a synergistic effect. Furthermore, although ARBs are the standard of care for patients with diabetic nephropathy, improved efficacy with the co-administration of an ERA has been reported in Phase 2 clinical development.

Alport syndrome is a rare genetic disease associated with kidney involvement, hearing loss, and eye abnormalities. It is caused by mutations in the COL4A3, COL4A4, or COL4A5 genes, which are involved in the production of type IV collagen (van der Loop et al., Kidney Int 58:1870-1875, 2000). X-linked Alport syndrome contributes to about 80% of cases, with the remainder due to autosomal recessive and autosomal dominant mutations. Alport syndrome is typically characterized by progressive loss of kidney function. People with Alport syndrome often have hematuria (blood in the urine) and proteinuria (protein in the urine), conditions indicative of abnormal functioning of the kidneys. As the kidneys become more damaged, people with Alport syndrome frequently progress to end-stage renal disease (ESRD). In addition to kidney disease, Alport syndrome is associated with abnormalities of the inner ear and development of sensorineural hearing loss during late childhood or early adolescence. Alport syndrome is sometimes associated with misshapen lenses in the eyes (anterior lenticonus) and abnormal coloration of the retina, although these eye abnormalities typically do not lead to vision loss.

It is estimated that about 50% of males with X-linked Alport syndrome will require dialysis or kidney transplantation by early adulthood, and about 90% will develop ESRD before 40 years of age. Although ESRD is less common in female patients with X-linked Alport syndrome, as many as 12% of female patients also develop ESRD by age 40; this increases to 30% by age 60.

Blocking the effects of ET-1, Ang-II, or both, may offer therapeutic benefits for patients with diseases or disorders involving the kidneys, such as Alport syndrome. For example, strain-mediated induction of ET-1 in glomerular endothelial cells activates ET type A (ETA) receptors on mesangial cells, initiating invasion of glomerular capillaries by mesangial filopodia. The filopodia deposit matrix in the glomerular basement membrane (GBM) resulting in stimulation of NFκB activity in podocytes and expression of pro-inflammatory cytokines, culminating in glomerulosclerosis and interstitial fibrosis (Delimont et al., PLoS ONE 9(6):e99083, 2014). Both ETA receptor blockade with sitaxentan (Dufek et al., Kidney Int 90:300-310, 2016) and angiotensin-converting enzyme (ACE) inhibition with ramipril (Gross et al., Kidney Int 63:438-446, 2003) have been shown to ameliorate glomerulosclerosis and interstitial fibrosis in murine models of Alport syndrome. Additionally, the ETA antagonist sitaxentan has been shown to protect the basement membrane in the cochlea of the ear in Alport mice (Meehan et al., Hearing Research 341:100-198, 2016).

Currently there is no specific treatment for Alport syndrome and the standard of care is limited to angiotensin converting enzyme inhibitors (ACEi) or ARBs, which can slow down the progression of the disease but do not prevent ESRD and do not prevent the hearing loss that is frequently associated with the disease.

Mutations in type IV collagen genes are also associated with other diseases. For example, a missense mutation in the COL4A3 gene is associated with Type 1 diabetic kidney disease (Salem et al., JASN 30:2000-2016, 2019) and Type 2 diabetic ESRD (Guan et al., Hum. Genet. 135(11):1251-1262, 2016).

Thus, there remains a need for compositions and methods for treating Alport syndrome and other diseases associated with deficiencies or abnormalities in type IV collagen.

BRIEF SUMMARY

In some embodiments, the present disclosure is directed to methods of treating hearing loss in a subject having Alport syndrome, comprising administering a pharmaceutical composition comprising a compound having structure (I),

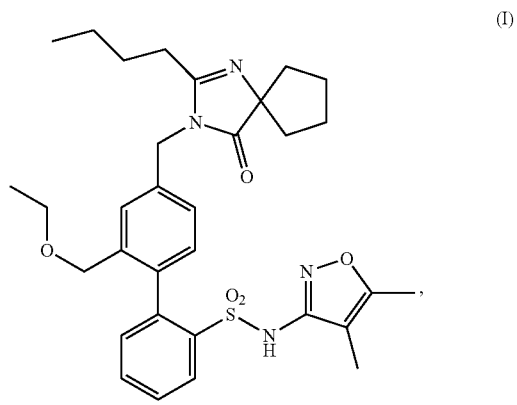 [SMILES: CCCCC1=NC2(CCCC2)C(=O)N1Cc1ccc(-c2ccccc2S(=O)(=O)Nc2noc(C)c2C)c(COCC)c1]

or a pharmaceutically acceptable salt thereof, to the subject.

In some embodiments, the present disclosure provides a method of treating hearing loss in a subject having a mutation in a COL4A3, COL4A4, or COL4A5 gene, comprising administering a pharmaceutical composition comprising a compound having structure (I), or a pharmaceutically acceptable salt thereof, to the subject.

In some embodiments, the present disclosure provides a method of treating Alport syndrome in a subject, comprising administering a pharmaceutical composition comprising a compound having structure (I), or a pharmaceutically acceptable salt thereof, to the subject.

In some embodiments, the present disclosure provides a method of treating hearing loss in a subject having diabetes, comprising administering a pharmaceutical composition comprising a compound having structure (I), or a pharmaceutically acceptable salt thereof, to the subject.

In some embodiments, the present disclosure provides a method of treating a collagen type IV deficiency in a subject, comprising administering a pharmaceutical composition comprising a compound having structure (I), or a pharmaceutically acceptable salt thereof, to the subject.

In some embodiments, the present disclosure provides pharmaceutical compositions for use in the above methods. In still further embodiments, the present disclosure provides for the use of the pharmaceutical compositions in the manufacture of a medicament for use in the above methods.

These and other aspects of the present invention will become apparent upon reference to the following detailed description.

DETAILED DESCRIPTION

Figure 1:
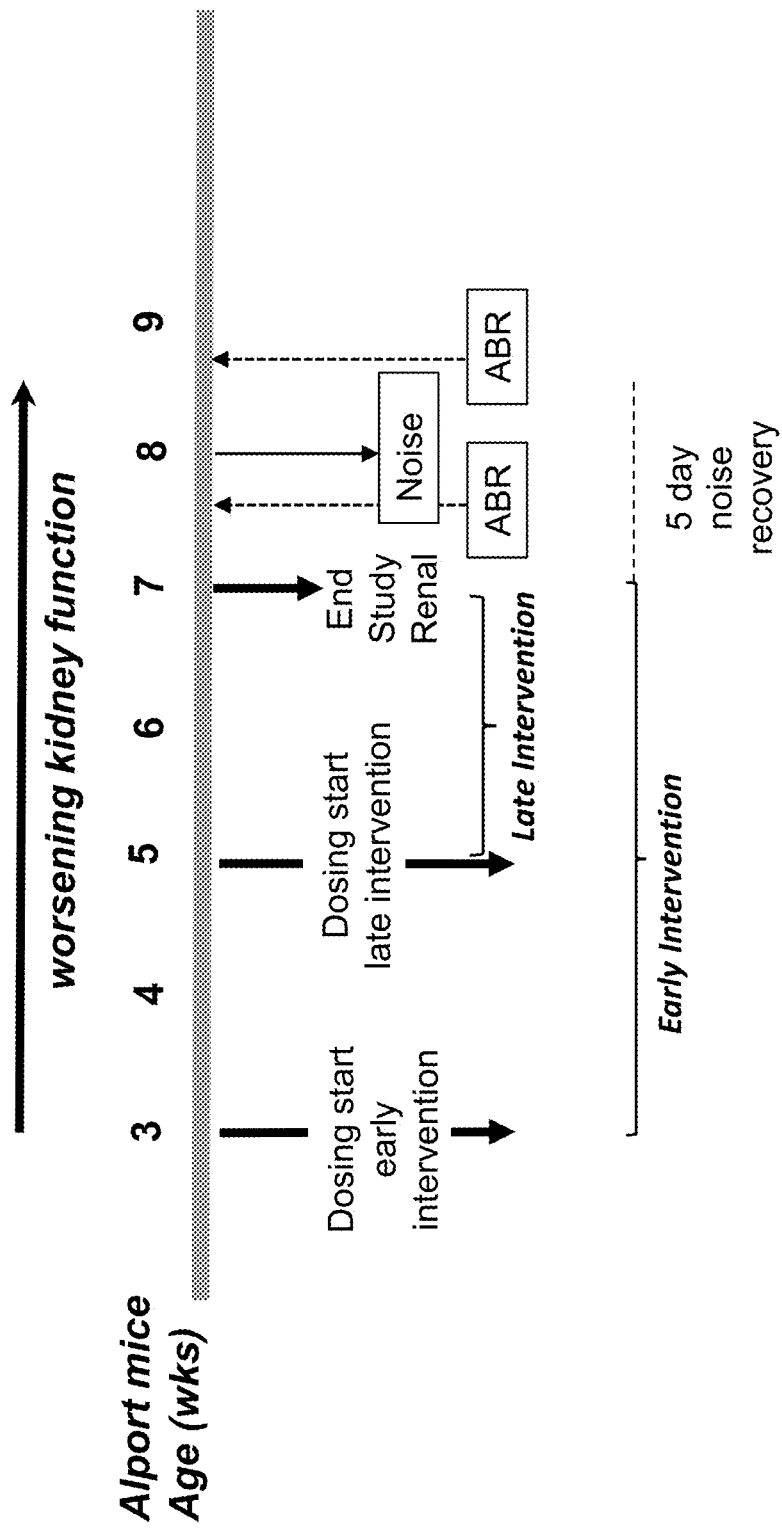
FIG. 1. Schematic of experimental studies with sparsentan in Alport mice. In the pilot study, Alport mice were treated once daily with sparsentan (60 or 200 mg/kg given orally; n=3-4/group) or vehicle (n=4) from 3-7 weeks of age. In the early intervention study, wild-type or Alport mice were treated once daily with sparsentan (120 mg/kg given orally; n=8/group) or losartan (20 mg/kg given orally from 3-4 weeks of age and 10 mg/kg given in drinking water from 4-7 weeks of age; n=7-8/group) or vehicle (n=8) from 3-7 weeks of age. In the late intervention group, wild-type or Alport mice were treated once daily with sparsentan (120 mg/kg given orally; n=8/group), losartan (10 mg/kg given in drinking water; n=8/group), or vehicle (n=8) from 5-7 weeks of age. Blood pressure (BP) was determined weekly during the pilot study. For the renal studies, blood urea nitrogen (BUN) and urinary protein/creatinine ratio (UP/C) were determined at the end of the study, along with immunohistochemical (IHC) determination of CD45, fibronectin, and collagen 1 protein (COL1) in kidney sections as an assessment of leucocyte infiltration, glomerulosclerosis, and tubulointerstitial fibrosis, respectively. For the assessment of hearing mice were dosed up to 8.5 weeks of age. Auditory brain stem responses (ABR) were determined between 7 and 8 weeks of age following early intervention dosing and 5 days following a 10 h exposure to noise; n=5-7/group. Strial capillary basement width was also determined from transmission electron microscope images at the end of the study at 8.5 weeks of age; n=5/group.

The present disclosure generally relates to the use of biphenyl sulfonamide compounds that are dual angiotensin and endothelin receptor antagonists in the treatment of diseases associated with type IV collagen deficiencies or abnormalities, such as Alport syndrome.

In the following description, certain specific details are set forth in order to provide a thorough understanding of various embodiments of the invention. However, one skilled in the art will understand that the invention may be practiced without these details.

Unless defined otherwise, all technical and scientific terms used herein have the same meaning as is commonly understood by one of skill in the art to which this invention belongs. As used herein, certain terms may have the following defined meanings.

Unless the context requires otherwise, throughout the present specification and claims, the word "comprise" and variations thereof, such as "comprises" and "comprising," are to be construed in an open, inclusive sense, that is, as "including, but not limited to."

As used in the specification and claims, "including" and variants thereof, such as "include" and "includes," are to be construed in an open, inclusive sense; i.e., it is equivalent to "including, but not limited to." As used herein, the terms "include" and "have" are used synonymously, which terms and variants thereof are intended to be construed as non-limiting.

As used in herein, the phrase "such as" refers to non-limiting examples.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and claims, the singular for "a," "an," and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

The use of the alternative (e.g., "or") should be understood to mean either one, both, or any combination thereof of the alternatives.

"Optional" or "optionally" means that the subsequently described event of circumstances may or may not occur, and that the description includes instances where said event or circumstance occurs and instances in which it does not occur.

As used herein, "about" and "approximately" generally refer to an acceptable degree of error for the quantity measured, given the nature or precision of the measurements. Typical, exemplary degrees of error may be within 20%, 10%, or 5% of a given value or range of values. Alternatively, and particularly in biological systems, the terms "about" and "approximately" may mean values that are within an order of magnitude, potentially within 5-fold or 2-fold of a given value. When not explicitly stated, the terms "about" and "approximately" mean equal to a value, or within 20% of that value.

As used herein, numerical quantities are precise to the degree reflected in the number of significant figures reported. For example, a value of 0.1 is understood to mean from 0.05 to 0.14. As another example, the interval of values 0.1 to 0.2 includes the range from 0.05 to 0.24.

The compound having structure (I) forms salts that are also within the scope of this disclosure. Reference to a compound having structure (I) herein is understood to include reference to salts thereof, unless otherwise indicated. The term "salt(s)," as employed herein, denotes acidic, or basic salts formed with inorganic or organic acids and bases. In addition, as the compound having structure (I) contains both a basic moiety and an acidic moiety, zwitterions ("inner salts") may be formed and are included within the term "salt(s)," as used herein. Pharmaceutically acceptable (i.e., non-toxic, physiologically acceptable) salts are preferred, although other salts may be useful, e.g., in isolation or purification steps which may be employed during preparation. Salts of the compound having structure (I) may be formed, for example, by reacting the compound having structure (I) with an amount of acid or base, such as an equivalent amount, in a medium such as one in which the salt precipitates or in an aqueous medium followed by lyophilization.

The term "pharmaceutically acceptable salt" includes both acid and base addition salts.

Prodrugs and solvates of the compound having structure (I) are also contemplated. The term "prodrug" denotes a compound that, upon administration to a subject, undergoes chemical conversion by metabolic or chemical processes to yield a compound having structure (I), or a salt or solvate thereof. Solvates of the compound having structure (I) may be hydrates. Any tautomers are also contemplated.

Often crystallizations produce a solvate of the compound having structure (I), or a salt thereof. As used herein, the term "solvate" refers to an aggregate that comprises one or more molecules of a compound as disclosed herein with one or more molecules of solvent. In some embodiments, the solvent is water, in which case the solvate is a hydrate. Alternatively, in other embodiments, the solvent is an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. In some embodiments, the compounds disclosed herein may be a true solvate, while in other cases, the compounds disclosed herein merely retain adventitious water or are mixtures of water plus some adventitious solvent.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood, or other biological samples.

"Stable compound" and "stable structure" are meant to indicate a compound that is sufficiently robust to survive isolation to a useful degree of purity from a reaction mixture, and formulation into an efficacious therapeutic agent.

The term "subject" refers to a mammal, such as a domestic pet (for example, a dog or cat), or human. Preferably, the subject is a human. In some embodiments, the subject is a patient that has been diagnosed as having a disease or disorder.

The phrase "effective amount" refers to the amount which, when administered to a subject or patient for treating a disease, is sufficient to effect such treatment for the disease.

The term "dosage unit form" is the form of a pharmaceutical product, including, but not limited to, the form in which the pharmaceutical product is marketed for use. Examples include pills, tablets, capsules, and liquid solutions and suspensions.

"Treatment" or "treating" includes (1) inhibiting a disease in a subject or patient experiencing or displaying the pathology or symptomatology of the disease (e.g., arresting further development of the pathology or symptomatology); or (2) ameliorating a disease in a subject or patient that is experiencing or displaying the pathology or symptomatology of the disease (e.g., reversing the pathology or symptomatology); or (3) effecting any measurable decrease in a disease in a subject or patient that is experiencing or displaying the pathology or symptomatology of the disease.

Additional definitions are set forth throughout this disclosure.

Chemical Compounds and Methods of Preparation

The present disclosure generally relates to the use of biphenyl sulfonamide compounds that are dual angiotensin and endothelin receptor antagonists. In particular, the present disclosure relates to biphenyl sulfonamide compounds such as a compound having structure (I),

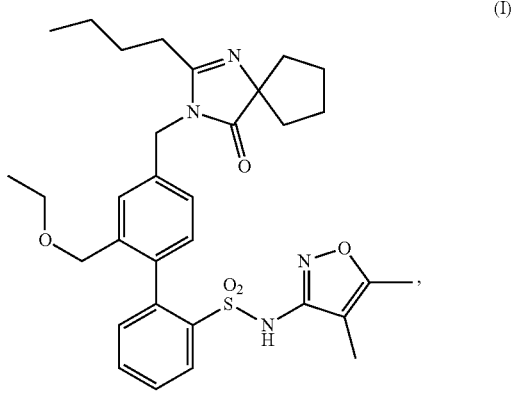 [SMILES: CCCCC1=NC2(CCCC2)C(=O)N1Cc1ccc(-c2ccccc2S(=O)(=O)Nc2noc(C)c2C)c(COCC)c1]

and pharmaceutically acceptable salts thereof. The compound of structure (I) is also known as sparsentan. Sparsentan is a selective dual-acting receptor antagonist with affinity for endothelin (A type) receptors ("ETA" receptors) and angiotensin II receptors (Type 1) ("$AT_1$" receptors) (Kowala et al., *JPET* 309: 275-284, 2004).

The compound of structure (I) may be prepared by methods such as those described in International Patent Application Publication No. WO2018/071784 A1.

Additionally, the compound of structure (I) may be prepared by the methods recited in U.S. Patent Application Publication No. US 2015/0164865 A1 and U.S. Pat. No. 6,638,937 B2.

Pharmaceutical Compositions and Methods of Use

In some embodiments, the present disclosure relates to the administration of a pharmaceutical composition comprising a compound of structure (I), or pharmaceutically acceptable salt thereof. The term "pharmaceutical composition" as used herein refers to a composition comprising an active ingredient and a pharmaceutically acceptable excipient. Pharmaceutical compositions may be used to facilitate administration of an active ingredient to an organism. Multiple techniques of administering a compound exist in the art, such as oral, injection, aerosol, parenteral, and topical administration. Pharmaceutical compositions can be obtained, for example, by reacting compounds with inorganic or organic acids such as hydrochloric acid, hydrobromic acid, sulfuric acid, nitric acid, phosphoric acid, methane sulfonic acid, ethanesulfonic acid, p-toluenesulfonic acid, salicylic acid, and the like. As used herein, the term "physiologically acceptable excipient" or "pharmaceutically acceptable excipient" refers to a physiologically and pharmaceutically suitable non-toxic and inactive material or ingredient that does not interfere with the activity of the active ingredient, including any adjuvant, carrier, glidant, sweetening agent, diluent, preservative, dye/colorant, flavor enhancer, surfactant, wetting agent, dispersing agent, suspending agent, stabilizer, isotonic agent, solvent, or emulsifier that has been approved by the United States Food and Drug Administration as being acceptable for use in humans or domestic animals.

In some embodiments, the pharmaceutical composition may be formulated as described below.

Additionally, methods of treating diseases or disorders by administering a pharmaceutical composition comprising a compound of structure (I), or pharmaceutically acceptable salt thereof, and a pharmaceutically acceptable excipient, are also within the scope of the present disclosure.

In one aspect, the compound of structure (I) and pharmaceutically acceptable salts thereof are useful in the treatment of Alport syndrome. Accordingly, in some embodiments, a method of treating Alport syndrome is provided, comprising administering to a subject in need thereof a compound of structure (I), or a pharmaceutically acceptable salt thereof. In some embodiments, the method of treating Alport syndrome comprises administering to a subject in need thereof an effective amount of a compound of structure (I), or a pharmaceutically acceptable salt thereof. In some embodiments, the method of treating Alport syndrome comprises administering to a subject in need thereof a pharmaceutical composition comprising a compound of structure (I), or a pharmaceutically acceptable salt thereof, and a pharmaceutically acceptable excipient. In still further embodiments, the pharmaceutical composition comprises a compound of structure (I), or a pharmaceutically acceptable salt thereof, in an effective amount for treating Alport syndrome.

In some further embodiments, the compound of structure (I) and pharmaceutically acceptable salts thereof, or a pharmaceutical composition comprising the compound of structure (I) and pharmaceutically acceptable salts thereof, are useful in the treatment of Alport syndrome.

In still further embodiments, the compound of structure (I) and pharmaceutically acceptable salts thereof are useful in the reduction of general morbidity or mortality as a result of the above utilities.

In some embodiments, the compound of structure (I) and pharmaceutically acceptable salts thereof are useful in maintaining glomerular filtration rate. As used herein, "glomerular filtration rate" ("GFR") is a measure of kidney function and refers to the amount of fluid filtered through the glomeruli of the kidney per unit of time. GFR may be estimated by measuring serum creatinine levels and using the Chronic Kidney Disease Epidemiology Collaboration (CKD-EPI) creatinine equation. As used herein, "estimated glomerular filtration rate" ("eGFR") refers to an estimate of GFR obtained from using the CKD-EPI creatinine equation. In some embodiments, the compound of structure (I) and pharmaceutically acceptable salts thereof are useful in maintaining eGFR levels (i.e., preventing a reduction in eGFR associated with Alport syndrome). In some embodiments, administering the compound of structure (I) and pharmaceutically acceptable salts thereof to a subject results in eGFR being maintained at or above eGFR levels immediately prior to administration of said pharmaceutical composition. As used herein, "maintenance of eGFR" refers to no clinically meaningful reduction in eGFR levels. Thus, as used herein, in reference to treatment of a patient having Alport syndrome, the phrase "maintain eGFR constant" means treatment that maintains the subject's eGFR at a level that is clinically equivalent to or better than their most recently calculated eGFR level prior to onset of treatment. In some embodiments, the eGFR is maintained for months or years after administration. The period of time during which the subject's eGFR level is maintained constant typically is at least 12 months.

In some embodiments, the compound of structure (I) and pharmaceutically acceptable salts thereof are useful in the treatment (e.g., prevention) of hearing loss associated with Alport syndrome, or hearing loss in a subject having Alport syndrome. Accordingly, in some embodiments, a method of treating (e.g., preventing) hearing loss associated with Alport syndrome is provided, comprising administering to a subject in need thereof a compound of structure (I), or a pharmaceutically acceptable salt thereof. In some embodiments, the method of treating (e.g., preventing) hearing loss associated with Alport syndrome comprises administering to a subject in need thereof an effective amount of a compound of structure (I), or a pharmaceutically acceptable salt thereof. In some other embodiments, the present disclosure provides a method of treating (e.g., preventing) hearing loss associated with Alport syndrome, comprising administering to a subject in need thereof a pharmaceutical composition comprising a compound of structure (I), or a pharmaceutically acceptable salt thereof, and a pharmaceutically acceptable excipient. In some further embodiments, the pharmaceutical composition comprises a compound of structure (I), or a pharmaceutically acceptable salt thereof, in an effective amount. As used herein, "prevention of, or preventing, hearing loss associated with Alport syndrome" refers to arresting hearing loss or slowing the rate of hearing loss associated with Alport syndrome. For example, preventing hearing loss associated with Alport syndrome includes stabilizing hearing as well as slowing a decline in hearing.

In some further embodiments, the compound of structure (I) and pharmaceutically acceptable salts thereof, or a pharmaceutical composition comprising the compound of structure (I) and pharmaceutically acceptable salts thereof, are useful in the methods of treating (e.g., preventing) hearing loss associated with Alport syndrome, or hearing loss in a subject having Alport syndrome.

In another aspect, the compound of structure (I) and pharmaceutically acceptable salts thereof are useful in the treatment (e.g., prevention) of hearing loss in subjects having diabetes. Accordingly, in some embodiments, a method of treating (e.g., preventing) hearing loss in a subject having diabetes is provided, comprising administering to a subject in need thereof a compound of structure (I), or a pharmaceutically acceptable salt thereof. In some embodiments, the method of treating (e.g., preventing) hearing loss in a diabetic subject comprises administering to a subject in need thereof an effective amount of a compound of structure (I), or a pharmaceutically acceptable salt thereof. In some embodiments, the method of treating (e.g., preventing) hearing loss in a diabetic subject comprises administering to a subject in need thereof a pharmaceutical composition comprising a compound of structure (I), or a pharmaceutically acceptable salt thereof, and a pharmaceutically acceptable excipient. In some embodiments, the pharmaceutical composition comprises a compound of structure (I), or a pharmaceutically acceptable salt thereof, in an effective amount. In some embodiments, the subject has Type 1 diabetes. In some embodiments, the subject has Type 1 diabetes and a mutation (e.g., a missense mutation) in a COL4A3 gene. In some embodiments, the subject has type 2 diabetes.

In some further embodiments, the compound of structure (I) and pharmaceutically acceptable salts thereof, or a pharmaceutical composition comprising the compound of structure (I) and pharmaceutically acceptable salts thereof, are useful in the methods of treating (e.g., preventing) hearing loss associated with diabetes, or in a subject having diabetes.

In another aspect, the compound of structure (I) and pharmaceutically acceptable salts thereof are useful in the treatment (e.g., prevention) of hearing loss in subjects having a mutation in a COL4A3, COL4A4, or COL4A5 gene. Accordingly, in some embodiments, a method of treating (e.g., preventing) hearing loss in a subject having a mutation (e.g., a missense mutation) in a COL4A3, COL4A4, or COL4A5 gene is provided, comprising administering to a subject in need thereof a compound of structure (I), or a pharmaceutically acceptable salt thereof. In some embodiments, the method of treating (e.g., preventing) hearing loss in a subject having a mutation in a COL4A3, COL4A4, or COL4A5 gene comprises administering to a subject in need thereof an effective amount of a compound of structure (I), or a pharmaceutically acceptable salt thereof. In some embodiments, the method of treating (e.g., preventing) hearing loss a subject having a mutation in a COL4A3, COL4A4, or COL4A5 gene comprises administering to a subject in need thereof a pharmaceutical composition comprising a compound of structure (I), or a pharmaceutically acceptable salt thereof, and a pharmaceutically acceptable excipient. In some embodiments, the pharmaceutical composition comprises a compound of structure (I), or a pharmaceutically acceptable salt thereof, in an effective amount. In some embodiments, the mutation is in a COL4A3 gene. In some embodiments, the mutation is in a COL4A4 gene. In some embodiments, the mutation is in a COL4A5 gene.

In some further embodiments, the compound of structure (I) and pharmaceutically acceptable salts thereof, or a pharmaceutical composition comprising the compound of structure (I) and pharmaceutically acceptable salts thereof, are useful in the methods of treating (e.g., preventing) hearing loss in a subject having a mutation (e.g., a missense mutation) in a COL4A3, COL4A4, or COL4A5 gene.

In another aspect, the compound of structure (I) and pharmaceutically acceptable salts thereof are useful in the treatment of subjects having a collagen type IV deficiency. Accordingly, in some embodiments, a method of treating a collagen type IV deficiency in a subject is provided, comprising administering to a subject in need thereof a compound of structure (I), or a pharmaceutically acceptable salt thereof. In some embodiments, the method of treating a collagen type IV deficiency in a subject comprises administering to a subject in need thereof an effective amount of a compound of structure (I), or a pharmaceutically acceptable salt thereof. In some embodiments, the method of treating a collagen type IV deficiency in a subject comprises administering to a subject in need thereof a pharmaceutical composition comprising a compound of structure (I), or a pharmaceutically acceptable salt thereof, and a pharmaceutically acceptable excipient. In some embodiments, the pharmaceutical composition comprises a compound of structure (I), or a pharmaceutically acceptable salt thereof, in an effective amount. In some embodiments, the subject has Alport syndrome. In some embodiments, the subject has Alport syndrome and a mutation (e.g., a missense mutation) in a COL4A5 gene. In some embodiments, the subject has diabetes. In some embodiments, the subject has Type 1 diabetes. In some embodiments, the subject has Type 1 diabetes and a mutation (e.g., a missense mutation) in a COL4A3 gene. In some embodiments, the subject has Type 2 diabetes.

In some further embodiments, the compound of structure (I) and pharmaceutically acceptable salts thereof, or a pharmaceutical composition comprising the compound of structure (I) and pharmaceutically acceptable salts thereof, are useful in the methods of treating a collagen type IV deficiency.

In some embodiments, any of the aforementioned uses or methods of treatment may comprise administering the compound of structure (I), or pharmaceutically acceptable salt thereof, or pharmaceutical composition comprising the same, in combination with one or more other active ingredients, such as other therapeutic or diagnostic agents. For example, in some embodiments, one or more other therapeutic agents may be administered prior to, simultaneously with, or following the administration of the pharmaceutical composition comprising an effective amount of a compound of structure (I), or a pharmaceutically acceptable salt thereof. If formulated as a fixed dose, such combination products may employ the compound of structure (I), or pharmaceutically acceptable salt thereof, within the dosage range described below, and the other active ingredient within its approved dosage range.

In some embodiments, the compound of structure (I), or pharmaceutically acceptable salt thereof, is used in conjunction with hemodialysis.

In some embodiments of the aforementioned uses and methods of treatment, the dosing regimen comprises administering the compound having structure (I) in an amount of 50 mg/day. In some embodiments, the dosing regimen comprises administering the compound having structure (I) in an amount of 100 mg/day. In some embodiments, the dosing regimen comprises administering the compound having structure (I) in an amount of 200 mg/day. In some embodiments, the dosing regimen comprises administering the compound having structure (I) in an amount of 300 mg/day. In some embodiments, the dosing regimen comprises administering the compound having structure (I) in an amount of 400 mg/day. In some embodiments, the dosing regimen comprises administering the compound having structure (I) in an amount of 500 mg/day. In some embodiments, the dosing regimen comprises administering the compound having structure (I) in an amount of 600 mg/day. In some embodiments, the dosing regimen comprises administering the compound having structure (I) in an amount of 700 mg/day. In some embodiments, the dosing regimen comprises administering the compound having structure (I) in an amount of 800 mg/day. In some embodiments, the dosing regimen comprises administering the compound having structure (I) in an amount of 900 mg/day. In some embodiments, the dosing regimen comprises administering the compound having structure (I) in an amount of 1000 mg/day.

In some embodiments of the aforementioned uses and methods of treatment, the dosing regimen comprises administering the compound having structure (I) in an amount of 200 mg/day for 8 weeks, 26 weeks, or 8 months. In still further embodiments, the dosing regimen comprises administering the compound having structure (I) in an amount of 400 mg/day for 8 weeks, 26 weeks, or 8 months. In still further embodiments, the dosing regimen comprises administering the compound having structure (I) in an amount of 800 mg/day for 8 weeks, 26 weeks, or 8 months.

In any of the aforementioned embodiments, the amount of the compound having structure (I), or pharmaceutically acceptable salt thereof, administered to the subject may be from about 50 mg/day to about 1000 mg/day. For example, in some embodiments, the amount of the compound having structure (I), or pharmaceutically acceptable salt thereof, administered to the subject is from about 200 mg/day to about 800 mg/day. In other embodiments, the amount of the compound having structure (I), or pharmaceutically acceptable salt thereof, administered to the subject is about 50 mg/day. In other embodiments, the amount of the compound having structure (I), or pharmaceutically acceptable salt thereof, administered to the subject is about 100 mg/day. In other embodiments, the amount of the compound having structure (I), or pharmaceutically acceptable salt thereof, administered to the subject is about 200 mg/day. In other embodiments, the amount of the compound having structure (I), or pharmaceutically acceptable salt thereof, administered to the subject is about 300 mg/day. In other embodiments, the amount of the compound having structure (I), or pharmaceutically acceptable salt thereof, administered to the subject is about 400 mg/day. In other embodiments, the amount of the compound having structure (I), or pharmaceutically acceptable salt thereof, administered to the subject is about 500 mg/day. In other embodiments, the amount of the compound having structure (I), or pharmaceutically acceptable salt thereof, administered to the subject is about 600 mg/day. In other embodiments, the amount of the compound having structure (I), or pharmaceutically acceptable salt thereof, administered to the subject is about 700 mg/day. In other embodiments, the amount of the compound having structure (I), or pharmaceutically acceptable salt thereof, administered to the subject is about 800 mg/day. In other embodiments, the amount of the compound having structure (I), or pharmaceutically acceptable salt thereof, administered to the subject is about 900 mg/day. In other embodiments, the amount of the compound having structure (I), or pharmaceutically acceptable salt thereof, administered to the subject is about 1000 mg/day.

In some embodiments of the aforementioned uses and methods of treatment, the amount of the compound having structure (I), or pharmaceutically acceptable salt thereof, administered to the subject is from 1 mg/kg to 15 mg/kg per day. In some embodiments, the amount of the compound having structure (I), or pharmaceutically acceptable salt thereof, administered to the subject is from 3 mg/kg to 12 mg/kg per day. In some embodiments, the amount of the compound having structure (I), or pharmaceutically acceptable salt thereof, administered to the subject is from 3 mg/kg to 6 mg/kg per day. In some of these embodiments, the subject is a child (e.g., less than 18 years of age; from 2 to 6 years of age; from 5 to 10 years of age; from 6 to 12 years of age).

In any of the aforementioned embodiments, the compound may be a compound having structure (I).

In any of the aforementioned embodiments, the method may further comprise administering to said subject one or more additional therapeutic agents.

In any of the aforementioned embodiments, the subject may be an adult or may be 18 years old or younger. In some embodiments, the subject is 18 years old or younger. In some embodiments, the subject is from 5 to 10 years of age. In some embodiments, the subject is from 6 to 12 years of age. In some embodiments, the subject is from 2 to 6 years of age.

In some embodiments, the present disclosure provides a pharmaceutical composition comprising a compound having structure (I), or a pharmaceutically acceptable salt thereof, and a pharmaceutically acceptable excipient for use in the aforementioned methods.

In some embodiments, the present disclosure provides for the use of a pharmaceutical composition comprising a compound having structure (I), or a pharmaceutically acceptable salt thereof, in the manufacture of a medicament for use in the aforementioned therapeutic methods.

The present disclosure also provides in further embodiments:

1. A pharmaceutical composition comprising a compound having structure (I),

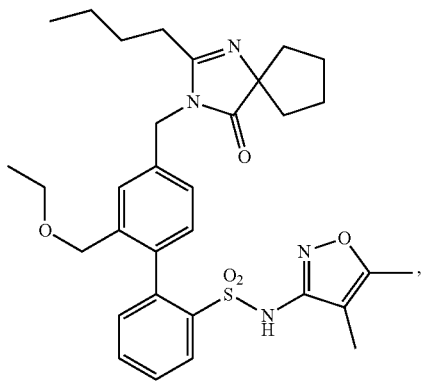

(I)

or a pharmaceutically acceptable salt thereof, for use in a method of treating hearing loss in a subject having Alport syndrome.

2. A pharmaceutical composition comprising a compound having structure (I),

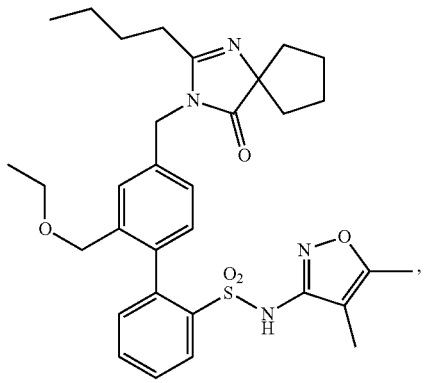

(I)

or a pharmaceutically acceptable salt thereof, for use in a method of treating hearing loss in a subject having a mutation in a COL4A3, COL4A4, or COL4A5 gene.

3. The pharmaceutical composition for use according to embodiment 2, wherein said mutation is in a COL4A3 gene.

4. The pharmaceutical composition for use according to embodiment 2, wherein said mutation is in a COL4A4 gene.

5. The pharmaceutical composition for use according to embodiment 2, wherein said mutation is in a COL4A5 gene.

6. The pharmaceutical composition for use according to any one of embodiments 2-5, wherein said mutation is a missense mutation.

7. A pharmaceutical composition comprising a compound having structure (I),

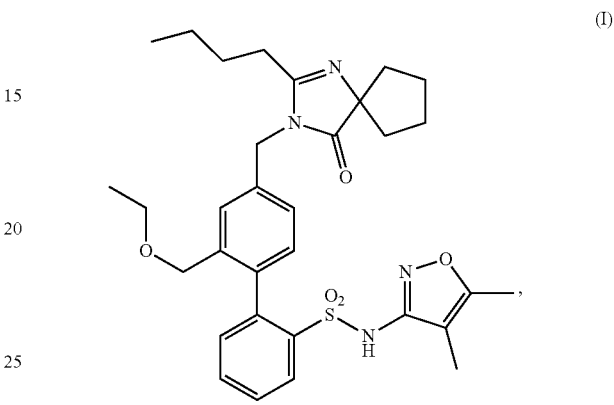

(I)

or a pharmaceutically acceptable salt thereof, for use in a method of treating Alport syndrome.

8. The pharmaceutical composition for use according to embodiment 7, wherein said compound of structure (I) or pharmaceutically acceptable salt thereof is administered in an amount sufficient to maintain said subject's eGFR constant.

9. The pharmaceutical composition for use according to embodiment 7 or embodiment 8, wherein after administration of said pharmaceutical composition the eGFR of said subject is maintained at or above eGFR levels immediately prior to administration of said pharmaceutical composition.

10. A pharmaceutical composition comprising a compound having structure (I),

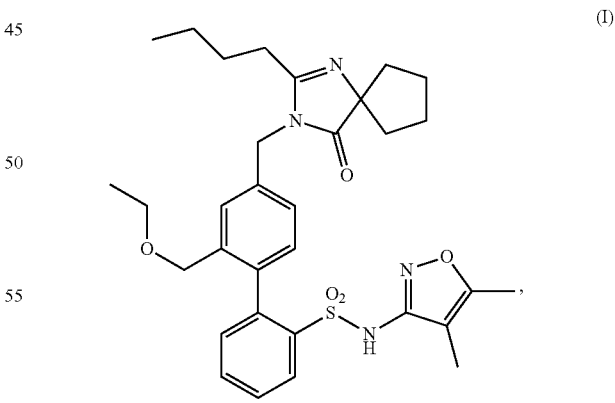

(I)

or a pharmaceutically acceptable salt thereof, for use in a method of treating hearing loss in a subject having diabetes.

11. The pharmaceutical composition for use according to embodiment 10, wherein said subject has Type 1 diabetes.

12. The pharmaceutical composition for use according to embodiment 11, wherein said subject has a mutation in a COL4A3 gene.

13. The pharmaceutical composition for use according to embodiment 10, wherein said subject has Type 2 diabetes.

14. A pharmaceutical composition comprising a compound having structure (I), (I)

or a pharmaceutically acceptable salt thereof, for use in a method of treating a collagen type IV deficiency.

15. The pharmaceutical composition for use according to embodiment 14, wherein said subject has Alport syndrome.

16. The pharmaceutical composition for use according to embodiment 15, wherein said subject has a mutation in the COL4A5 gene.

17. The pharmaceutical composition for use according to embodiment 14, wherein said subject has diabetes.

18. The pharmaceutical composition for use according to embodiment 17, wherein said subject has Type 1 diabetes.

19. The pharmaceutical composition for use according to embodiment 17 or embodiment 18, wherein said subject has a mutation in a COL4A3 gene.

20. The pharmaceutical composition for use according to embodiment 17, wherein said subject has Type 2 diabetes.

21. A method of treating hearing loss in a subject having Alport syndrome, comprising administering a pharmaceutical composition comprising a compound having structure (I), (I)

or a pharmaceutically acceptable salt thereof, to said subject.

22. A method of treating hearing loss in a subject having a mutation in a COL4A3, COL4A4, or COL4A5 gene, comprising administering a pharmaceutical composition comprising a compound having structure (I), (I)

or a pharmaceutically acceptable salt thereof, to said subject.

23. The method according to embodiment 22, wherein said mutation is in a COL4A3 gene.

24. The method according to embodiment 22, wherein said mutation is in a COL4A4 gene.

25. The method according to embodiment 22, wherein said mutation is in a COL4A5 gene.

26. The method according to any one of embodiments 22-25, wherein said mutation is a missense mutation.

27. A method of treating Alport syndrome in a subject, comprising administering a pharmaceutical composition comprising a compound having structure (I), (I)

or a pharmaceutically acceptable salt thereof, to said subject.

28. The method according to embodiment 27, wherein said compound of structure (I) or pharmaceutically acceptable salt thereof is administered in an amount sufficient to maintain said subject's eGFR constant.

29. The method according to embodiment 27 or embodiment 28, wherein after administration of said pharmaceutical composition the eGFR of said subject is maintained at or above eGFR levels immediately prior to administration of said pharmaceutical composition.

30. A method of treating hearing loss in a subject having diabetes, comprising administering a pharmaceutical composition comprising a compound having structure (I), or a pharmaceutically acceptable salt thereof, to said subject.

31. The method according to embodiment 30, wherein said subject has Type 1 diabetes.

32. The method according to embodiment 31, wherein said subject has a mutation in a COL4A3 gene.

33. The method according to embodiment 30, wherein said subject has Type 2 diabetes.

34. A method of treating a collagen type IV deficiency in a subject, comprising administering a pharmaceutical composition comprising a compound having structure (I), or a pharmaceutically acceptable salt thereof, to said subject.

35. The method according to embodiment 34, wherein said subject has Alport syndrome. 36. The method according to embodiment 35, wherein said subject has a mutation in a COL4A5 gene.

37. The method according to embodiment 34, wherein said subject has diabetes.

38. The method according to embodiment 37, wherein said subject has Type 1 diabetes.

39. The method according to embodiment 37 or embodiment 38, wherein said subject has a mutation in a COL4A3 gene.

40. The method according to embodiment 37, wherein said subject has Type 2 diabetes.

41. The use of a pharmaceutical composition comprising a compound having structure (I), or a pharmaceutically acceptable salt thereof, in the manufacture of a medicament for the treatment of hearing loss in a subject having Alport syndrome.

42. The use of a pharmaceutical composition comprising a compound having structure (I), or a pharmaceutically acceptable salt thereof, in the manufacture of a medicament for the treatment of hearing loss in a subject having a mutation in a COL4A3, COL4A4, or COL4A5 gene.

43. The use according to embodiment 42, wherein said mutation is in a COL4A3 gene.

44. The use according to embodiment 42, wherein said mutation is in a COL4A4 gene.

45. The use according to embodiment 42, wherein said mutation is in a COL4A5 gene.

46. The use according to any one of embodiments 42-45, wherein said mutation is a missense mutation.

47. The use of a pharmaceutical composition comprising a compound having structure (I),

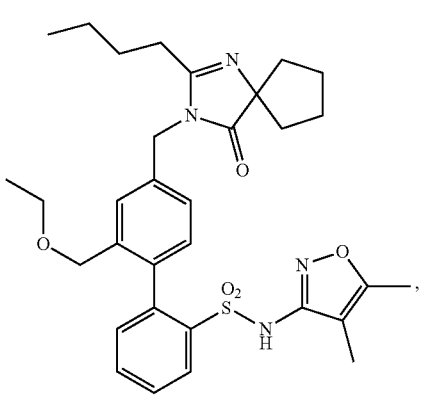

(I)

or a pharmaceutically acceptable salt thereof, in the manufacture of a medicament for the treatment of Alport syndrome.

48. The use according to embodiment 47, wherein said compound of structure (I) or pharmaceutically acceptable salt thereof is administered in an amount sufficient to maintain said subject's eGFR constant.

49. The use according to embodiment 47 or embodiment 48, wherein after administration of said pharmaceutical composition the eGFR of said subject is maintained at or above eGFR levels immediately prior to administration of said pharmaceutical composition.

50. The use of a pharmaceutical composition comprising a compound having structure (I),

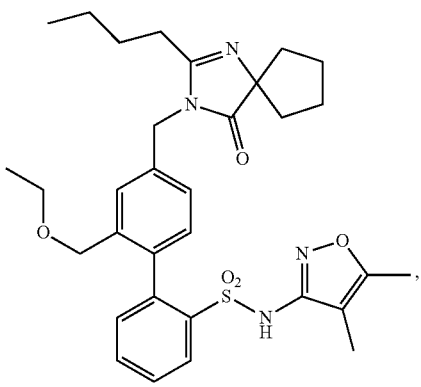

(I)

or a pharmaceutically acceptable salt thereof, in the manufacture of a medicament for the treatment of hearing loss in a subject having diabetes.

51. The use according to embodiment 50, wherein said subject has Type 1 diabetes.

52. The use according to embodiment 51, wherein said subject has a mutation in a COL4A3 gene.

53. The use according to embodiment 50, wherein said subject has Type 2 diabetes.

54. The use of a pharmaceutical composition comprising a compound having structure (I),

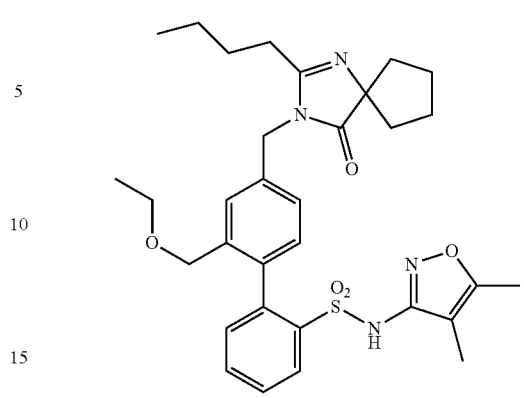

(I)

or a pharmaceutically acceptable salt thereof, in the manufacture of a medicament for the treatment of a collagen type IV deficiency.

55. The use according to embodiment 54, wherein said subject has Alport syndrome.

56. The use according to embodiment 54, wherein said subject has a mutation in a COL4A5 gene.

57. The use according to embodiment 54, wherein said subject has diabetes. 58. The use according to embodiment 57, wherein said subject has Type 1 diabetes.

59. The use according to embodiment 57 or embodiment 58, wherein said subject has a mutation in a COL4A3 gene.

60. The use according to embodiment 57, wherein said subject has Type 2 diabetes.

61. The pharmaceutical composition for use, method, or use in manufacture according to any preceding embodiment, wherein the amount of said compound having structure (I), or pharmaceutically acceptable salt thereof, administered to said subject is from about 1 mg/kg to about 15 mg/kg.

62. The pharmaceutical composition for use, method, or use in manufacture according to any preceding embodiment, wherein the amount of said compound having structure (I), or pharmaceutically acceptable salt thereof, administered to said subject is from about 3 mg/kg to about 12 mg/kg.

63. The pharmaceutical composition for use, method, or use in manufacture according to any preceding embodiment, wherein the amount of said compound having structure (I), or pharmaceutically acceptable salt thereof, administered to said subject is from about 3 mg/kg to about 6 mg/kg.

64. The pharmaceutical composition for use, method, or use in manufacture according to any preceding embodiment, wherein the amount of said compound having structure (I), or pharmaceutically acceptable salt thereof, administered to said subject is from about 1 mg/kg to about 15 mg/kg per day.

65. The pharmaceutical composition for use, method, or use in manufacture according to any preceding embodiment, wherein the amount of said compound having structure (I), or pharmaceutically acceptable salt thereof, administered to said subject is from about 3 mg/kg to about 12 mg/kg per day.

66. The pharmaceutical composition for use, method, or use in manufacture according to any preceding embodiment, wherein the amount of said compound having structure (I), or pharmaceutically acceptable salt thereof, administered to said subject is from about 3 mg/kg to about 6 mg/kg per day.

67. The pharmaceutical composition for use, method, or use in manufacture according to any preceding embodiment, wherein the amount of said compound having structure (I), or pharmaceutically acceptable salt thereof, administered to said subject is from about 50 mg/day to about 1000 mg/day.

68. The pharmaceutical composition for use, method, or use in manufacture according to embodiment 67, wherein the amount of the compound having structure (I), or pharmaceutically acceptable salt thereof, administered to said subject is from about 200 mg/day to about 800 mg/day.

69. The pharmaceutical composition for use, method, or use in manufacture according to embodiment 67, wherein the amount of the compound having structure (I), or pharmaceutically acceptable salt thereof, administered to said subject is from about 400 mg/day to about 800 mg/day.

70. The pharmaceutical composition for use, method, or use in manufacture according to embodiment 67, wherein the amount of said compound having structure (I), or pharmaceutically acceptable salt thereof, administered to said subject is about 100 mg/day, 200 mg/day, 300 mg/day, 400 mg/day, 500 mg/day, 600 mg/day, 700 mg/day, 800 mg/day, 900 mg/day or 1000 mg/day.

71. The pharmaceutical composition for use according to embodiment 64, wherein the amount of said compound having structure (I), or pharmaceutically acceptable salt thereof, administered to said subject is about 200 mg/day.

72. The pharmaceutical composition for use, method, or use in manufacture according to embodiment 64, wherein the amount of said compound having structure (I), or pharmaceutically acceptable salt thereof, administered to said subject is about 400 mg/day.

73. The pharmaceutical composition for use, method, or use in manufacture according to embodiment 64, wherein the amount of said compound having structure (I), or pharmaceutically acceptable salt thereof, administered to said subject is about 800 mg/day.

74. The pharmaceutical composition for use, method, or use in manufacture according to any preceding embodiment, wherein said compound has structure (I).

75. The pharmaceutical composition for use, method, or use in manufacture according to any preceding embodiment, wherein said subject is administered one or more additional therapeutic agents.

76. The pharmaceutical composition for use, method, or use in manufacture according to any preceding embodiment, wherein said subject is an adult.

77. The pharmaceutical composition for use, method, or use in manufacture according to any one of embodiments 1-75, wherein said subject is 18 years old or younger.

78. The pharmaceutical composition for use, method, or use in manufacture according to any one of embodiments 1-75, wherein said subject is 12 years old or younger.

79. The pharmaceutical composition for use, method, or use in manufacture according to any one of embodiments 1-75, wherein said subject is from 6 to 12 years of age.

80. The pharmaceutical composition for use, method, or use in manufacture according to any one of embodiments 1-75, wherein said subject is from 2 to 6 years of age.

81. The pharmaceutical composition for use, method, or use in manufacture according to any one of embodiments 77-80, wherein the pharmaceutical composition is a liquid formulation for oral administration.

Pharmaceutical Formulations

In one aspect, the present disclosure relates to the administration of a pharmaceutical composition comprising the compound of structure (I), or a pharmaceutically acceptable salt thereof, and pharmaceutically acceptable excipient. Techniques for formulation and administration of the compound of structure (I), or pharmaceutically acceptable salt thereof, may be found, for example, in "Remington's Pharmaceutical Sciences," Mack Publishing Co., Easton, Pa., 18th edition, 1990. In some embodiments, the pharmaceutical composition is formulated as described below.

In some embodiments, an excipient includes any substance, not itself a therapeutic agent, used as a carrier, diluent, adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. For example, an excipient may be a surface active agent (or "surfactant"), carrier, diluent, disintegrant, binding agent, wetting agent, polymer, lubricant, glidant, coating or coating assistant, film forming substance, sweetener, solubilizing agent, smoothing agent, suspension agent, substance added to mask or counteract a disagreeable taste or odor, flavor, colorant, fragrance, or substance added to improve appearance of the composition, or a combination thereof.

Acceptable excipients include, for example, microcrystalline cellulose, lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, polyvinyl alcohol, saline, dextrose, mannitol, lactose monohydrate, lecithin, albumin, sodium glutamate, cysteine hydrochloride, croscarmellose sodium, sodium starch glycolate, hydroxypropyl cellulose, poloxamer (e.g., poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, and poloxamer 105 benzoate, poloxamer 182 dibenzoate 407, and the like), sodium lauryl sulfate, colloidal silicon dioxide, and the like. Examples of suitable excipients for tablets and capsules include microcrystalline cellulose, silicified microcrystalline cellulose, lactose monohydrate, croscarmellose sodium, sodium starch, hydroxypropyl cellulose, poloxamer 188, sodium lauryl sulfate, colloidal silicon dioxide, and magnesium stearate. Examples of suitable excipients for soft gelatin capsules include vegetable oils, waxes, fats, and semisolid and liquid polyols. Suitable excipients for the preparation of solutions and syrups include, for example, water, polyols, sucrose, invert sugar, and glucose. The compound can also be made in microencapsulated form. If desired, absorption enhancing preparations (for example, liposomes), can be utilized. Acceptable excipients for therapeutic use are well known in the pharmaceutical art, and are described, for example, in "Handbook of Pharmaceutical Excipients," 5th edition (Raymond C Rowe, Paul J Sheskey and Siân C Owen, eds. 2005), and "Remington: The Science and Practice of Pharmacy," 21st edition (Lippincott Williams & Wilkins, 2005).

In some embodiments, surfactants are used. The use of surfactants as wetting agents in oral drug forms is described in the literature, for example in H. Sucker, P. Fuchs, P. Speiser, *Pharmazeutische Technologie,* 2nd edition, Thieme 1989, page 260. It is known from other papers, such as published in *Advanced Drug Delivery Reviews* (1997), 23, pages 163-183, that it is also possible to use surfactants, inter alia, to improve the permeation and bioavailability of pharmaceutical active compounds. Examples of surfactants include anionic surfactants, non-ionic surfactants, zwitterionic surfactants, and a mixture thereof. In some embodiments, the surfactant is selected from the group consisting of poly(oxyethylene) sorbitan fatty acid ester, poly(oxyethylene) stearate, poly(oxyethylene) alkyl ether, polyglycolated glyceride, poly(oxyethylene) castor oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

As used herein, the term "carrier" defines a chemical compound that facilitates the incorporation of a compound into cells or tissues. For example, dimethyl sulfoxide (DMSO) is a commonly utilized carrier, as it facilitates the uptake of many organic compounds into the cells or tissues of an organism. As used herein, the term "diluent" defines chemical compounds diluted in water that will dissolve the compound of interest as well as stabilize the biologically active form of the compound. Salts dissolved in buffered solutions are commonly utilized as diluents in the art. One commonly used buffered solution is phosphate buffered saline because it mimics the salt conditions of human blood. Because buffer salts can control the pH of a solution at low concentrations, a buffered diluent rarely modifies the biological activity of a compound. In some embodiments, a diluent selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt, and glycerol, polydextrose, starch, and the like, or any mixture thereof, is used. Acceptable carriers or diluents for therapeutic use are well known in the pharmaceutical art, and are described, for example, in "Remington's Pharmaceutical Sciences," 18th Ed., Mack Publishing Co., Easton, Pa. (1990).

In some embodiments, disintegrants such as starches, clays, celluloses, algins, gums, or crosslinked polymers are used, for example, to facilitate tablet disintegration after administration. Suitable disintegrants include, for example, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. In some embodiments, the formulation can also contain minor amounts of nontoxic auxiliary substances such as wetting or emulsifying agents, pH buffering agents, and the like; for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, and the like.

In some embodiments, binders are used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), and the like. Accordingly, in some embodiments, a formulations disclosed herein includes at least one binder to enhance the compressibility of the major excipient(s). For example, the formulation can include at least one of the following binders in the following ranges: from about 2% to about 6% w/w hydroxypropyl cellulose (Klucel); from about 2% to about 5% w/w polyvinylpyrrolidone (PVP); from about 1% to about 5% w/w methylcellulose; from about 2% to about 5% hydroxypropyl methylcellulose; from about 1% to about 5% w/w ethylcellulose; from about 1% to about 5% w/w sodium carboxy methylcellulose; and the like. One of ordinary skill in the art would recognize additional binders and/or amounts that can be used in the formulations described herein. As would be recognized by one of ordinary skill in the art, when incorporated into the formulations disclosed herein, the amounts of the major filler(s) and/or other excipients can be reduced accordingly to accommodate the amount of binder added in order to keep the overall unit weight of the dosage form unchanged. In some embodiments, a binder is sprayed on from solution, e.g., wet granulation, to increase binding activity.

In some embodiments, a lubricant is employed in the manufacture of certain dosage forms. For example, a lubricant may be employed when producing tablets. In some embodiments, a lubricant can be added just before the tableting step, and can be mixed with the other ingredients for a minimum period of time to obtain good dispersal. In some embodiments, one or more lubricants may be used. Examples of suitable lubricants include magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate, and mixtures of magnesium stearate with sodium lauryl sulfate. Lubricants may comprise from about 0.25% to about 50% of the tablet weight, typically from about 1% to about 40%, more typically from about 5% to about 30%, and most typically from 20% to 30%. In some embodiments, magnesium stearate can be added as a lubricant, for example, to improve powder flow, prevent the blend from adhering to tableting equipment and punch surfaces, and provide lubrication to allow tablets to be cleanly ejected from tablet dies. In some embodiments, magnesium stearate may be added to pharmaceutical formulations at concentrations ranging from about 0.1% to about 5.0% w/w, or from about 0.25% to about 4% w/w, or from about 0.5% w/w to about 3% w/w, or from about 0.75% to about 2% w/w, or from about 0.8% to about 1.5% w/w, or from about 0.85% to about 1.25% w/w, or from about 0.9% to about 1.20% w/w, or from about 0.85% to about 1.15% w/w, or from about 0.90% to about 1.1.% w/w, or from about 0.95% to about 1.05% w/w, or from about 0.95% to about 1% w/w. The above ranges are examples of typical ranges. One of ordinary skill in the art would recognize additional lubricants and/or amounts that can be used in the formulations described herein. As would be recognized by one of ordinary skill in the art, when incorporated into the pharmaceutical compositions disclosed herein, the amounts of the major filler(s) and/or other excipients may be reduced accordingly to accommodate the amount of lubricant(s) added in order to keep the overall unit weight of the dosage form unchanged.

In some embodiments, glidants are used. Examples of glidants include colloidal silicon dioxide, magnesium trisilicate, powdered cellulose, starch, talc, and calcium phosphate, and the like, and mixtures thereof.

In some embodiments, the formulations can include a coating, for example, a film coating. Where film coatings are included, coating preparations may include, for example, a film-forming polymer, a plasticizer, or the like. Also, the coatings may include pigments or opacifiers. Examples of film-forming polymers include hydroxypropyl methylcellulose, hydroxypropyl cellulose, methylcellulose, polyvinyl pyrrolidine, and starches. Examples of plasticizers include polyethylene glycol, tributyl citrate, dibutyl sebecate, castor oil, and acetylated monoglyceride. Furthermore, examples of pigments and opacifiers include iron oxides of various colors, lake dyes of many colors, titanium dioxide, and the like.

In some embodiments, color additives are included. The colorants can be used in amounts sufficient to distinguish dosage form strengths. In some embodiments, color additives approved for use in drugs (see 21 C.F.R. pt. 74) are added to the commercial formulations to differentiate tablet strengths. The use of other pharmaceutically acceptable colorants and combinations thereof is also encompassed by the current disclosure.

The pharmaceutical compositions as disclosed herein may include any other agents that provide improved transfer, delivery, tolerance, and the like. These compositions may include, for example, powders, pastes, jellies, waxes, oils, lipids, lipid (cationic or anionic) containing vesicles (such as Lipofectin®), DNA conjugates, anhydrous absorption pastes, oil-in-water and water-in-oil emulsions, emulsions of Carbowax (polyethylene glycols of various molecular weights), semi-solid gels, and semisolid mixtures containing Carbowax.

In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil, and the like may be used as smoothing agents; coconut oil, olive oil, sesame oil, peanut oil, and soya may be used as suspension agents or lubricants; cellulose acetate phthalate as a derivative of a carbohydrate such as cellulose or sugar, methyl acetatemethacrylate copolymer as a derivative of polyvinyl, or plasticizers such as ester phthalate may be used as suspension agents.

In some embodiments, a pharmaceutical composition as disclosed herein further comprises one or more of preservatives, stabilizers, dyes, sweeteners, fragrances, flavoring agents, and the like. For example, sodium benzoate, ascorbic acid, and esters of p-hydroxybenzoic acid may be included as preservatives. Antioxidants and suspending agents may also be included in the pharmaceutical composition.

In addition to being used as a monotherapy, the compounds and pharmaceutical compositions disclosed herein may also find use in combination therapies. Effective combination therapy may be achieved with a single pharmaceutical composition that includes multiple active ingredients, or with two or more distinct pharmaceutical compositions. Alternatively, each therapy may precede or follow the other by intervals ranging from minutes to months.

In some embodiments, one or more of, or any combination of, the listed excipients can be specifically included or excluded from the pharmaceutical compositions or methods disclosed herein.

Any of the foregoing formulations may be appropriate in treatments and therapies in accordance with the disclosure herein, provided that the one or more active ingredient in the pharmaceutical composition is not inactivated by the formulation and the formulation is physiologically compatible and tolerable with the route of administration (see also Baldrick P., "Pharmaceutical excipient development: the need for preclinical guidance." *Regul. Toxicol. Pharmacol.* 32(2):210-8 (2000); Charman W. N., "Lipids, lipophilic drugs, and oral drug delivery-some emerging concepts." *J. Pharm. Sci.* 89(8):967-78 (2000), and the citations therein for additional information related to formulations, excipients, and carriers well known to pharmaceutical chemists).

In some embodiments, the above excipients can be present in an amount up to about 95% of the total composition weight, or up to about 85% of the total composition weight, or up to about 75% of the total composition weight, or up to about 65% of the total composition weight, or up to about 55% of the total composition weight, or up to about 45% of the total composition weight, or up to about 43% of the total composition weight, or up to about 40% of the total composition weight, or up to about 35% of the total composition weight, or up to about 30% of the total composition weight, or up to about 25% of the total composition weight, or up to about 20% of the total composition weight, or up to about 15% of the total composition weight, or up to about 10% of the total composition weight, or less.

As will be appreciated by those of skill in the art, the amounts of excipients will be determined by drug dosage and dosage form size. In some embodiments disclosed herein, the dosage form size is about 200 mg to 800 mg. In some embodiments disclosed herein, the dosage form size is about 200 mg. In a further embodiment disclosed herein, the dosage form size is about 400 mg. In a further embodiment disclosed herein, the dosage form size is about 800 mg. One skilled in the art will realize that a range of weights may be made and are encompassed by this disclosure.

The pharmaceutical compositions of the present disclosure may be manufactured in a manner that is itself known, e.g., by means of conventional mixing, dissolving, granulating, dragee-making, levigating, emulsifying, encapsulating, entrapping, or tableting processes.

The pharmaceutical compositions of the present disclosure may provide low-dose formulations of the compound of structure (I), or a pharmaceutically acceptable salt thereof, in tablets, film coated tablets, capsules, caplets, pills, gel caps, pellets, beads, or dragee dosage forms. The formulations disclosed herein can provide favorable drug processing qualities, including, for example, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

Proper formulation is dependent upon the route of administration chosen. Suitable routes for administering the compound of structure (I), or a pharmaceutically acceptable salt thereof, or a pharmaceutical composition comprising the same, may include, for example, oral, rectal, transmucosal, topical, or intestinal administration; and parenteral delivery, including intramuscular, subcutaneous, intravenous, intramedullary injections, intrathecal, direct intraventricular, intraperitoneal, intranasal, or intraocular injections. The compound of structure (I), or a pharmaceutically acceptable salt thereof, may also be administered in sustained or controlled release dosage forms, including depot injections, osmotic pumps, pills, transdermal (including electrotransport) patches, and the like, for prolonged or timed, pulsed administration at a predetermined rate.

Injectables can be prepared in conventional forms, either as liquid solutions or suspensions, solid forms suitable for solution or suspension in liquid prior to injection, or as emulsions. Suitable excipients may include, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include Hanks' solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit, or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, or dispersing agents. Alternatively, the active ingredient may be in powder form for constitution with a suitable vehicle, e.g., sterile pyrogen-free water, before use.

For oral administration, the compound of structure (I), or a pharmaceutically acceptable salt thereof, can be formulated by combining the active compound with pharmaceutically acceptable carriers known in the art. Such carriers enable the compound to be formulated as tablets, film coated tablets, pills, dragees, capsules, liquids, gels, get caps, pellets, beads, syrups, slurries, suspensions, and the like, for oral ingestion by a patient to be treated.

Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients may be, in particular, fillers such as sugars, including lactose, sucrose, mannitol, or sorbitol; and cellulose preparations such as, for example, maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Dragee cores having suitable coatings are also within the scope of the disclosure. For this purpose, concentrated sugar solutions may be used, which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, titanium dioxide, lacquer solutions, or suitable organic solvents or solvent mixtures. Dyestuffs or pigments may be added to the tablets or dragee coatings for identification or to characterize different combinations of active compound doses. In addition, stabilizers can be added. In some embodiments, formulations for oral administration are in dosages suitable for such administration. In some embodiments, formulations of the compound of structure (I), or a pharmaceutically acceptable salt thereof, have an acceptable immediate release dissolution profile and a robust, scalable method of manufacture.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, or lubricants such as talc or magnesium stearate, and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in a conventional manner.

For administration by inhalation, the compound of structure (I), or a pharmaceutically acceptable salt thereof, is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum (Shedden et al., *Clin. Ther.* 23(3):440-50, 2001) or hydrogels (Mayer et al., *Ophthalmologica* 210(2):101-3, 1996); ophthalmic ointments; ophthalmic suspensions, such as microparticulates, drug-containing small polymeric particles that are suspended in a liquid carrier medium (Joshi, *J. Ocul. Pharmacol.* 10(1):29-45, 1994), lipid-soluble formulations (Alm et al., *Prog. Clin. Biol. Res.* 312:447-58, 1989), and microspheres (Mordenti, *Toxicol. Sci.* 52(1):101-6, 1999); and ocular inserts. Such suitable pharmaceutical formulations may be formulated to be sterile, isotonic, and buffered for stability and comfort. Pharmaceutical compositions for intranasal delivery may also include drops and sprays often prepared to simulate in many respects nasal secretions, to ensure maintenance of normal ciliary action. As disclosed in "Remington's Pharmaceutical Sciences," 18th Ed., Mack Publishing Co., Easton, Pa. (1990), and well known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound of structure (I), or a pharmaceutically acceptable salt thereof, may also be formulated in rectal compositions such as suppositories or retention enemas, e.g., those containing conventional suppository bases such as cocoa butter or other glycerides.

In addition to the formulations described previously, the compound of structure (I), or pharmaceutically acceptable salt thereof, may also be formulated as a depot preparation. Such long acting formulations may be administered by implantation (for example subcutaneously or intramuscularly) or by intramuscular injection. Thus, for example, the compound of structure (I), or a pharmaceutically acceptable salt thereof, may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. The proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well-known examples of delivery vehicles or carriers for hydrophobic drugs. In some embodiments, certain organic solvents such as dimethylsulfoxide also may be employed.

Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. Molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

In some embodiments, a liquid formulation of sparsentan is provided for use in the compositions and methods described herein. In some embodiments, the liquid formulation comprises sparsentan and a diluent or vehicle, such as water. In some embodiments, the liquid formulation further comprises (a) a preservative, such as potassium sorbate or sodium benzoate; (b) a sweetener, such as sucralose or sodium saccharin; (c) a flavoring agent; (d) a viscosity modifier such as xanthan gum, microcrystalline cellulose/ sodium carboxymethylcellulose composite, methyl cellulose, or hydroxyethyl cellulose; or (e) a pH modifier, such as citric acid, tartaric acid, or sodium citrate; or combinations thereof. For example, in some embodiments, the liquid formulation of sparsentan comprises sparsentan, water as a diluent or vehicle, sodium benzoate, sucralose, a flavoring agent, xanthan gum, and citric acid. In some embodiments, the liquid formulation is administered orally to a subject who is 18 years old or younger, 12 years old or younger, from 6 to 12 years of age, or from 2 to 6 years of age.

Methods of Administration

The compound of structure (I), or a pharmaceutically acceptable salt thereof, or pharmaceutical compositions comprising the same, may be administered to the patient by any suitable means. Examples of methods of administration include (a) administration though oral pathways, which includes administration in capsule, tablet, granule, spray, syrup, and other such forms; (b) administration through non-oral pathways such as rectal, vaginal, intraurethral, intraocular, intranasal, and intraauricular, which includes administration as an aqueous suspension, an oily preparation, or the like as a drip, spray, suppository, salve, ointment, or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; and (e) administration topically; as deemed appropriate by those of skill in the art for bringing the compound of structure (I), or pharmaceutically acceptable salt thereof, into contact with living tissue.

Pharmaceutical compositions suitable for administration include compositions where the compound of structure (I), or a pharmaceutically acceptable salt thereof, is contained in an amount effective to achieve its intended purpose. The dose can be tailored to achieve a desired effect, but will depend on such factors as weight, diet, concurrent medication, and other factors that those skilled in the medical arts will recognize. More specifically, a "therapeutically effective amount" means an amount of compound effective to provide a therapeutic benefit to the subject being treated.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will be dependent on many factors including the subject being treated, the severity of the affliction, the manner of administration, and the judgment of the prescribing physician. In some embodiments, the compound of structure (I), or pharmaceutically acceptable salt thereof, may be administered orally or via injection at a dose from 0.001 mg/kg to 2500 mg/kg of the patient's body weight per day. In a further embodiment, the dose range for adult humans is from 0.01 mg to 10 g/day. Tablets or other forms of presentation provided in discrete units may conveniently contain an amount of the compound of structure (I), or a pharmaceutically acceptable salt thereof, that is effective at such dosage or as a multiple of the same, for instance, units containing 5 mg to 1000 mg, usually from about 100 mg to about 800 mg. The dose employed will depend on a number of factors, including the age and sex of the patient, the precise disease or disorder being treated, and its severity. Also, the route of administration may vary depending on the condition and its severity.

In cases wherein a salt is administered, dosages may be calculated as the dose of the free base.

In some embodiments, the dose range of the pharmaceutical composition administered to the patient can be from about 0.01 mg/kg to about 1000 mg/kg of the patient's body weight. The dosage may be a single one or a series of two or more given in the course of one or more days, as is needed by the patient.

In some embodiments, the daily dosage regimen for an adult human patient may be, for example, an oral dose of each active ingredient of between 0.1 mg and 2000 mg, or between 1 mg and 1500 mg, or between 5 mg to 1000 mg. In other embodiments, an oral dose of each active ingredient of between 1 mg and 1000 mg, between 50 mg and 900 mg, and between 100 mg to 800 mg is administered. In some embodiments, the oral dose is administered 1 to 4 times per day. In some embodiments, compositions of the compound of structure (I), or a pharmaceutically acceptable salt thereof, may be administered by continuous intravenous infusion, at a dose of each active ingredient up to 1000 mg per day. In some embodiments, the compound of structure (I), or a pharmaceutically acceptable salt thereof, will be administered for a period of continuous therapy, for example for a week or more, or for months or years.

In some embodiments, the dosing regimen of the compound of structure (I), or a pharmaceutically acceptable salt thereof, is administered for a period of time, which time period can be, for example, from at least about 4 weeks to at least about 8 weeks, from at least about 4 weeks to at least about 12 weeks, from at least about 4 weeks to at least about 16 weeks, or longer. The dosing regimen of the compound of structure (I), or pharmaceutically acceptable salt thereof, can be administered three times a day, twice a day, daily, every other day, three times a week, every other week, three times per month, once monthly, substantially continuously, or continuously.

In cases of local administration or selective uptake, the effective local concentration of the drug may not be related to plasma concentration. The amount of composition administered may be dependent on the subject being treated, on the subject's weight, the severity of the affliction, and the manner of administration.

In some embodiments, the present disclosure relates to a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage of the compound of structure (I) or pharmaceutically acceptable salt thereof containing an amount of about 10 mg to about 1000 mg, of drug per dose, orally, at a frequency of three times per month, once monthly, once weekly, once every three days, once every two days, once per day, twice per day, three times per day, substantially continuously, or continuously, for the desired duration of treatment.

In some embodiments, the present disclosure provides a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage containing an amount of about 100 mg to about 1000 mg, of drug per dose, orally, at a frequency of three times per month, once monthly, once weekly, once every three days, once every two days, once per day, twice per day, or three times per day, for the desired duration of treatment.

In some further embodiments, the present disclosure provides a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage containing an amount of about 200 mg of drug per dose, orally, at a frequency of three times per month, once monthly, once weekly, once every three days, once every two days, once per day, twice per day, or three times per day, for the desired duration of treatment.

In some embodiments, the present disclosure provides a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage containing an amount of about 400 mg of drug per dose, orally, at a frequency of three times per month, once monthly, once weekly, once every three days, once every two days, once per day, twice per day, or three times per day, for the desired duration of treatment.

In some embodiments, the present disclosure provides a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage containing an amount of about 800 mg of drug per dose, orally, at a frequency of three times per month, once monthly, once weekly, once every three days, once every two days, once per day, twice per day, or three times per day, for the desired duration of treatment.

In some embodiments, the present disclosure provides a method of using the compound of structure (I) or pharmaceutically acceptable salt thereof in the treatment of a disease (e.g., Alport syndrome; hearing loss in a subject having Alport syndrome; hearing loss in a subject having diabetes; hearing loss in a subject having a mutation in a COL4A3, COL4A4, or COL4A5 gene; a collagen Type IV deficiency) in a patient comprising administering to the patient a dosage from about 0.1 mg/kg to about 100 mg/kg, or from about 0.2 mg/kg to about 50 mg/kg, or from about 0.5 mg/kg to about 25 mg/kg of body weight (or from about 1 mg to about 2500 mg, or from about 100 mg to about 800 mg) of active compound per day, which may be administered in a single dose or in the form of individual divided doses, such as from 1 to 4 times per day. In some embodiments, the amount of the compound of structure (I) or pharmaceutically acceptable salt thereof administered to the patient is from about 1 mg/kg to about 15 mg/kg, from about 3 mg/kg to about 12 mg/kg, or from about 3 mg/kg to about 6 mg/kg, per day, which may be administered in a single dose or in the form of individual divided doses, such as from 1 to 4 times per day.

In some embodiments of the aforementioned pharmaceutical compositions and methods, the pharmaceutical composition is a liquid formulation for oral administration. In some particular embodiments, the liquid formulation is administered to a subject who is 18 years old or younger, 12 years old or younger, from 6 to 12 years of age, or from 2 to 6 years of age.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound of structure (I), or pharmaceutically acceptable salt thereof, formulated in a compatible pharmaceutical carrier may also be prepared, placed in an appropriate container, and labeled for treatment of an indicated condition.

EXAMPLES

Example 1

Sparsentan Slows Renal Disease, Improves Lifespan, and Prevents Noise-Induced Hearing Loss in COL4A3$^{-/-}$ Autosomal Alport Mice The effect of dual AT1/ETA inhibition with sparsentan on nephropathy and hearing was evaluated in a murine model of Alport syndrome.

In Alport syndrome, $ET_AR$ activation in mesangial cells results in sub-endothelial invasion of glomerular capillaries by mesangial filopodia and induction of inflammatory cytokines culminating in glomerulosclerosis (GS) and tubulointerstitial fibrosis (TIF). Hearing loss in Alport syndrome is also a consequence of $ET_AR$-mediated changes in the inner ear. The effect of sparsentan on the development of nephropathy, inner ear pathology, and hearing loss following noise exposure was assessed in Alport mice and compared with that of the $AT_1R$ blocker losartan.

Methods

Vehicle or sparsentan was given daily by oral gavage to autosomal Alport mice (COL4A3$^{-/-}$) on the 129/Sv background (male and female) in five separate studies: a pilot study, an early intervention study (treated from 3-7 weeks of age), a late intervention study (treated from 5-7 weeks of age after the onset of glomerular (GM) changes), a lifespan study, and a hearing study (FIG. 1). The early intervention, late intervention, lifespan, and hearing studies also included mice treated with a comparator, losartan, which was given orally at 3-4 weeks of age in the early intervention study, in drinking water at 4-7 weeks of age in the early intervention study, and in drinking water at 5-7 weeks in the late intervention study.

Losartan is an angiotensin II receptor type 1 ($AT_1$) antagonist having the following structure:

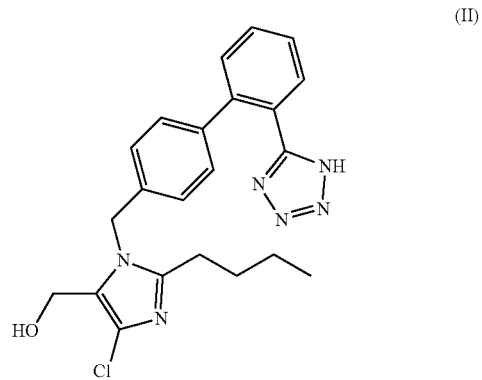 [SMILES: CCCCc1nc(Cl)c(CO)n1Cc1ccc(-c2ccccc2-c2nnn[nH]2)cc1]

(II)

Efficacy renal endpoints included blood urea nitrogen (BUN), proteinuria (urine protein to creatinine ratio, or UP/C), glomerulosclerosis, tubulointerstitial fibrosis, leucocyte infiltration, and glomerular basement morphology (GBM) using transmission electron microscopy (TEM). Endpoints in the inner ear included auditory brain stem response (ABR) threshold as a measure of noise-induced hearing loss, strial capillary basement membrane thickness, and inner ear pathology by TEM.

Figure 2A:
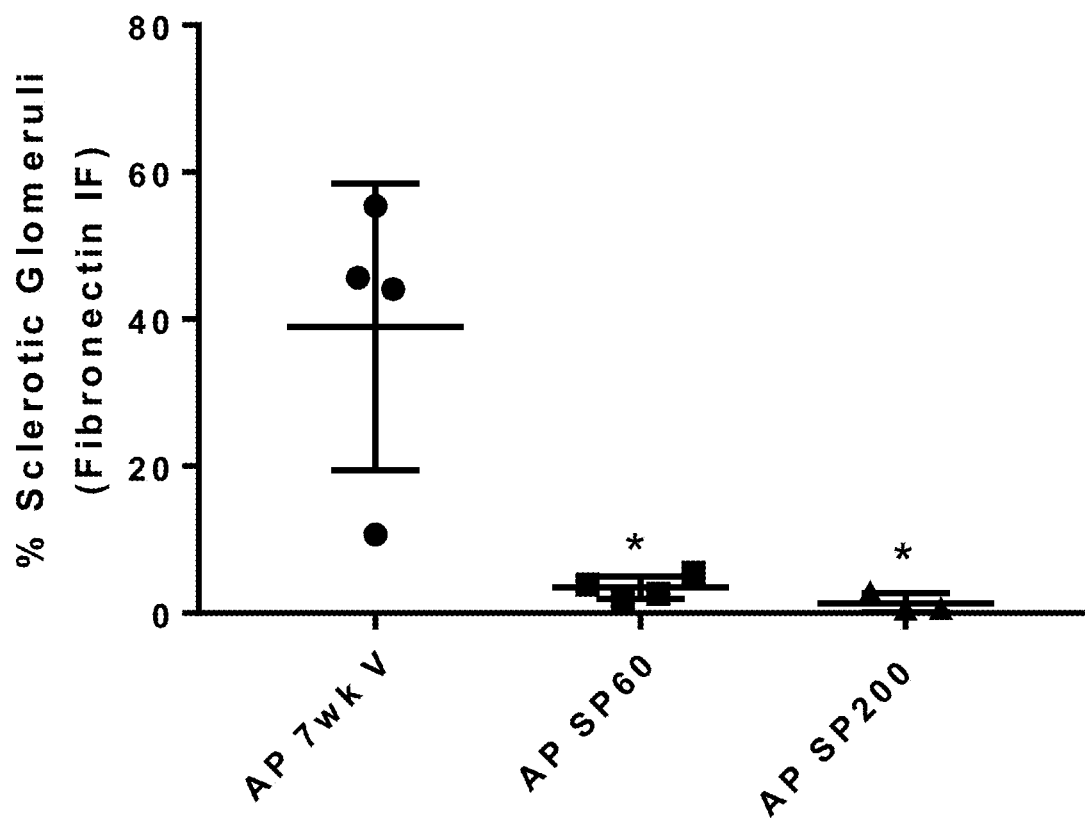
FIG. 2A. Effects of sparsentan on glomerulosclerosis in Alport mice observed during the pilot study. Data are shown for individual mice, with bars indicating group mean±SD. *P<0.05 vs vehicle. AP 7 wk V=Alport mice administered vehicle; AP SP60=Alport mice administered sparsentan at 60 mg/kg; AP SP200=Alport mice administered sparsentan at 200 mg/kg. IF=immunofluorescence. Treatment with sparsentan prevented an increase in glomerulosclerosis in a dose-dependent manner in 7 week-old Alport mice dosed for 4 weeks beginning at 3 weeks of age.
Figure 2B:
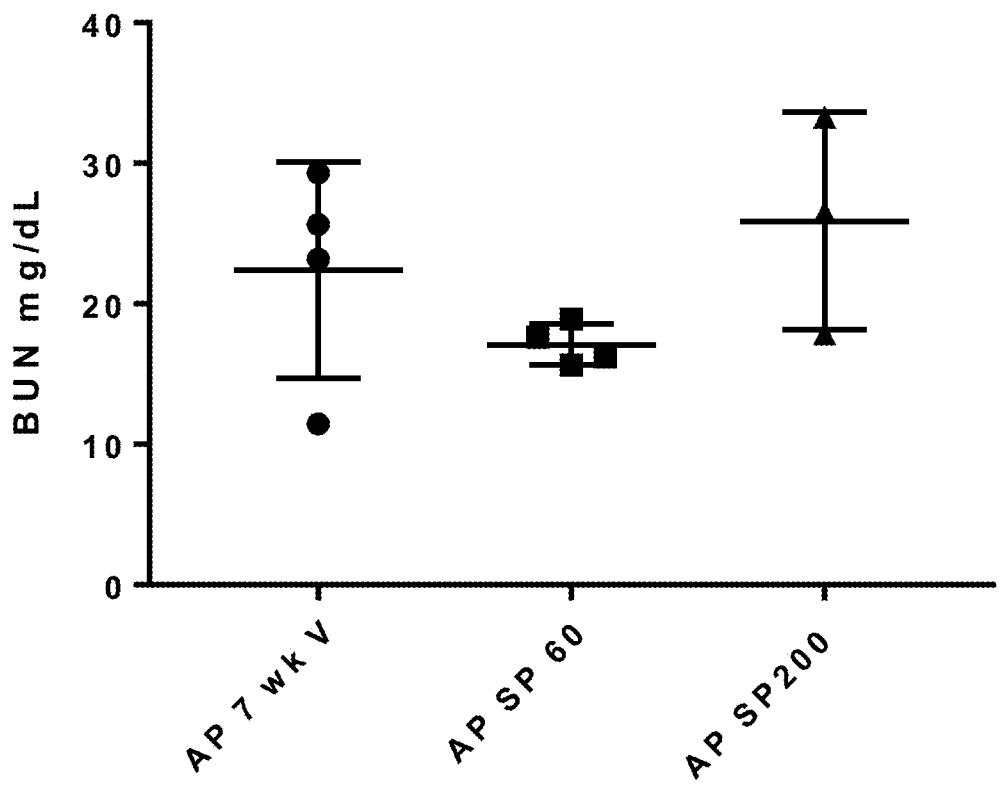
FIG. 2B. Effects of sparsentan on blood urea nitrogen (BUN) levels in Alport mice observed during the pilot study. Data are shown for individual mice, with bars indicating group mean±SD. *P<0.05 vs vehicle. AP 7 wk V=Alport mice administered vehicle; AP SP60=Alport mice administered sparsentan at 60 mg/kg; AP SP200=Alport mice administered sparsentan at 200 mg/kg. BUN levels in Alport mice at 7 weeks of age following 4 weeks of dosing.

In the pilot study, designed to determine an optimal efficacious dose of sparsentan, Alport mice (3-4 per group) were dosed with vehicle (0.5% methylcellulose 4000 cps/0.25% Tween® 80 in distilled water) or sparsentan at 60 mg/kg or 200 mg/kg from 3 to 7 weeks of age for 28 days. Although 200 mg/kg sparsentan was efficacious in the pilot study, BUN levels were higher than those of Alport mice dosed with 60 mg/kg sparsentan (Table 1; FIG. 2A; FIG. 2B). This observation led to the selection of a 120 mg/kg dose of sparsentan to take forward into the early intervention study. During the pilot study, blood pressure (BP) was measured weekly using the CODA2 tail cuff system. Stria from this pilot study were also examined by immunofluorescence using antibodies to laminin α2

In the early intervention study, wild-type and Alport mice were dosed daily by oral gavage with vehicle or sparsentan at 120 mg/kg from 3 to 7 weeks of age (7-8 mice per group), or with losartan at 20 mg/kg by oral gavage from 3-4 weeks of age (during weaning) and 10 mg/kg in drinking water from 4-7 weeks of age.

In the late intervention study, wild-type or Alport mice (8 mice per group) were dosed for 14 days according to the same methods used in the early intervention study but beginning at 5 weeks of age, i.e., dosed with vehicle, 120 mg/kg of sparsentan, or 10 mg/kg losartan starting at 5 weeks of age for 14 days. In this study, untreated Alport mice at 5 weeks of age were also used as baseline controls.

In the lifespan study, Alport mice (n=10) were dosed using the same methodology as in the early intervention study, except that dosing was continued until mice had lost 10% of their peak body weight, after which they were euthanized.

For the pilot, early intervention, late intervention, and lifespan studies, spot urine was sampled pre-study and weekly during treatment and analyzed for protein (UP) and creatinine (C) to determine proteinuria (UP/C). At the end of each study the animals were euthanized, blood samples were taken, BUN was measured from serum, and kidneys were harvested for structural and immuno-fluorescent measurements. Glomerulosclerosis was assessed by immunofluorescence (IF) using an antibody to fibronectin (FN). Visual counting of the number of sclerotic glomeruli as a proportion of the total number of glomeruli per slide was used to calculate the percentage of sclerotic glomeruli. Sections were co-stained with an anti-CD45 antibody to indicate leucocyte infiltration. Tubulointerstitial fibrosis was determined by IF of kidney sections using an antibody to collagen 1 (COL1). Tubulointerstitial fibrosis (TIF) scoring was conducted by visual assessment of the COL1 positive area as a percentage of the total cortical area and was performed blinded. The fibrosis scoring ("Fibrosis Score") was categorized according to visual judgment of percentage of total cortical area, as: 0=<5%, 1=5-10%, 2=10-25%, 3=25-50%, 4=50-75%, or 5=75-100%. Ultrastructural changes in GBM and podocyte morphology were observed using transmission electron microscopy (TEM).

For a baseline comparison for late intervention, glomerulosclerosis and fibrosis were determined in kidney samples taken from 5-week-old untreated Alport mice.

For the hearing study, wild-type or Alport mice were treated according to daily from 3-8.5 weeks of age by oral gavage with vehicle (0.5% methylcellulose 4000 cps/0.25% Tween® 80 in distilled water) or 120 mg/kg sparsentan or losartan at 20 mg/kg by oral gavage from 3-4 weeks of age (during weaning) and 10 mg/kg in drinking water from 4-7 weeks of age (n=5). The progression of Alport disease was assessed at 7 weeks of age by the amount of proteinuria (via urinalysis reagent strips—data not shown). Strial capillary basement membrane (SCBM) width was analyzed by transmission electron microscopy (TEM), and accumulation of extracellular matrix (ECM) in SCBM was determined by immunofluorescence (IF) microscopy using an antibody to laminin α2. Hearing ability and sensitivity to noise were assessed between 7 and 8 weeks of age by Auditory Brainstem Response (ABR), pre-noise exposure. A subset of each treatment group was then exposed to a metabolic noise stress for 10 hours. Mice receiving the noise treatment were randomly selected for overstimulation with a 106 dB sound pressure level (SPL), narrow band noise (8-16 kHz) for 10 hours, usually 10 PM to 8 AM. The noise exposure was conducted in a sound-isolation booth. A speaker was suspended from the ceiling. Wire cages with individual compartments were located midway between the floor and speaker. Mice were hydrated prior to placement in the cage and were provided free access to food. The noise exposure occurred at 8 weeks of age. The amount of hearing loss caused by the metabolic noise exposure was determined 5 days post-exposure.

P values are from one-way ANOVA pairwise comparison t-tests.

Results of Pilot Study

The results of the pilot dose-response study are shown in Table 1 and FIGS. 2A and 2B. The results demonstrated a dose-dependent prevention of UP/C, glomerulosclerosis, and fibrosis for sparsentan-treated mice compared to vehicle-treated mice.

TABLE 1

Pilot study dose-dependent effects of sparsentan in Alport mice treated from 3-7 weeks of age.

| Endpoint | | Alport - vehicle (n = 4) | Alport - sparsentan 60 mg/kg (n = 4) | Alport - sparsentan 200 mg/kg (n = 3) |
|---|---|---|---|---|
| SBP (mmHg) | 5 wk | 110.0 ± 7.3 | 114.0 ± 13.0 | 110.6 ± 21.8 |
| | 6 wk | 142.1 ± 13.5 | 106.2 ± 6.9* | 108.7 ± 26.4* |
| | 7 wk | 125.7 ± 6.0 | 117.6 ± 4.6 | 122 ± 20.9 |
| DBP (mm/Hg) | 5 wk | 76.0 ± 9.4 | 71.1 ± 10.7 | 99.7 ± 7.7* |
| | 6 wk | 95.7 ± 13.0 | 72.9 ± 9.6 | 74.6 ± 21.4 |
| | 7 wk | 85.2 ± 4.0 | 78.1 ± 14.7 | 91.7 ± 20.0 |
| BUN (mg/dL) | 7 wk | 22.4 ± 7.7 | 17.1 ± 1.5 | 25.9 ± 7.7 |
| UP/C (mg/mg) | 4 wk | 3.6 ± 3.0 | 3.4 ± 2.6 | 2.1 ± 3.7 |
| | 5 wk | 9.3 ± 3.0 | 8.6 ± 2.4 | 3.9 ± 3.5* |
| | 6 wk | 22.6 ± 13.4 | 1.5 ± 1.5* | 1.5 ± 2.7 |
| | 7 wk | 34.1 ± 17.4 | 5.6 ± 3.0* | 0.8 ± 1.4* |
| Sclerotic Glomeruli (%) | 7 wk | 39 ± 19.5 | 3.5 ± 1.6* | 1.4 ± 1.3* |
| Fibrosis Score | 7 wk | 2.5 ± 0.6 | 0.0 ± 0.0* | 0.0 ± 0.0* |

Values ± SD;
*$P < 0.05$ vs. Vehicle.
Comparison of active dose to vehicle using t-test from one-way ANOVA for all parameters except fibrosis score; for fibrosis score, comparison of active dose to vehicle using Fisher's exact test.

Systolic blood pressure (SBP) and diastolic blood pressure (DBP) were significantly lower for Alport mice treated with 60 or 200 mg/kg of sparsentan compared to Alport mice provided vehicle at 6 weeks of age (3 weeks of dosing), while no difference in BP was observed between sparsentan-treated Alport mice and vehicle-treated Alport mice at the end of the pilot study (7 weeks of age; 4 weeks of dosing) (Table 1). Sparsentan led to significantly lower UP/C (60 mg/kg: 5.6±3.0 mg/mg, n=4, P<0.05; 200 mg/kg: 0.8±1.4 mg/mg, n=3, P<0.01) compared to vehicle-treated Alport mice (34.1±17.4 mg/mg, n=4) (Table 1). The percentage of sclerotic glomeruli, determined from fibronectin IHC, was lower (P<0.01) in Alport mice that received sparsentan at 60 mg/kg (3.5±1.6%, n=4) or 200 mg/kg (1.4±1.3%, n=3) compared with vehicle-treated Alport mice (39.0±19.5%, n=4) (Table 1; FIG. 2A). COL1 immunoreactivity was absent in sparsentan-treated Alport mice, similar to wild-type mice. In contrast, vehicle-treated Alport mice had COL1 score of 2.5±0.6 (arbitrary units).

Because BUN levels were elevated following dosing with 200 mg/kg of sparsentan compared to that following dosing with 60 mg/kg sparsentan (FIG. 2B), 120 mg/kg was selected as a dose for the intervention studies.

Results of Early Intervention Study

Figure 3:
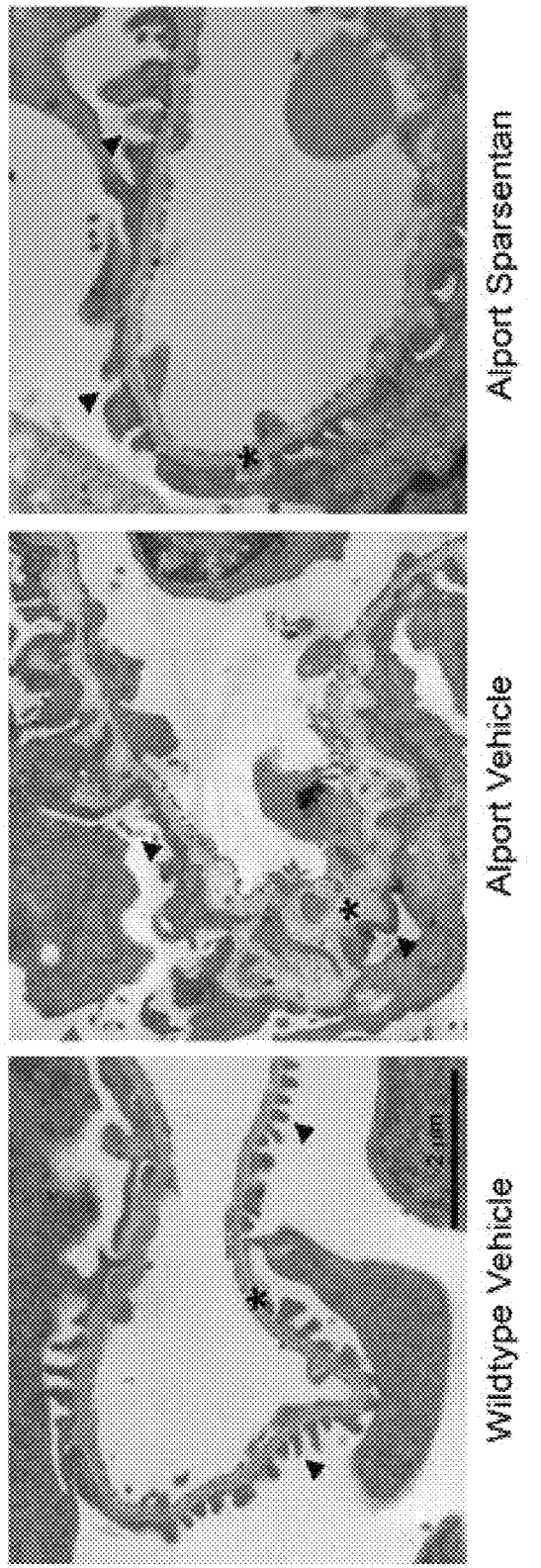
FIG. 3. Transmission electron microscopy images of glomeruli in vehicle-treated wild-type mice (left), vehicle-treated Alport mice (middle), and Alport mice treated with 120 mg/kg of sparsentan (right), in the early intervention study. Sparsentan treatment of Alport mice prevented changes in GBM ultrastructural morphology (indicated by *) and reduced podocyte effacement (indicated by arrows).

In the early intervention study, administration of sparsentan or losartan prevented development of nephropathy in Alport mice. Treatment with sparsentan at 120 mg/kg for 28 days or losartan (7 days 20 mg/kg oral, 21 days 10 mg/kg drinking water) beginning at 3 weeks of age resulted in significant attenuation in UP/C, BUN, glomerulosclerosis, and fibrosis in Alport mice (P<0.05 vs. vehicle-treated Alport mice) (Table 2). Sparsentan-treated Alport mice and losartan-treated Alport mice showed little to no TIF or glomerulosclerosis. Treatment with sparsentan was also associated with amelioration of GBM damage and podocyte effacement in Alport mice (FIG. 3).

TABLE 2

Effects of sparsentan in Alport mice in the early intervention study.

| Endpoint | | Wild-type - vehicle (n = 8) | Alport - vehicle (n = 8) | Alport - sparsentan 120 mg/kg (n = 8) | Alport- losartan 20/10 mg/kg (n = 8) |
|---|---|---|---|---|---|
| UP/C | 4 wk | 3.1 ± 2.7 | 2.9 ± 1.8 | 3.8 ± 1.3 | 0.6 ± 1.3* |
| (mg/mg) | 5 wk | 5.7 ± 2.6 | 9.6 ± 5.9 | 10.4 ± 2.8 | 6.7 ± 4.0 |
| | 6 wk | 8.5 ± 6.8 | 17.0 ± 8.3 | 13.6 ± 3.7 | 11.2 ± 5.7 |
| | 7 wk | 8.3 ± 2.2 | 24.4 ± 8.1 | 14.0 ± 3.3* | 11.5 ± 7.0* |
| BUN (mg/dL) | 7 wk | 17.5 ± 5.3 | 19.3 ± 4.5 | 17.5 ± 3.3 | 18.2 ± 3.5 |
| Sclerotic Glomeruli (%) | 7 wk | 0.0 ± 0.0 | 34.9 ± 19.4 | 0.8 ± 1.7* | 1.7 ± 3.3* |
| Fibrosis Score | 7 wk | 0.0 ± 0.0 | 2.6 ± 0.7 | 0.0 ± 0.0* | 0.0 ± 0.0* |

Values ± SD;
*P < 0.05 vs. Vehicle.
Comparison of active dose to Alport vehicle using t-test from one-way ANOVA for all parameters except fibrosis score; for fibrosis score, comparison of active dose to vehicle using Fisher's exact test.

Results of Late Intervention Study

Figure 4A:
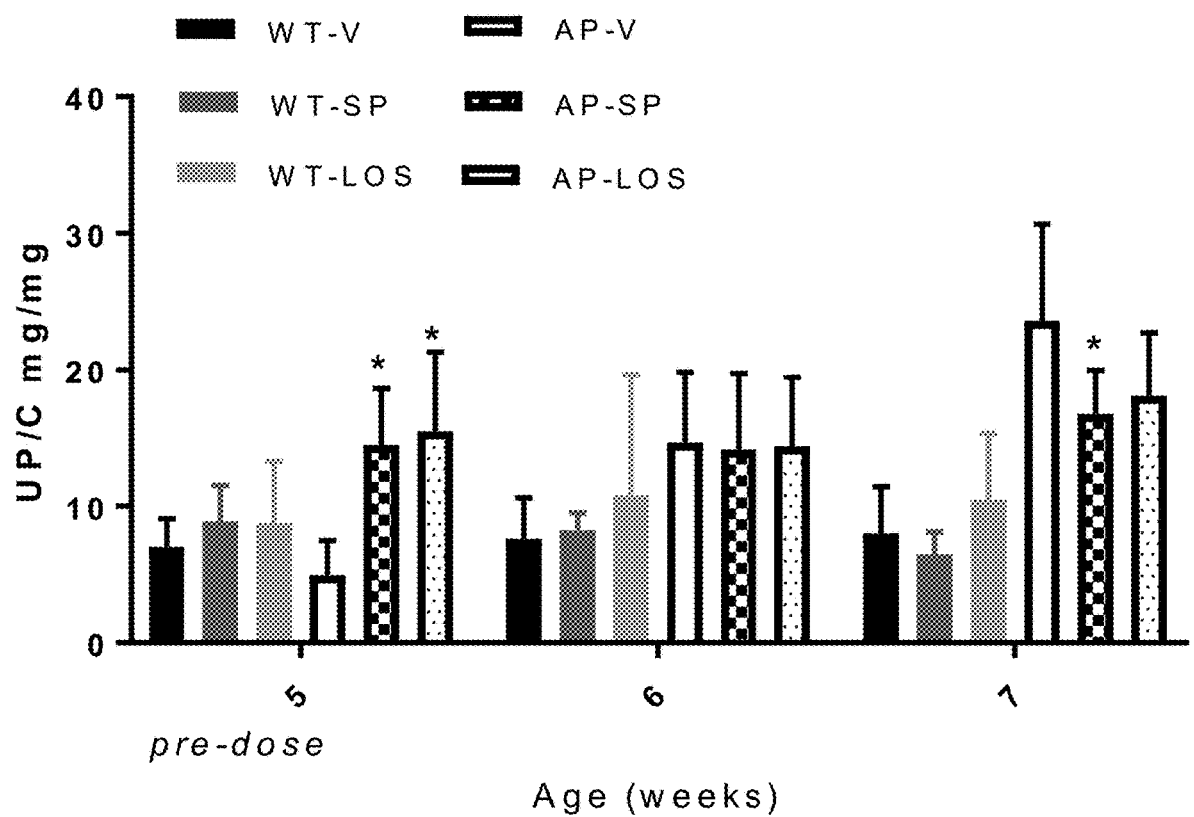
FIG. 4A. Effects of sparsentan and losartan on proteinuria (UP/C levels, mg/mg) observed during the late intervention study in wild-type mice treated with vehicle (WT-V), 120 mg/kg sparsentan (WT-SP) or 10 mg/kg losartan (WT-LOS) or Alport mice treated with vehicle (AP-V), or Alport mice treated with 120 mg/kg sparsentan (AP-SP) or 10 mg/kg losartan (AP-LOS) for 14 days starting at 5 weeks of age. Data are shown from individual mice with bars indicating group mean±SD. *P<0.05 Alport mice treated with 120 mg/kg sparsentan (APSP) or 10 mg/kg losartan (AP-LOS) vs. Alport mice treated with vehicle (AP-V).
Figure 4B:
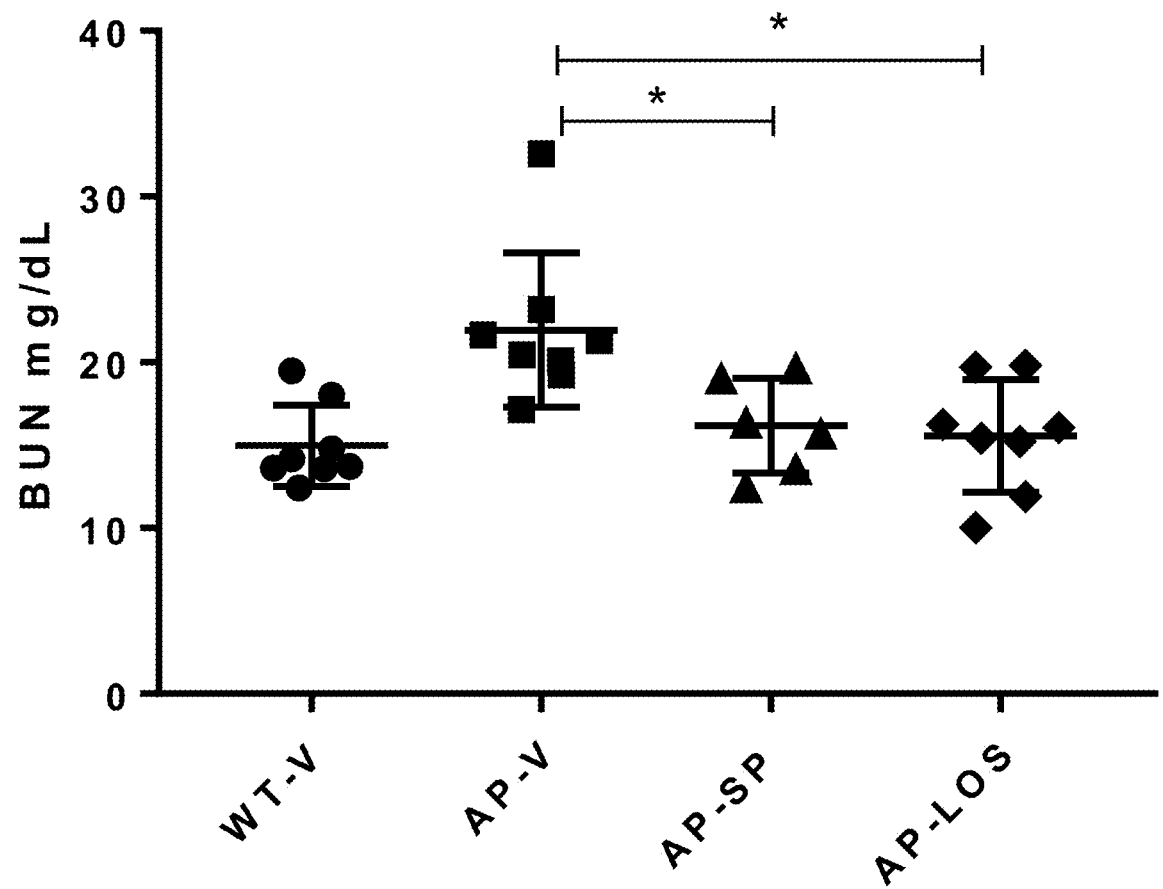
FIG. 4B. Effects of sparsentan and losartan on blood urea nitrogen (BUN) levels (mg/dL) observed during the late intervention study in wild-type mice treated with vehicle (WT-V), Alport mice treated with vehicle (AP-V), Alport mice treated with 120 mg/kg sparsentan (AP-SP) or 10 mg/kg losartan (AP-LOS) for 14 days starting at 5 weeks of age. Data are shown from individual mice with bars indicating group mean±SD. *P<0.05 Alport mice treated with 120 mg/kg sparsentan (AP-SP) vs. Alport mice treated with vehicle (AP-V) or Alport mice treated with 10 mg/kg losartan (AP-LOS).
Figure 5A:
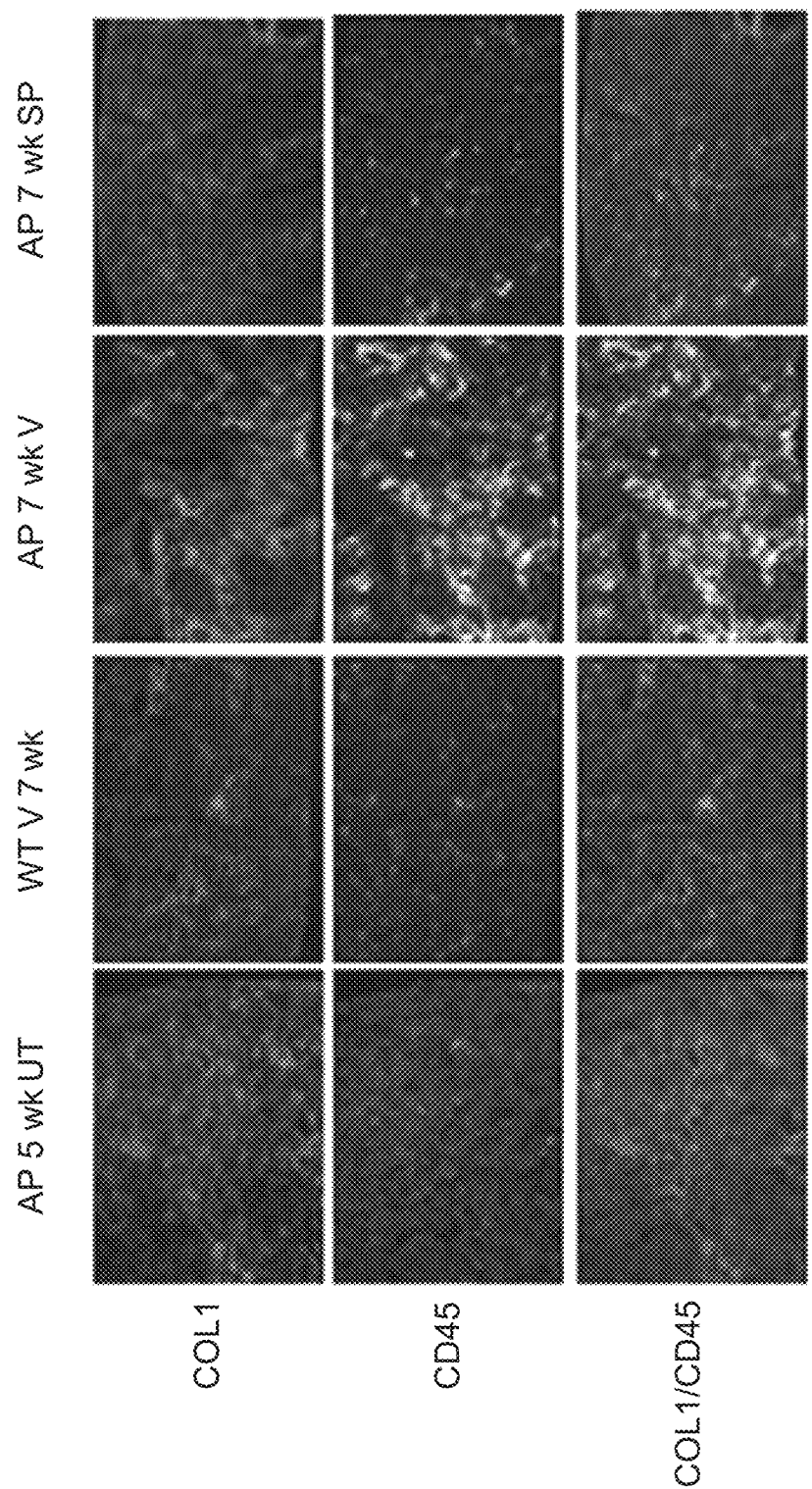
FIG. 5A. Sparsentan prevented the increase in interstitial fibrosis and CD45[+] leucocyte infiltration in Alport mice dosed for 2 weeks from 5 weeks of age to 7 weeks of age. Cortical sections from untreated Alport mice at 5 weeks (AP 5 wk UT); 7-week-old wild-type mice treated with vehicle (WT V 7 wk); 7-week-old Alport mice treated with vehicle (AP 7 wk V); and 7-week-old Alport mice treated with 120 mg/kg sparsentan (AP 7 wk SP), stained with anti-COL1 antibodies (red; upper panel and lower panel) and anti-CD45 antibodies (green; middle panel and lower panel). Images were taken with a Zeiss fluorescence microscope at 200× magnification. Cortical sections from sparsentan-treated Alport mice showed reduced fluorescence following staining with anti-COL1 antibodies (red) and anti-CD45 antibodies (green).
Figure 5B:
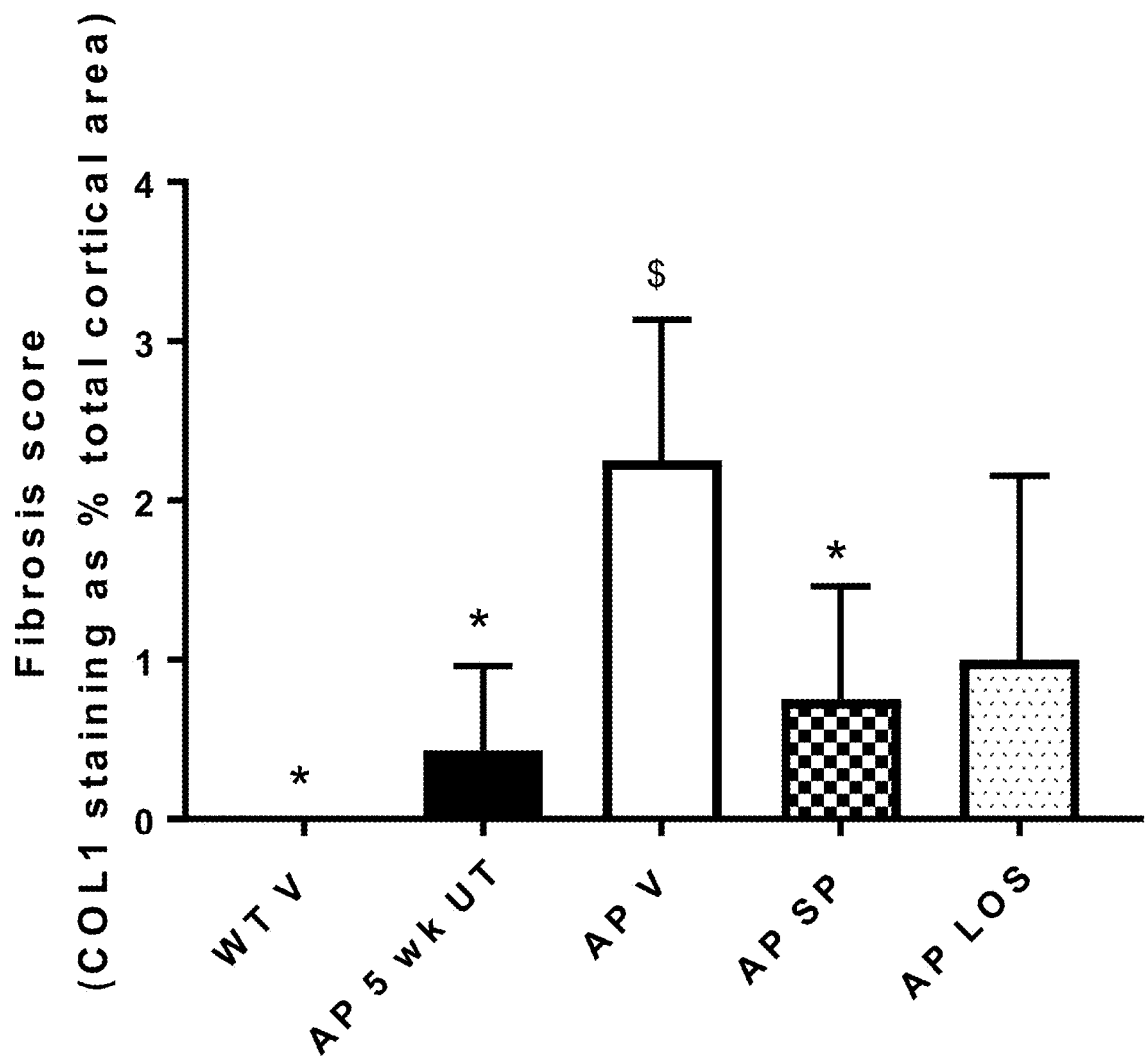
FIG. 5B. The percent area staining for COL1 in the cortical sections, for 7-week-old wild-type mice treated with vehicle (WT V), untreated Alport mice at 5 weeks (AP 5 wk UT), 7-week-old Alport mice treated with vehicle (AP V), 7-week-old Alport mice treated with 120 mg/kg sparsentan (AP SP), and 7-week-old Alport mice treated with 10 mg/kg losartan (AP LOS). *P<0.05 vs AP V; $P<0.05 vs AP 5 wk UT.
Figure 6A:
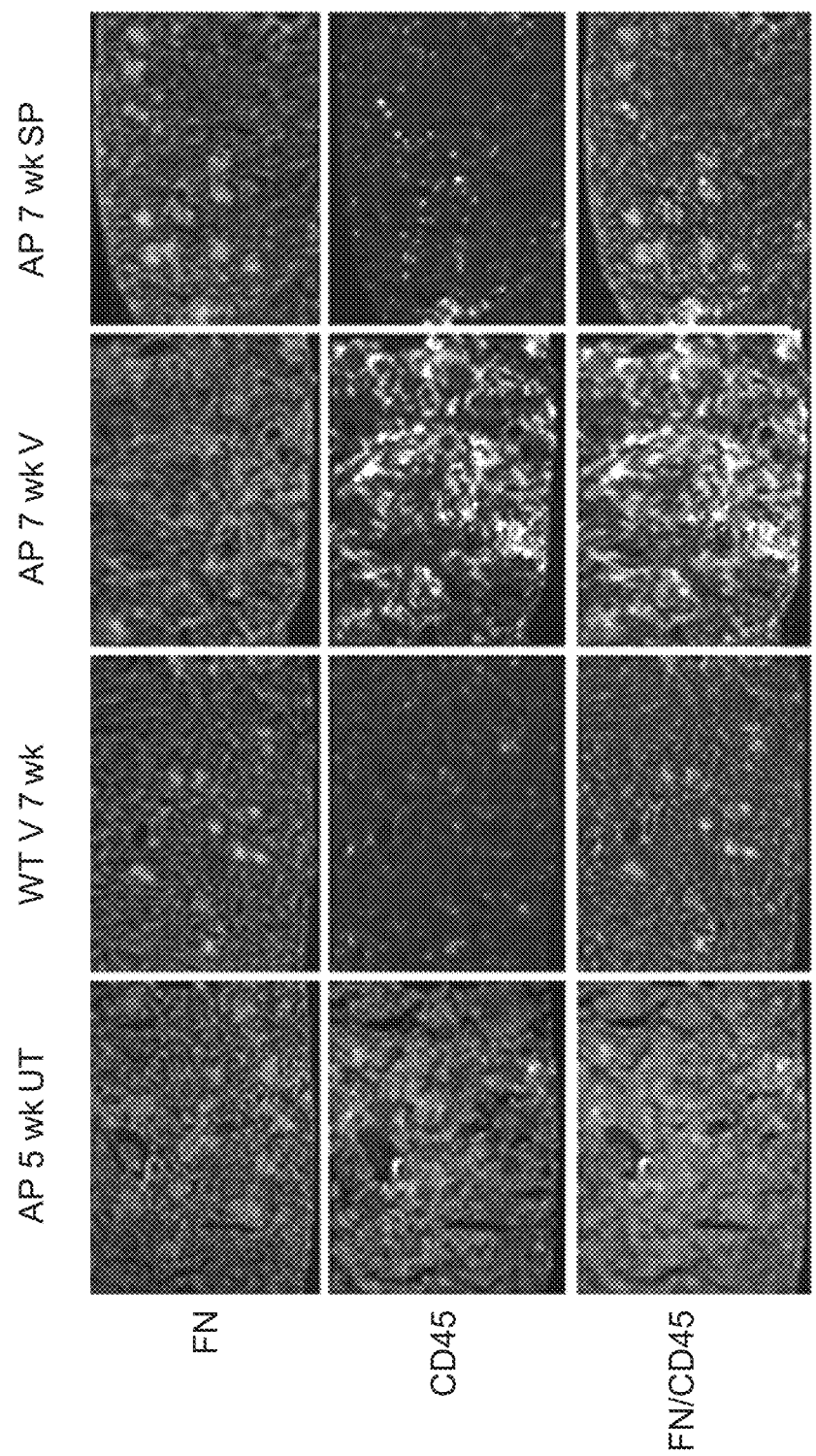
FIG. 6A. Sparsentan prevented an increase in the relative amount of sclerotic glomeruli in Alport mice dosed for 2 weeks from 5 weeks of age to 7 weeks of age. Cortical sections from untreated Alport mice at 5 weeks (AP 5 wk UT); 7-week-old wild-type mice treated with vehicle (WT V 7 wk); 7-week-old Alport mice treated with vehicle (AP 7 wk V); and 7-week-old Alport mice treated with 120 mg/kg sparsentan (AP 7 wk SP), stained with anti-fibronectin antibodies (red; upper panel and lower panel) and anti-CD45 antibodies (green; middle panel and lower panel). Images were taken with a Zeiss fluorescence microscope at 200× magnification and are from sections from the same animals as in FIG. 5A. Kidney sections from sparsentan-treated Alport mice showed reduced fluorescence in glomeruli following co-staining with antibodies to fibronectin (FN) (red) and CD45 (green).
Figure 6B:
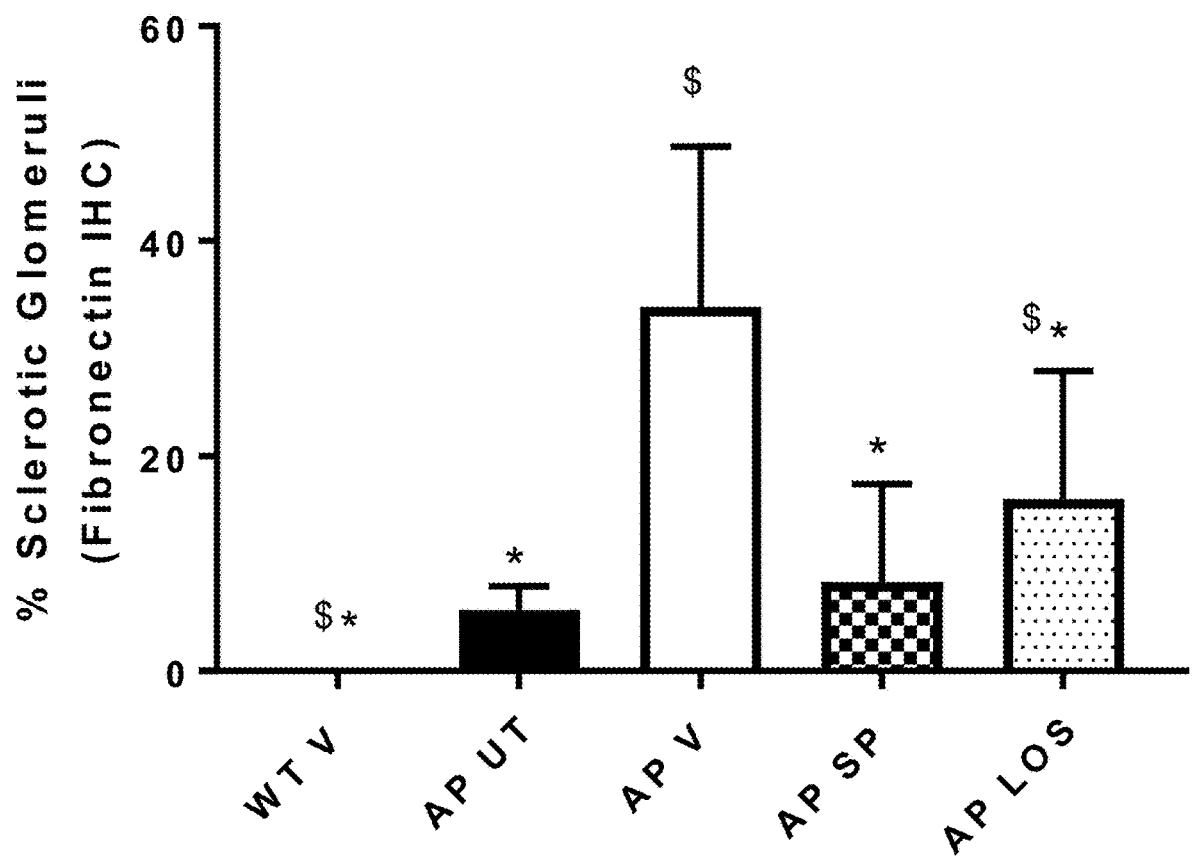
FIG. 6B. Sparsentan and losartan prevented an increase in the relative amount of sclerotic glomeruli in Alport mice dosed for 2 weeks from 5 weeks of age to 7 weeks of age. The percentage of sclerotic glomeruli in sparsentan-treated Alport mice dosed for 2 weeks from 5 weeks of age to 7 weeks of age was significantly decreased compared to that in vehicle treated mice following visual assessment. Shown are values for 7-week-old wild-type mice treated with vehicle (WT V), untreated Alport mice at 5 weeks (AP UT), 7-week-old Alport mice treated with vehicle (AP V), 7-week-old Alport mice treated with 120 mg/kg sparsentan (AP SP), and 7-week old Alport mice treated with 10 mg/kg losartan (AP LOS). *$P<0.05$ vs. AP V; $$P<0.05$ vs AP UT.

The effects on renal function of administering sparsentan at 120 mg/kg or losartan at 10 mg/kg to Alport mice during the late intervention study are shown in FIGS. 4A, 4B, 5A, 5B, 6A, and 6B and Table 3. Sparsentan and losartan treatment attenuated the level of UP/C and BUN in Alport mice relative to treatment with vehicle (FIGS. 4A, 4B). Treatment with sparsentan or losartan also attenuated the development of fibrosis (FIGS. 5A, 5B), CD45+ leucocyte infiltration (FIGS. 5A and 6A), and glomerulosclerosis (FIGS. 6A and 6B). The UP/C, BUN, glomerulosclerosis, and fibrosis in sparsentan-treated Alport mice were significantly lower than in vehicle-treated Alport mice (P<0.05). For losartan, the attenuation of BUN and glomerulosclerosis was significant compared to vehicle-treated Alport mice (P<0.05) but UP/C and fibrosis were not significant compared to Alport mice treated with vehicle in the late intervention studies.

Results of Hearing Study

Figure 8A:
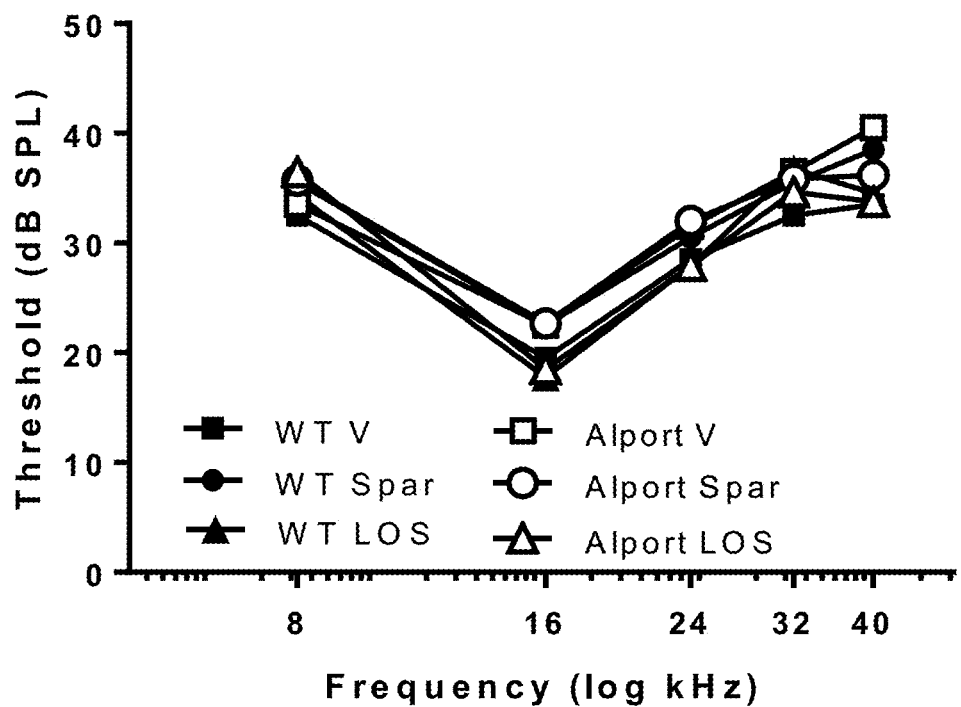
FIG. 8A. Hearing ability determined by auditory brainstem response (ABR) before noise exposure, in vehicle-treated wild-type mice (WT V), sparsentan-treated WT wild-type mice (WT Spar), losartan-treated wild-type mice (WT LOS), vehicle-treated Alport mice (Alport V), sparsentan-treated Alport mice (Alport Spar), and losartan-treated Alport mice (Alport LOS). Hearing ability before noise was within the normal range for 7-8-week-old 129/Sv wild-type mice and did not differ significantly from Alport mice or following sparsentan or losartan treatment. Means are shown. dB=decibels; SPL=sound pressure level.
Figure 8B:
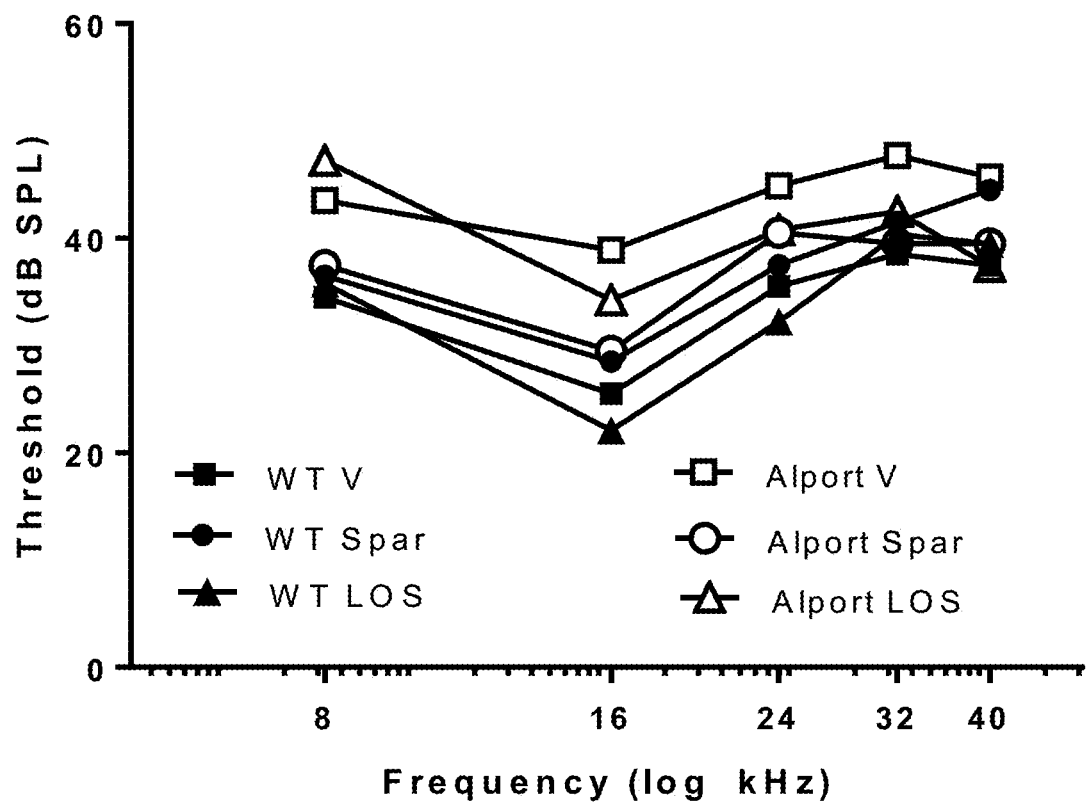
FIG. 8B. Hearing ability determined by auditory brainstem response (ABR) 5 days after noise exposure, in vehicle-treated wild-type mice (WT V), sparsentan-treated WT wild-type mice (WT Spar), losartan-treated wild-type mice (WT LOS), vehicle-treated Alport mice (Alport V), sparsentan-treated Alport mice (Alport Spar), and losartan-treated Alport mice (Alport LOS). Means are shown. dB=decibels; SPL=sound pressure level.
Figure 9A:
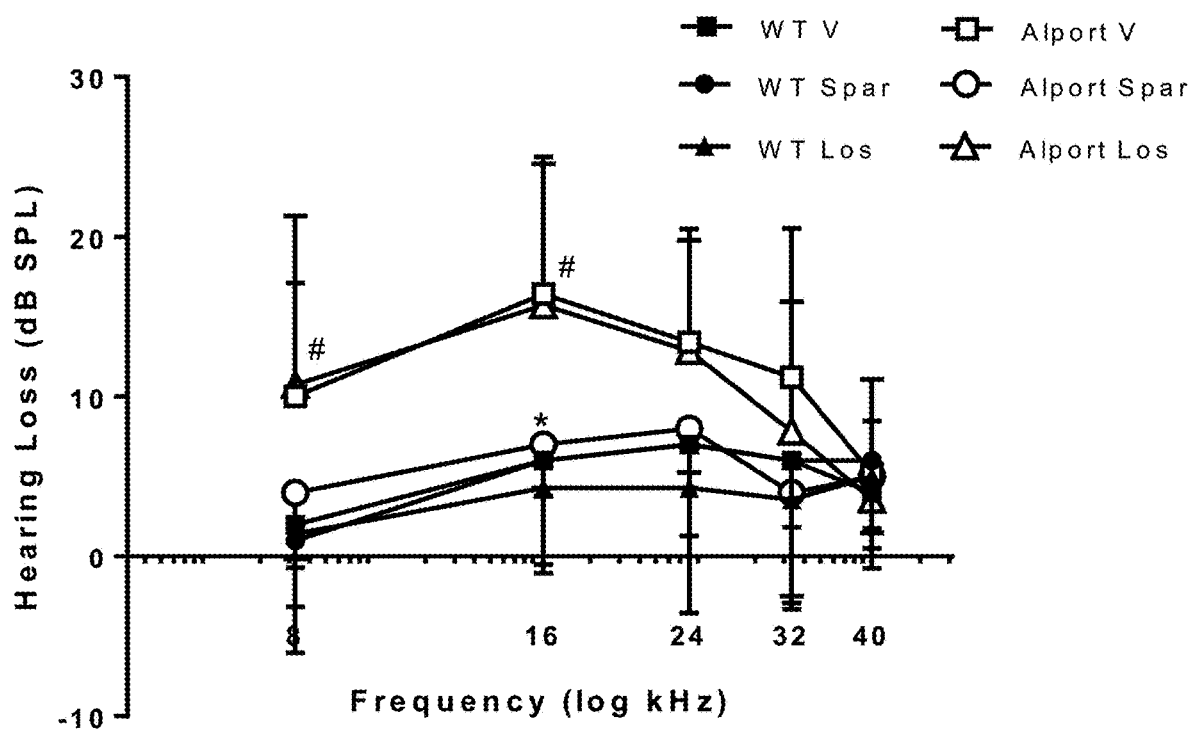
FIG. 9A. Sparsentan but not losartan prevented noise-induced hearing loss. Hearing loss derived from ABR thresholds shown in FIGS. 8A and 8B (calculated as threshold post-noise minus threshold pre-noise), in vehicle-treated wild-type mice (WT V), sparsentan-treated wild-type mice (WT Spar), losartan-treated wild-type mice (WT Los), vehicle-treated Alport mice (Alport V), sparsentan-treated Alport mice (Alport Spar), and losartan-treated Alport mice (Alport Los). Hearing loss across frequencies tested; data presented as means+SD (Alport V and Alport Los) or –SD for WT V, WT Spar, WT Los and Alport Spar for clarity (n=5-6). The Alport vehicle-treated group incurred a mild hearing loss in the low-mid frequencies (8-24 kHz), which was significant compared to the vehicle-treated wild-type mice at 8 kHz and 16 kHz. The hearing loss in the Alport sparsentan-treated group was significantly reduced compared to that of the Alport vehicle-treated group at the 16 kHz frequency. There was no significant difference between hearing loss in the Alport vehicle-treated group and the Alport losartan-treated group at any frequency tested. #$P<0.05$ Alport V compared to WT V; * $P<0.05$ Alport V compared to Alport Spar.

Hearing ability before noise exposure was within the normal range for 7-8-week-old 129/Sv wild-type mice and did not differ significantly from the Alport mice or following sparsentan or losartan treatment (FIG. 8A). After noise exposure (FIG. 8B), the vehicle-treated Alport mice incurred a mild hearing loss (calculated from ABR threshold post-noise minus that pre-noise) in the low-mid frequencies (8-24 kHz), the frequencies predicted to be most affected by the noise parameters, and the hearing loss was significantly different compared to the vehicle-treated wild-type mice at 8 kHz and 16 kHz (P<0.05) (FIG. 9A). Sparsentan prevented the post-noise hearing loss observed in vehicle-treated

TABLE 3

Effects of sparsentan and losartan following late intervention treatment in Alport mice.

| Endpoint | WT LI Vehicle (n = 8) | AP 5 week untreated (n = 8) | AP LI Vehicle (n = 8) | AP LI Sparsentan (120 mg/kg) (n = 8) | AP LI Losartan (10 mg/kg) (n = 8) |
|---|---|---|---|---|---|
| UP/C, mg/mg | 8.0 ± 3.4* | ND | 23.6 ± 7.1 | 16.8 ± 2.8* | 18.1 ± 4.6 |
| BUN, mg/dL | 15.0 ± 2.5* | ND | 22.0 ± 4.7 | 16.2 ± 2.4* | 15.5 ± 3.4* |
| GS (% Sclerotic glomeruli) | 0.0 ± 0.0*$ | 5.7 ± 2.2* | 33.9 ± 15.0$ | 8.3 ± 9.2* | 16.0 ± 11.9*$ |
| TIF | 0.0 ± 0.0* | 0.4 ± 0.5* | 2.3 ± 0.9$ | 0.8 ± 0.7* | 1.0 ± 1.2 |

Data are presented as mean ± SD.
*P < 0.05 vs Alport vehicle;
$P < 0.05 vs untreated AP 5 week.
BUN = blood urea nitrogen; GS = glomerulosclerosis; ND = not determined; TIF = tubulointerstitial fibrosis; UP/C = urinary protein-to-creatinine ratio.

These results indicate that in the late intervention studies, sparsentan provided significant nephroprotection in AP mice, and to a greater extent than in the losartan-treated group.

Results of Lifespan Study

Figure 7:
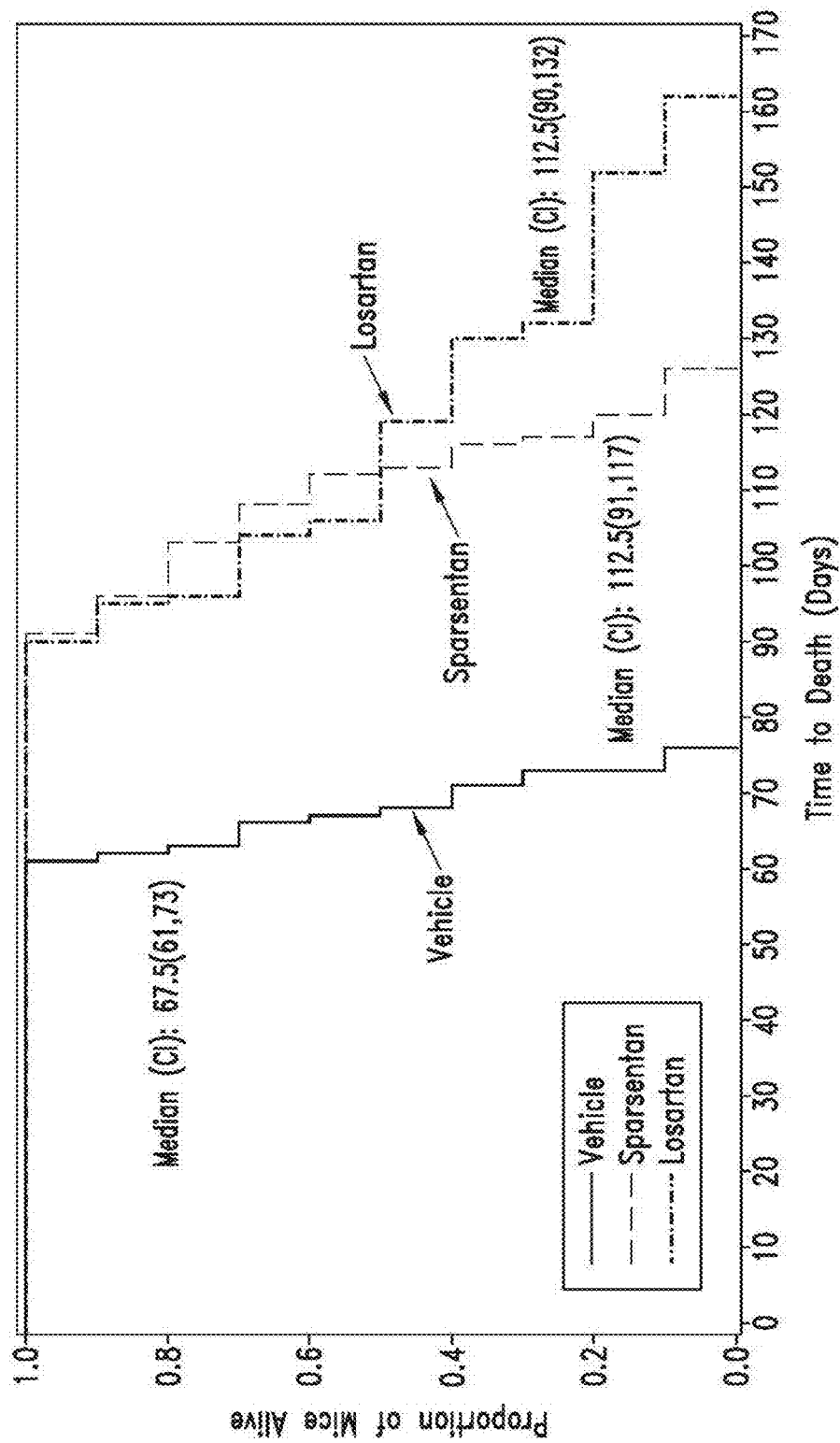
FIG. 7. Lifespan of Alport mice in days, displayed as a Kaplan-Meier plot. The median lifespan of mice treated with sparsentan or losartan was not different but were both significantly greater than that of vehicle-treated mice.

Lifespan was significantly longer (P<0.05) for both sparsentan- and losartan-treated AP mice compared to APV (FIG. 7), with median lifespan for sparsentan the same as losartan. It is currently unclear whether starting dosing sparsentan in mice at 3 weeks of age, when kidneys were not fully mature, may have affected lifespan and whether initiation of sparsentan dosing at an age when kidneys are mature could further lengthen lifespan. Endothelin-1 receptor antagonists, including sparsentan, are known to affect developing kidneys.

Figure 9B:
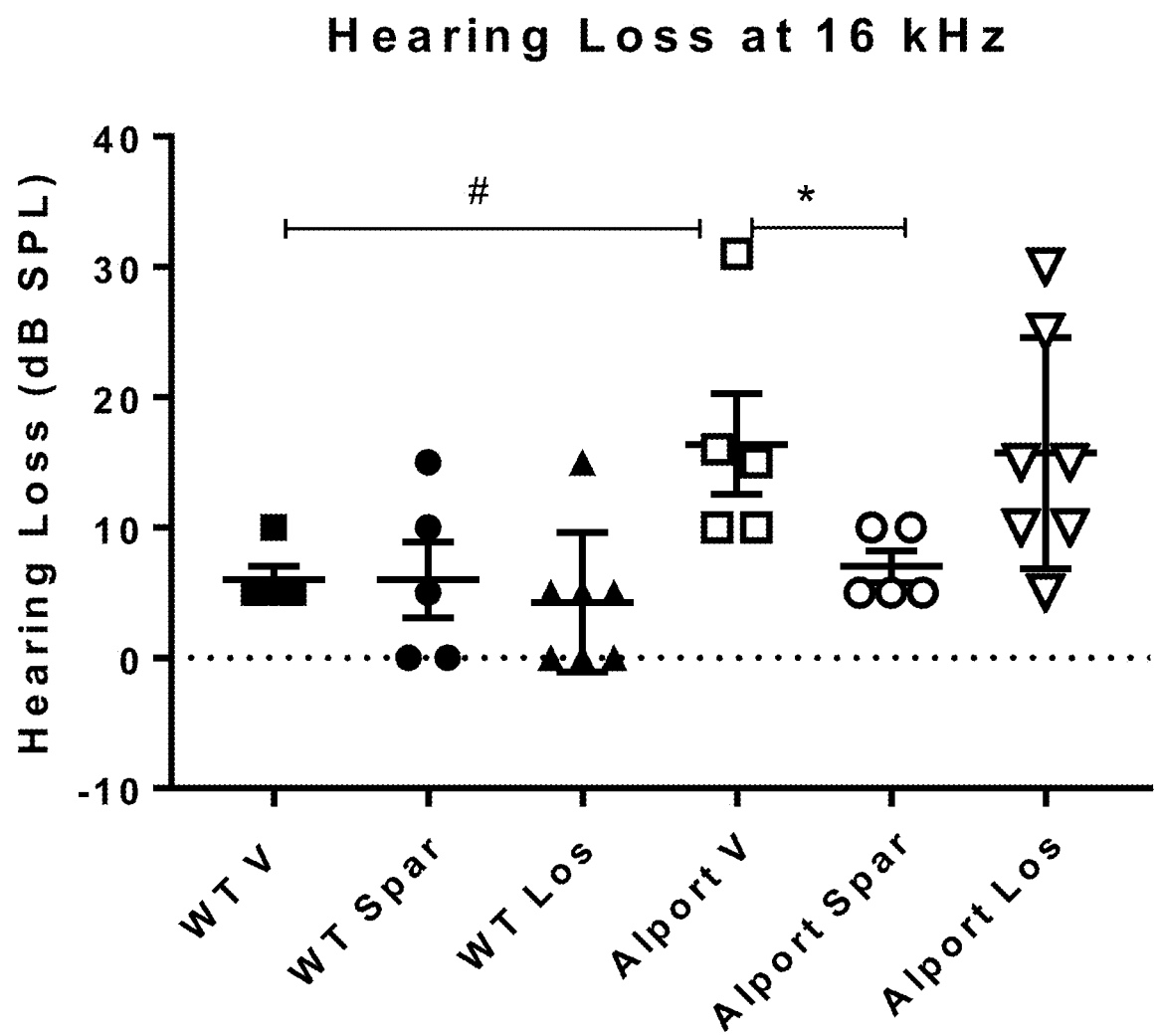
FIG. 9B. Sparsentan but not losartan prevented noise-induced hearing loss. Hearing loss derived from ABR thresholds shown in FIGS. 8A and 8B (calculated as threshold post-noise minus threshold pre-noise), in vehicle-treated wild-type mice (WT V), sparsentan-treated wild-type mice (WT Spar), losartan-treated wild-type mice (WT Los), vehicle-treated AP Alport mice (Alport PV), sparsentan-treated Alport mice (Alport Spar), and losartan-treated Alport mice (Alport Los). Data are shown from individual animals (n=5-6). Hearing loss at 16 kHz. *$P<0.05$ Alport Spar compared to Alport V; #$P<0.05$ Alport V compared to WT V. Alport mice treated with sparsentan did not exhibit the post-noise hearing loss observed in vehicle-treated Alport mice at 16 kHz (*$P<0.05$ Alport Spar vs. Alport V) and were not significantly different compared to vehicle-treated wild-type mice (NS Alport Spar vs. WT V). There was no significant difference in hearing loss between vehicle-treated Alport mice and losartan-treated Alport mice.

Alport mice at 16 kHz (FIG. 9B; P<0.05 Alport Spar vs. Alport V). There was no significant effect of losartan on hearing loss.

Figure 10:
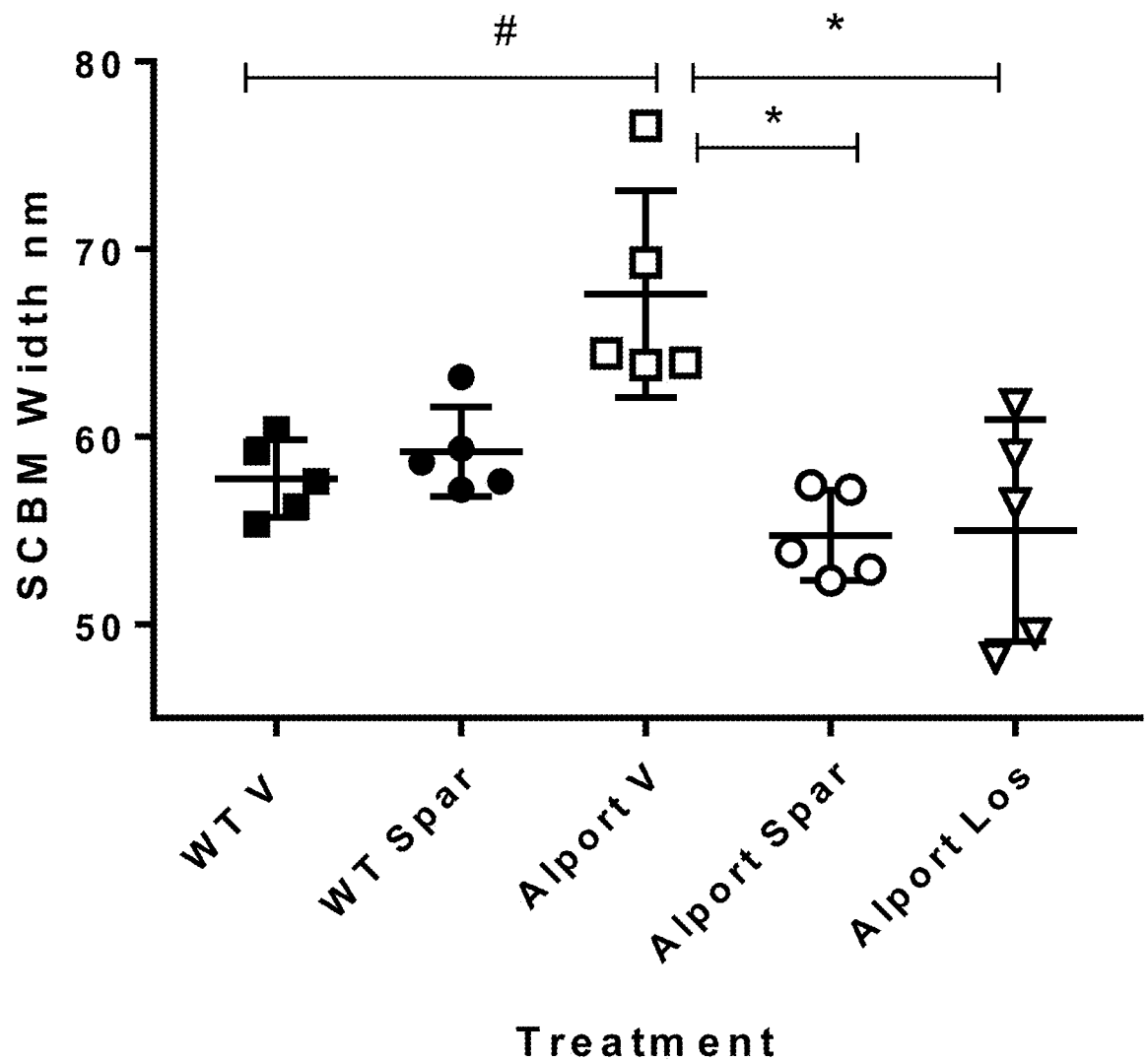
FIG. 10. Strial capillary basement membrane width. Treatment of Alport mice 3-8.5 weeks of age with sparsentan or losartan prevented the increase in SCBM width that was observed in the vehicle-treated Alport mice. Vehicle-treated wild-type mice (WT V), sparsentan-treated wild-type mice (WT Spar), vehicle-treated Alport mice (Alport V), sparsentan-treated Alport mice (Alport Spar), and losartan-treated Alport mice (Alport Los). SCBM=Strial capillary basement membrane. Data are shown from individual animals (n=5). *$P<0.05$ Alport Spar or Alport Los compared to Alport V; #$P<0.05$ Alport V compared to WT V.

The analysis of cochlear structure involved measures of basement membrane width in the capillaries of the stria vascularis using transmission electron microscopy. FIG. 10 shows that sparsentan and losartan prevented the increase in strial capillary basement width observed in Alport mice treated with vehicle. Sparsentan prevented the SCBM thickening in the ear that was observed in APV (mean SCBM width±SD nm; WT V—57.8±2.1, Alport V—67.6±5.5, Alport Spar—54.7±2.4; Alport Los—55.0±5.9; P<0.05 Alport Spar vs. Alport V and Alport Los vs. Alport V) (FIG. 10). These data indicate that sparsentan treatment is capable of preventing the structural and functional auditory effects of Alport syndrome in a mouse model of the autosomal form of the disease.

Figure 11:
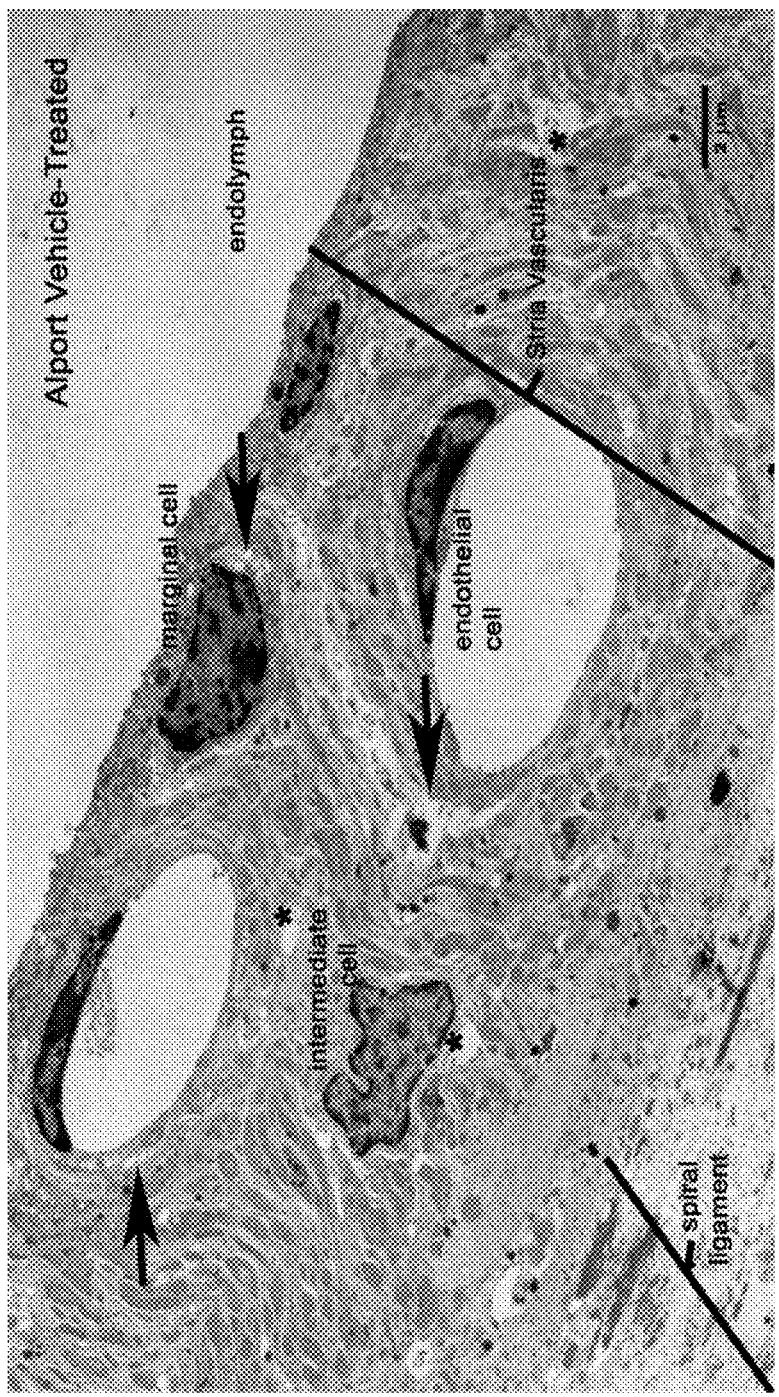
FIG. 11. TEM image of the lower apical cochlear turn in a vehicle-treated Alport mouse.
Figure 12:
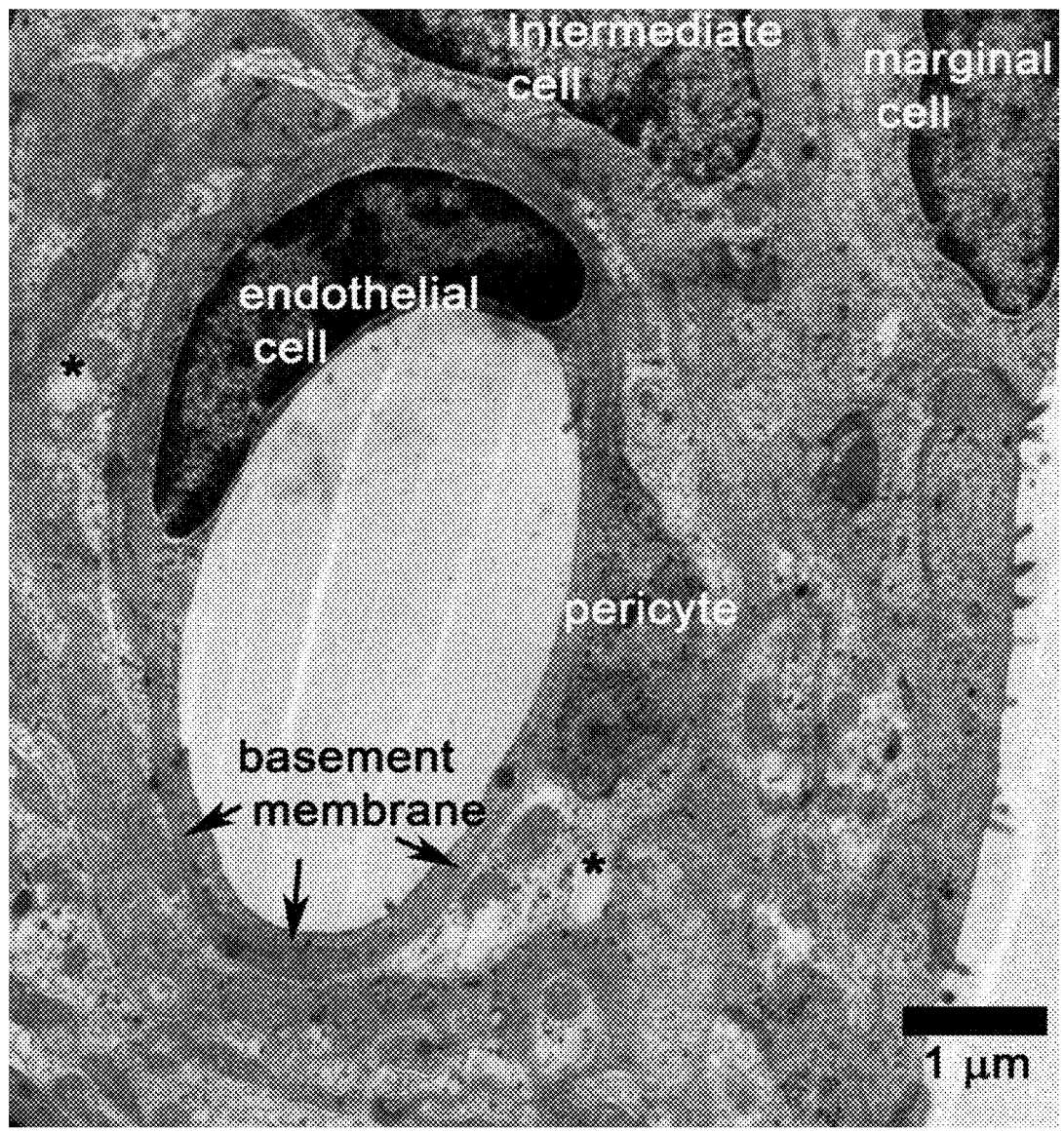
FIG. 12. Higher magnification TEM image of a stria vascularis from a vehicle-treated Alport mouse.
Figure 13:
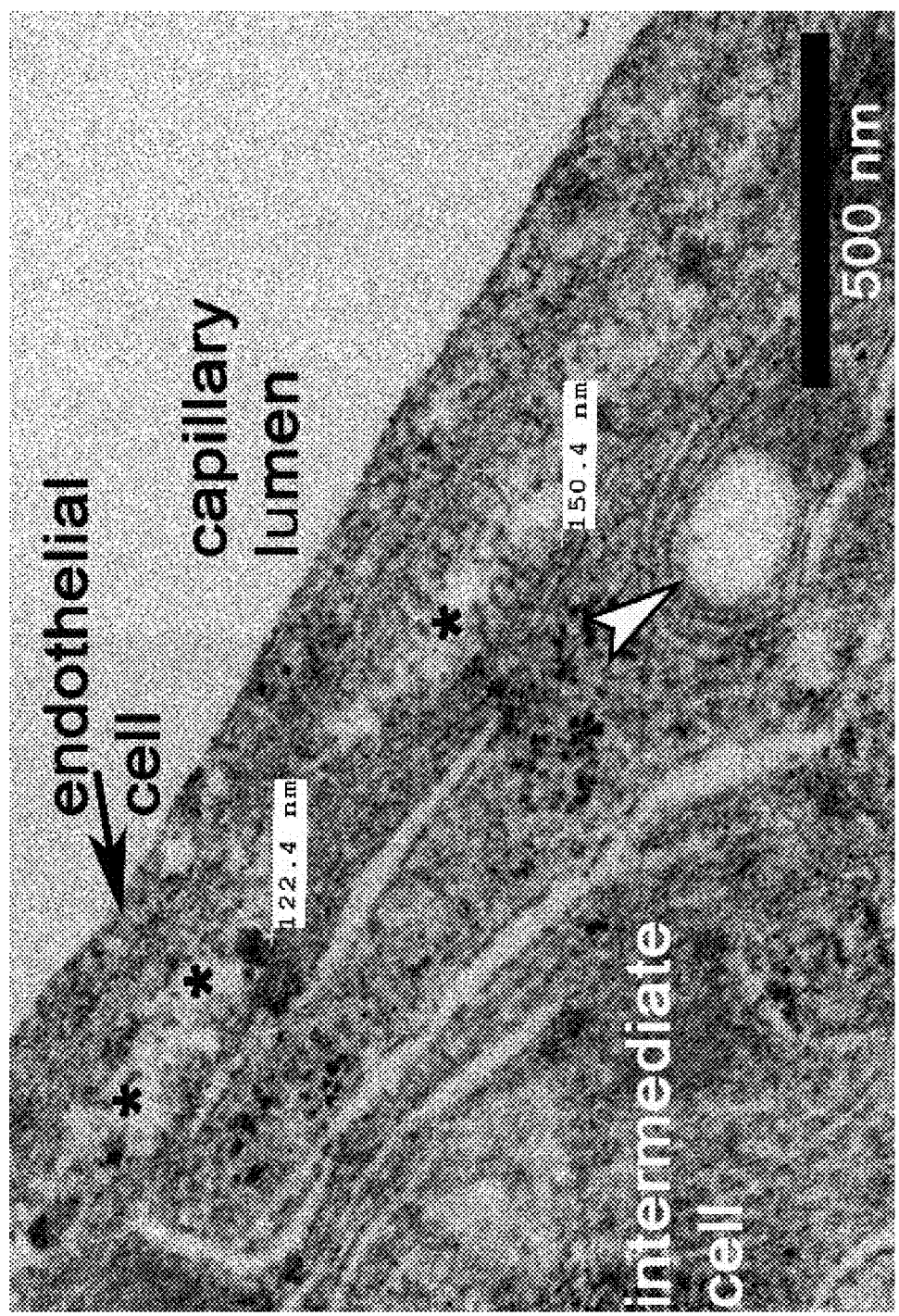
FIG. 13. Partial view of a capillary by TEM from a stria from a vehicle-treated Alport mouse.

FIG. 11 is an EM image of the lower apical turn in a vehicle-treated Alport mouse, showing isolated lucent vacuoles in intermediate cell processes (asterisk), and intercellular edema between the processes of the marginal cells (dark cytoplasm) and intermediate cells (light cytoplasm) with instances of vacuoles (arrows in the edematous space). The underlying spiral ligament shows bundles of collagen between fibrocytes. A higher magnification image of a stria vascularis of a vehicle-treated Alport mouse is shown in FIG. 12, showing the basement membrane surrounding the endothelial cell. The intermediate cell contains vacuoles (indicated by the asterisk) particularly in cytoplasm contacting the basement membrane and the lateral processes of pericytes. FIG. 13 is a partial view of a capillary from a stria of a vehicle-treated Alport mouse, showing thickened basement membranes as evidenced by the measurements of 122.4 nm and 150.4 nm. The trilaminar appearance of the basement membrane has been replaced by splitting and lamellation (asterisks). A large vacuole (indicated by the white arrowhead) is noted in a lateral process of an intermediate cell.

Figure 14:
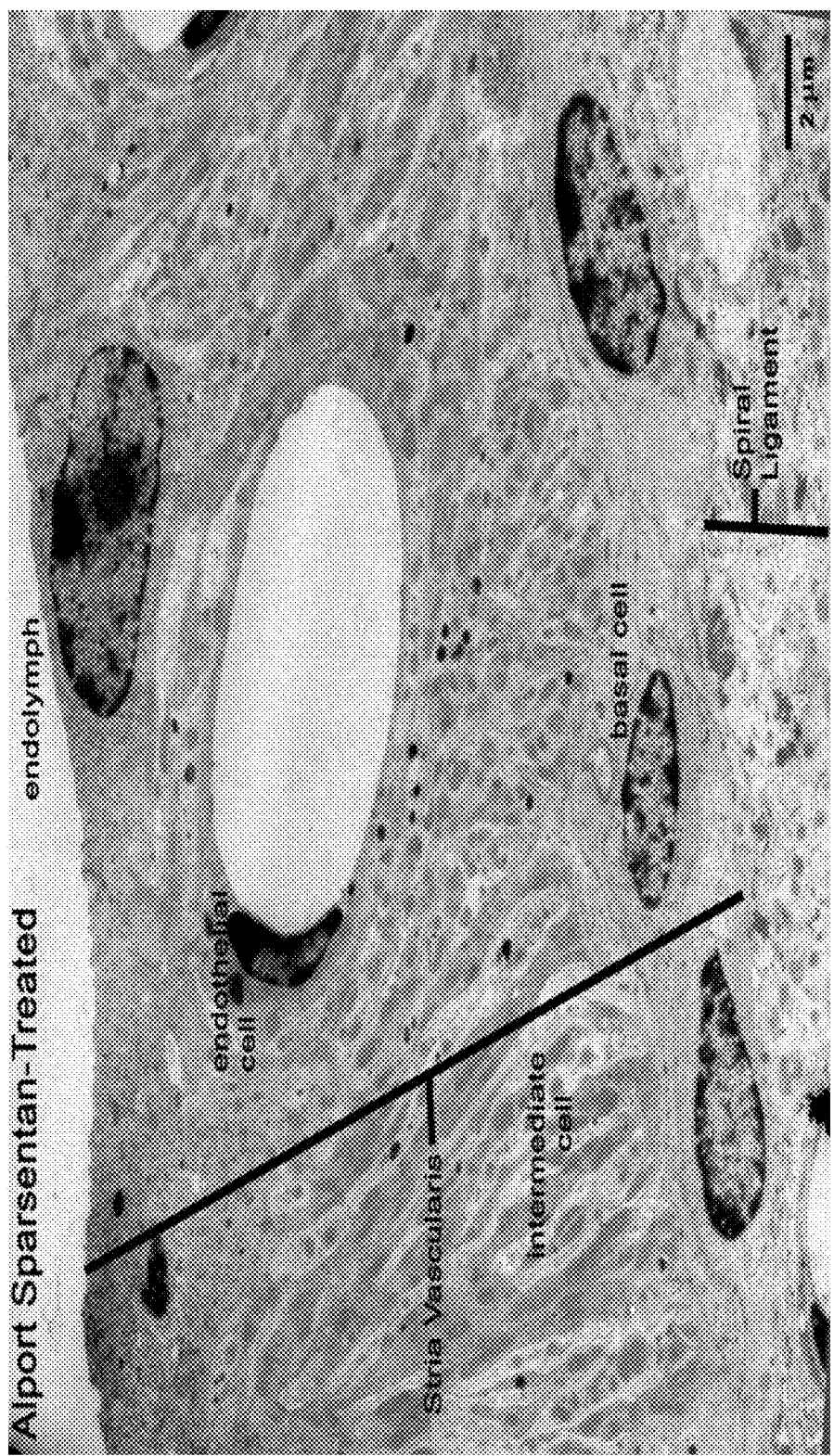
FIG. 14. TEM image of the lower apical cochlear turn in a sparsentan-treated Alport mouse.
Figure 15:
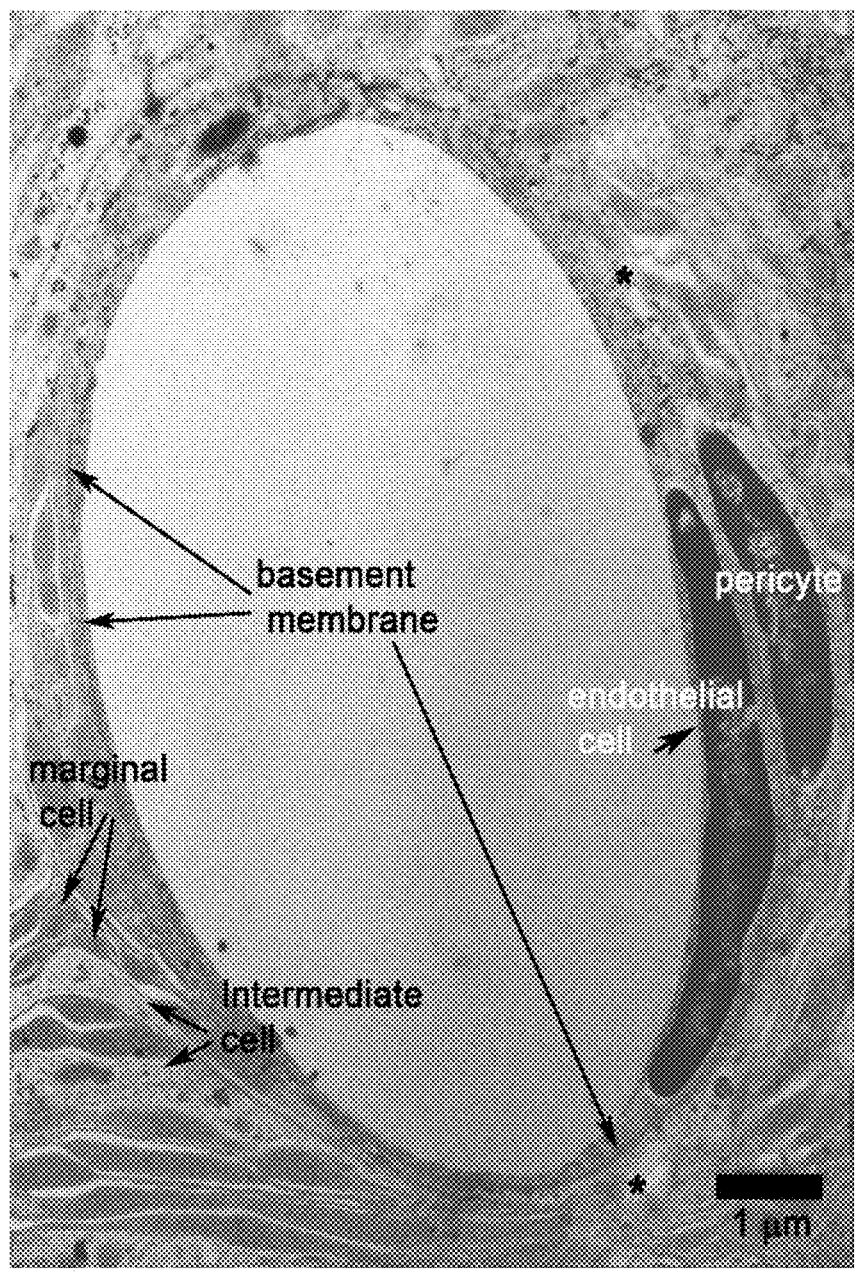
FIG. 15. A higher magnification TEM image of a stria vascularis from a sparsentan-treated Alport mouse.
Figure 16:
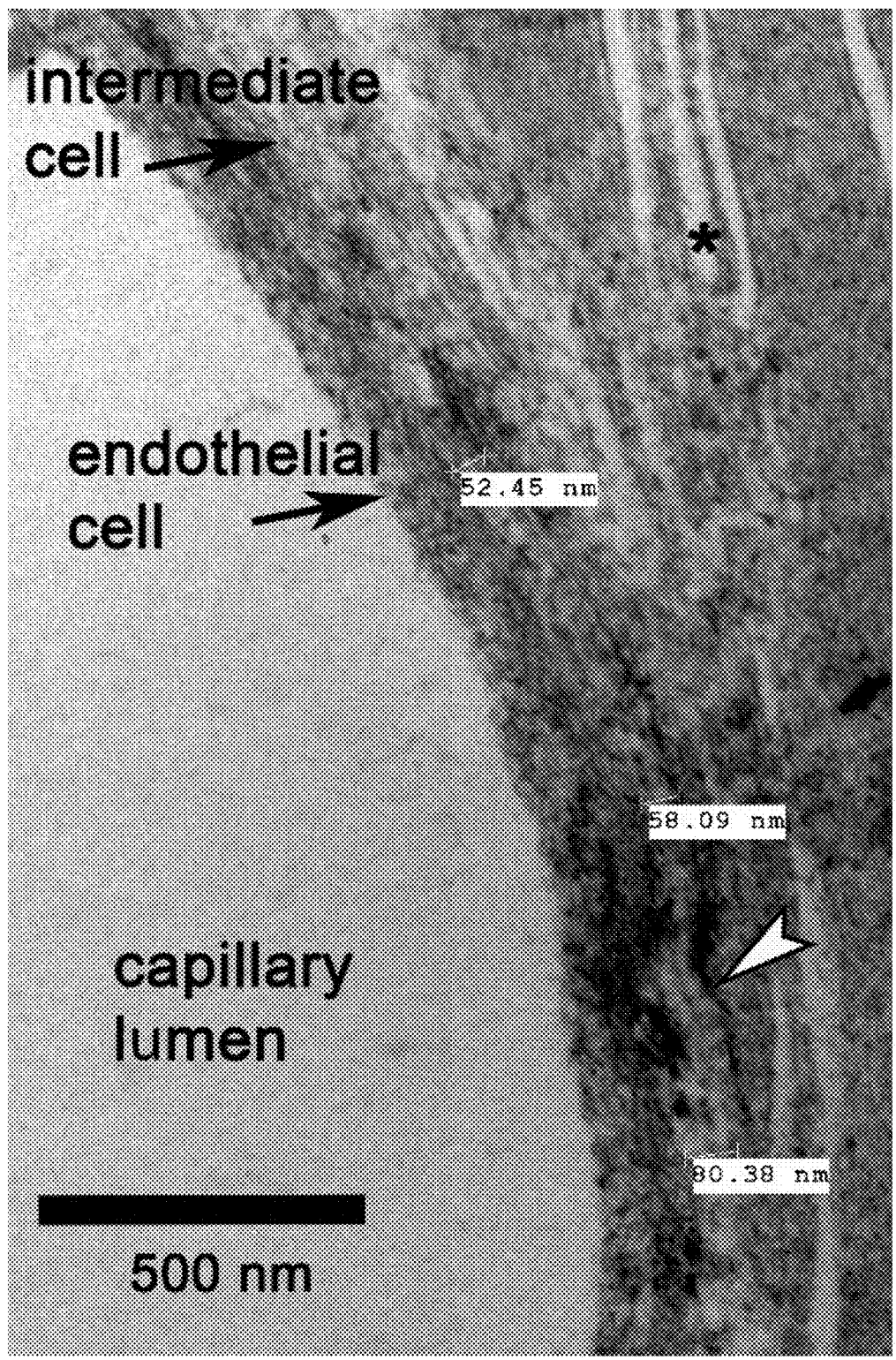
FIG. 16. Partial view of a capillary by TEM from a stria in a sparsentan-treated Alport mouse.
Figure 17:
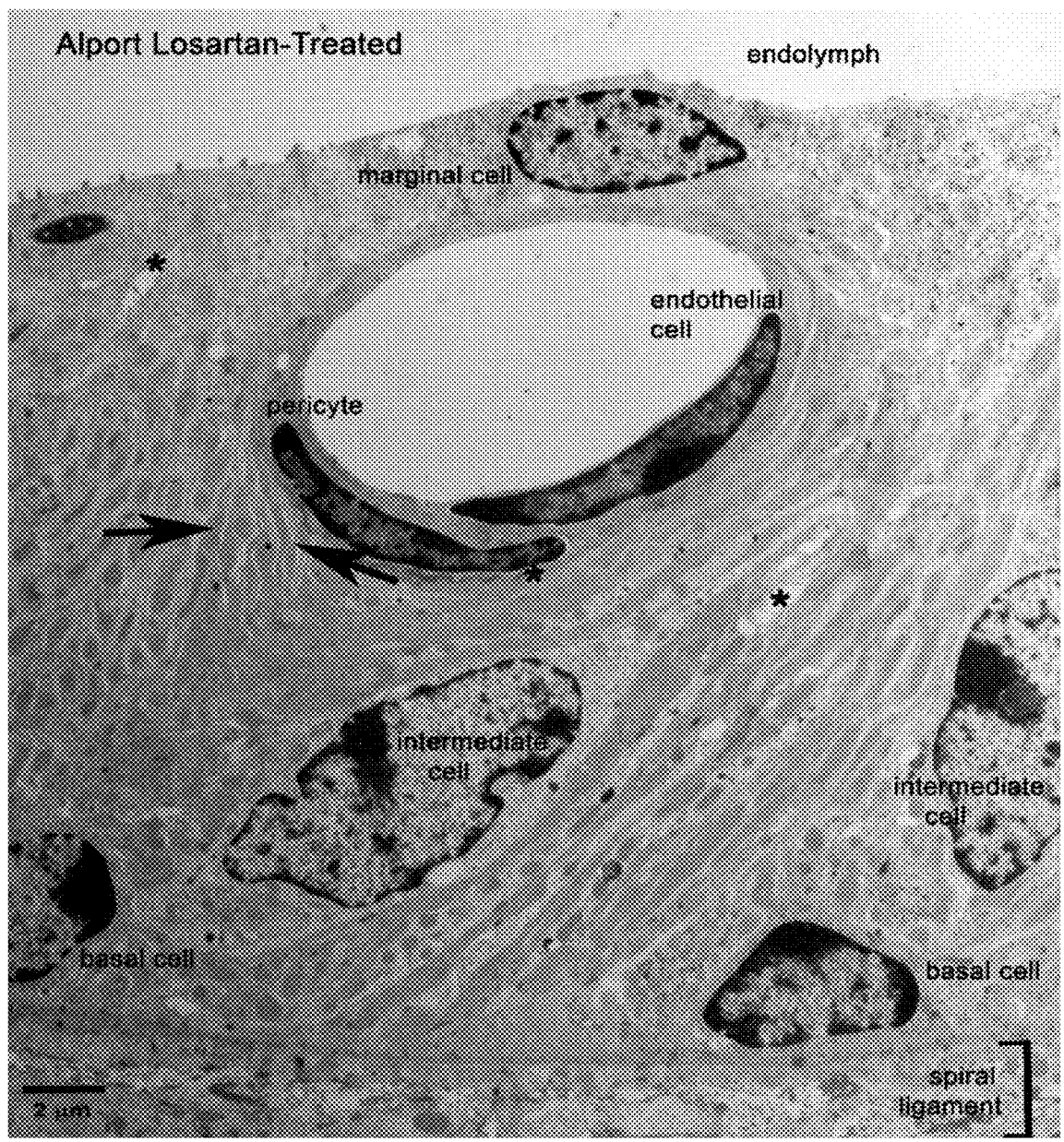
FIG. 17. TEM image of the lower basal cochlear turn in a losartan-treated Alport mouse.

In contrast, the lower apical turn in a sparsentan-treated Alport mouse shown in FIG. 14 has substantially fewer extra- and intra-cytosolic vacuoles. In addition, the intercellular edema does not appear between the lateral processes of the marginal (dark cytoplasm) and intermediate cells (light cytoplasm). Overall, the appearance of the stria vascularis appears more like that of normal, healthy wild-type mice (not shown). FIG. 15 shows a strial capillary at higher magnification, showing a few, small vacuoles (indicated by the asterisk) and evidence of extracellular space between the marginal and intermediate cell processes. FIG. 16 shows a partial view of a capillary from a stria of a sparsentan-treated Alport mouse. The basement membrane has normal thickness as evidenced by the measurements of 52.45 nm, 58.09 nm, and 80.38 nm. The trilaminar appearance of the basement membrane can be detected in some areas (indicated by the white arrowhead). The intercellular space between the lateral processes (indicated by the asterisk) is reduced.

FIGS. 17-23 depict variable pathology in the stria vascularis of losartan-treated Alport mice, from minimal changes (where physiological function, i.e., endocochlear potential, may be normal or near normal) to the most severe damage observed (where physiological function is highly questionable). In all images, the strial capillary basement membrane width is decreased from that measured in non-treated Alport mice. The lower basal turn in a losartan-treated Alport mouse (FIG. 17) has minimal changes in the cochlear lateral wall (stria vascularis and spiral ligament) ultrastructure. The pathology involves intercellular edema between the processes of marginal (dark cytoplasm) and intermediate cells (light cytoplasm) (indicated by arrows). Isolated lucent vacuoles (indicated by the asterisk) between the marginal and intermediate cell processes occur occasionally. The underlying spiral ligament shows sparse extracellular matrix and a few collagen bundles between fibrocytes. This tissue does not appear to be affected by losartan treatment.

Figure 18:
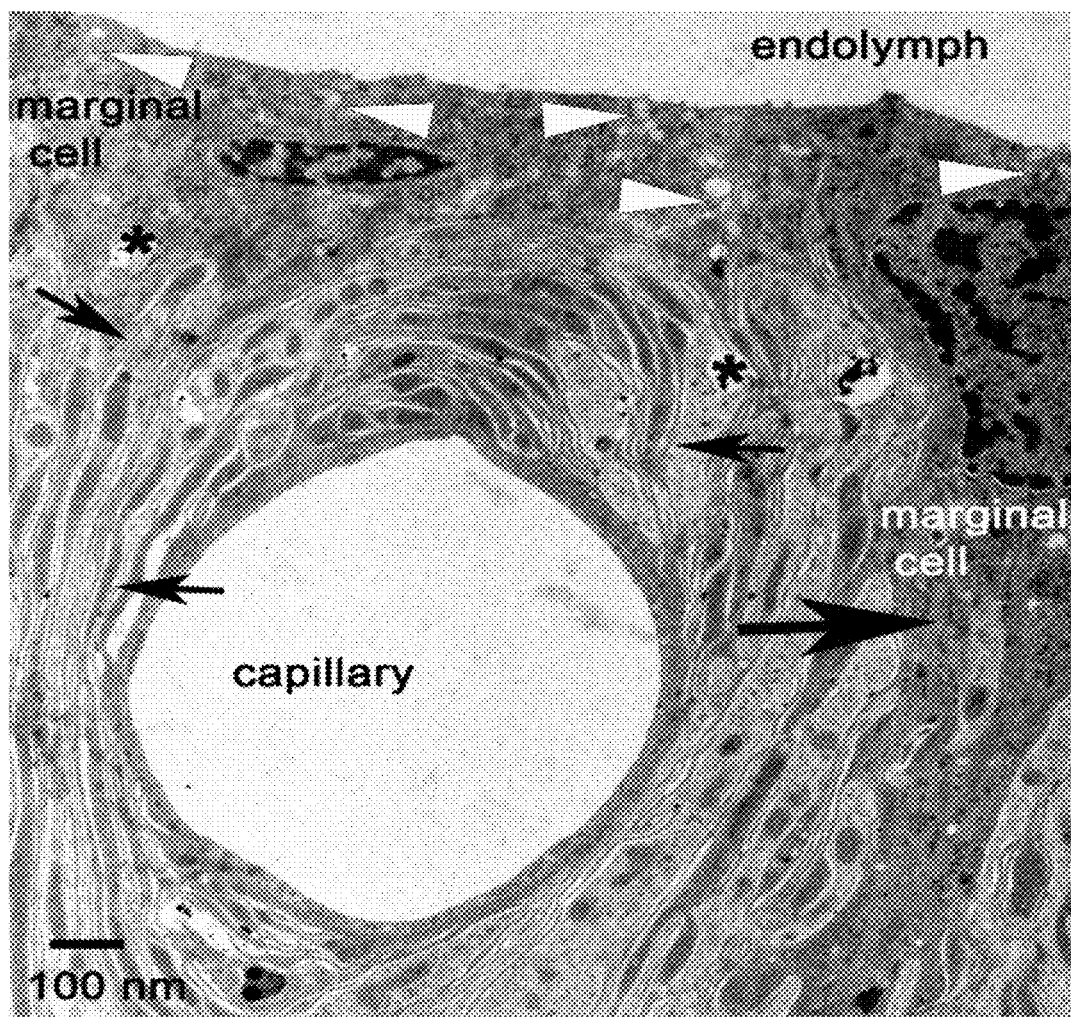
FIG. 18. A higher magnification TEM image of a stria vascularis in a losartan-treated Alport mouse (different mouse than that in FIG. 17).
Figure 19:
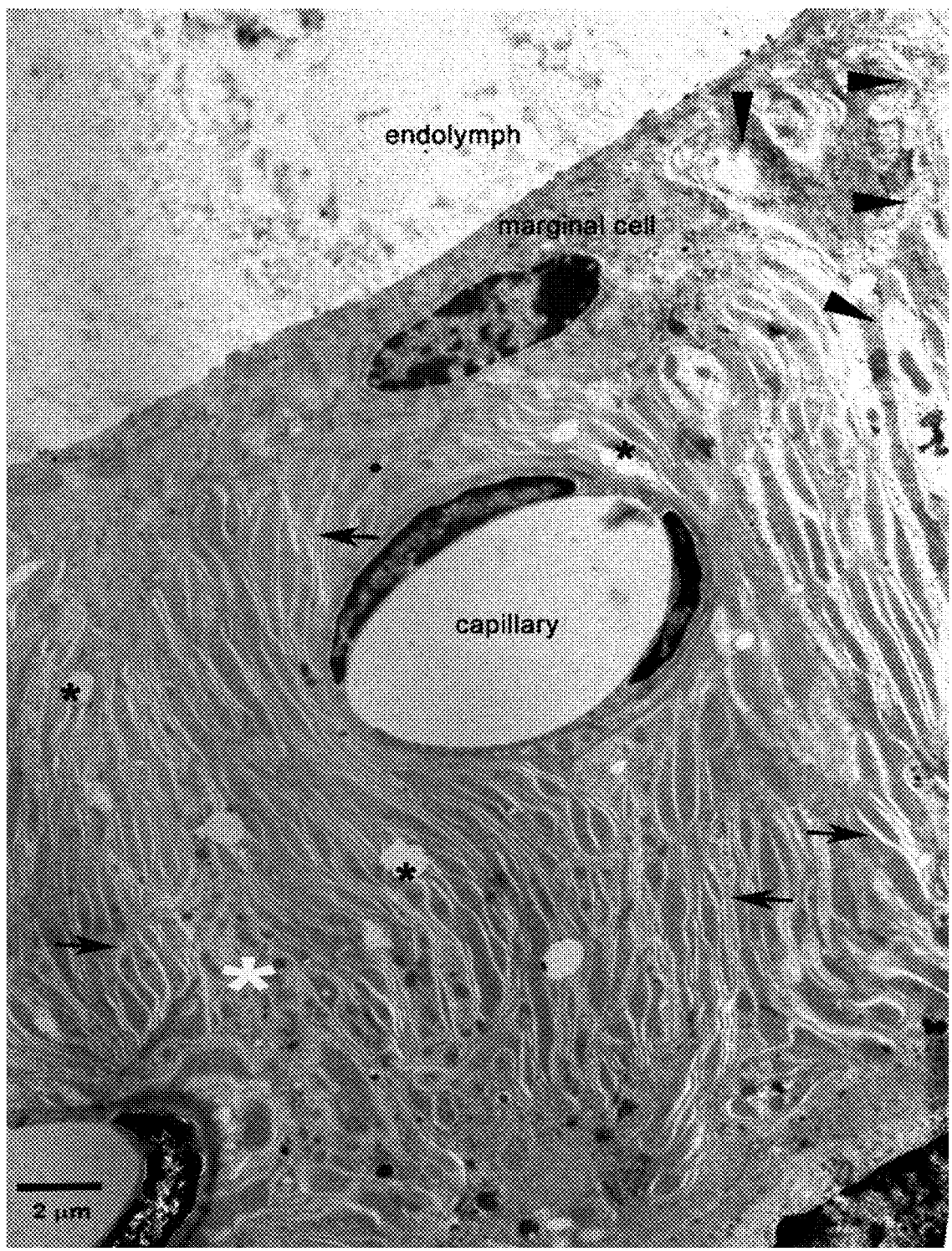
FIG. 19. Wider view of strial tissue in a losartan-treated Alport mouse by TEM (same mouse as in FIG. 18).

FIG. 18 shows a higher magnification image of a different Alport mouse, where the marginal cell cytoplasm adjacent to the apical plasmalemma shows numerous lucent vacuoles (indicated by the white arrowhead), and the thin basolateral processes extending into the strial interior have coalesced into a thick process (indicated by the large black arrow). Increased intercellular edema (indicated by the thin black arrows) is observed between processes of the marginal (dark cytoplasm) and intermediate cells (light cytoplasm) with instances of vacuoles (indicated by the asterisks) in the edematous space.

A wider view of the strial tissue (FIG. 19) shows that greater strial tissue disarray occurs from left to right. The intercellular pathology of vacuoles (indicated by the black asterisks) and edema (indicated by the thin arrows) on the left and center progress to loss of cytosol in the lateral processes as well as marginal cell cytosol (indicated by black arrowheads) on the right. Phagocytotic activity (indicated by the white asterisk) is observed adjacent to the capillary (lower left corner).

Figure 20:
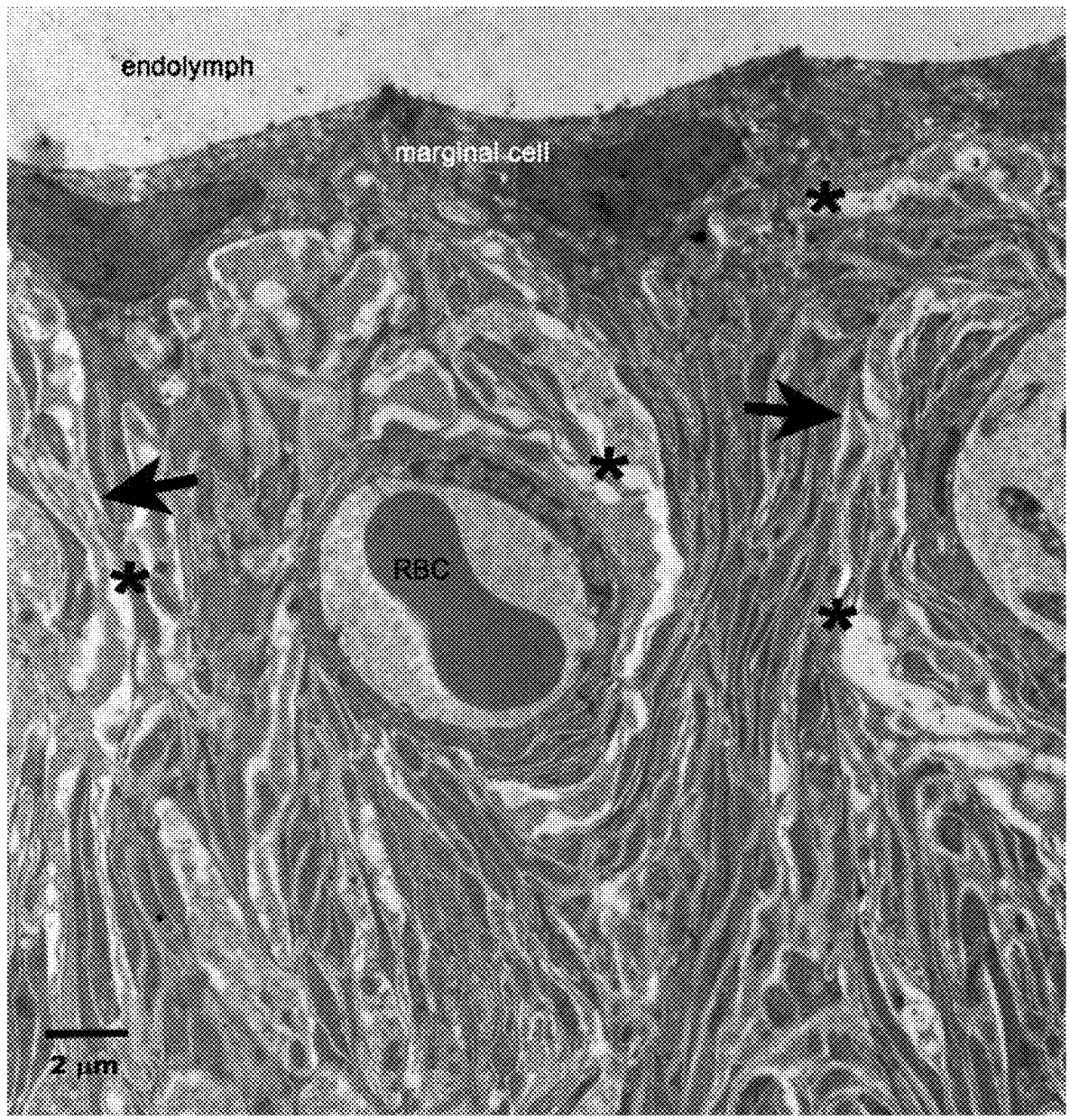
FIG. 20. TEM image of strial pathology in a losartan-treated Alport mouse (different mouse than that in FIGS. 17-19).
Figure 21:
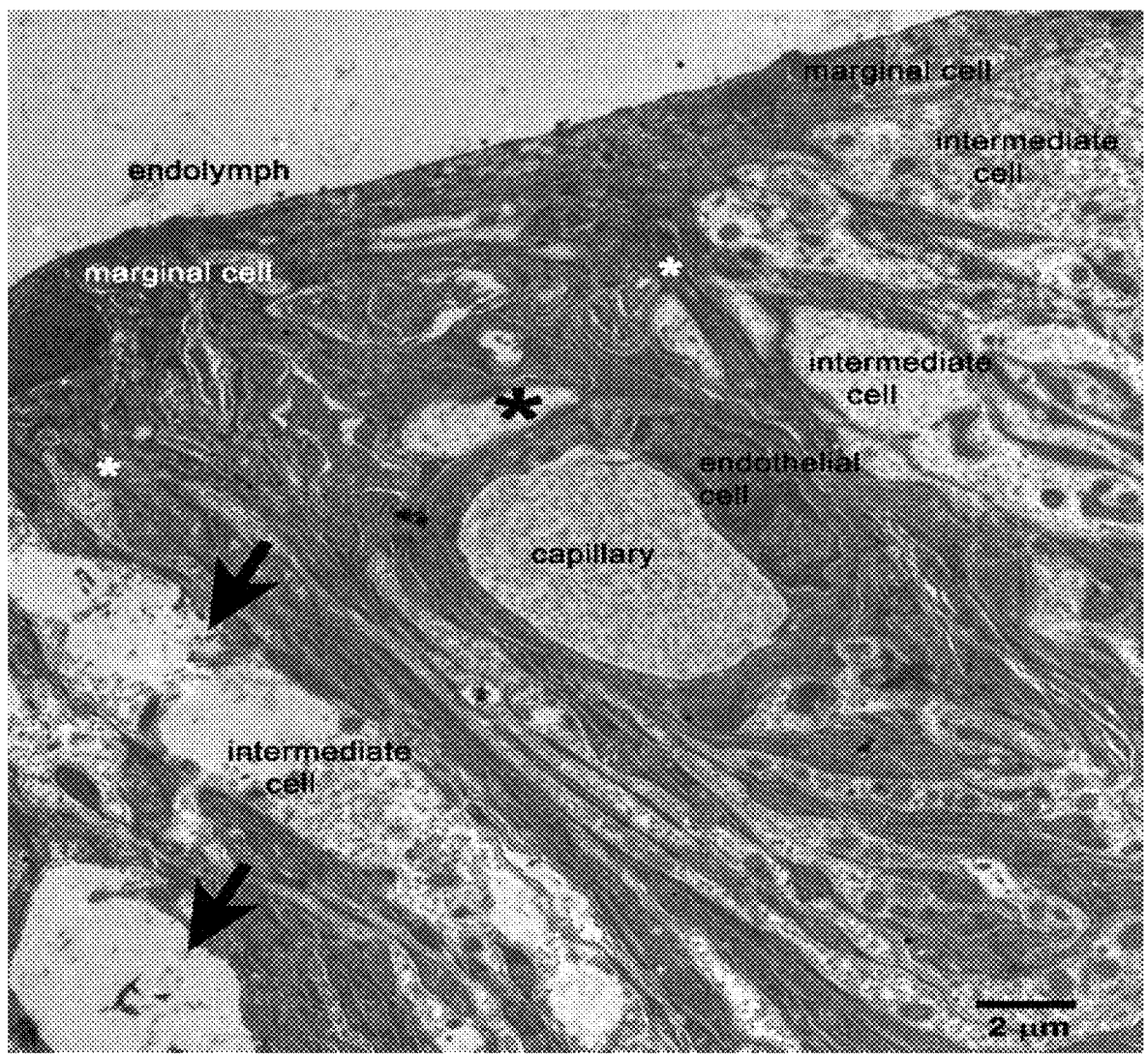
FIG. 21. TEM image of severe strial pathology in a losartan-treated Alport mouse (fourth and fifth mouse example).

A third losartan-treated Alport mouse exhibited increased intercellular edema (FIG. 20). It is visible, not only as thin very light stripes (indicated by arrows) between the thin processes of the marginal (dark cytoplasm) and intermediate cells (light cytoplasm), but also as wider regions (indicated by asterisks), often appearing as a merging of the individual vacuoles noted in less damaged tissue (compare to FIG. 17-19). Additionally, plasma and a red blood cell (RBS) are observed in the capillary. The plasma noted in FIG. 20 is present in the capillary in FIG. 21, but also has leaked into the tissue (indicated by the asterisk). Retraction and degeneration of intermediate cell processes are also observed (FIG. 21, arrows and upper right corner). Moreover, while a marginal cell (FIG. 21, white label) has maintained basolateral processes (indicated by white asterisks), an adjacent marginal cell (FIG. 21, black label, upper right corner) lacks processes. The cell is a thin layer of cytosol, such as squamous epithelium, bordering the endolymph.

Figure 22:
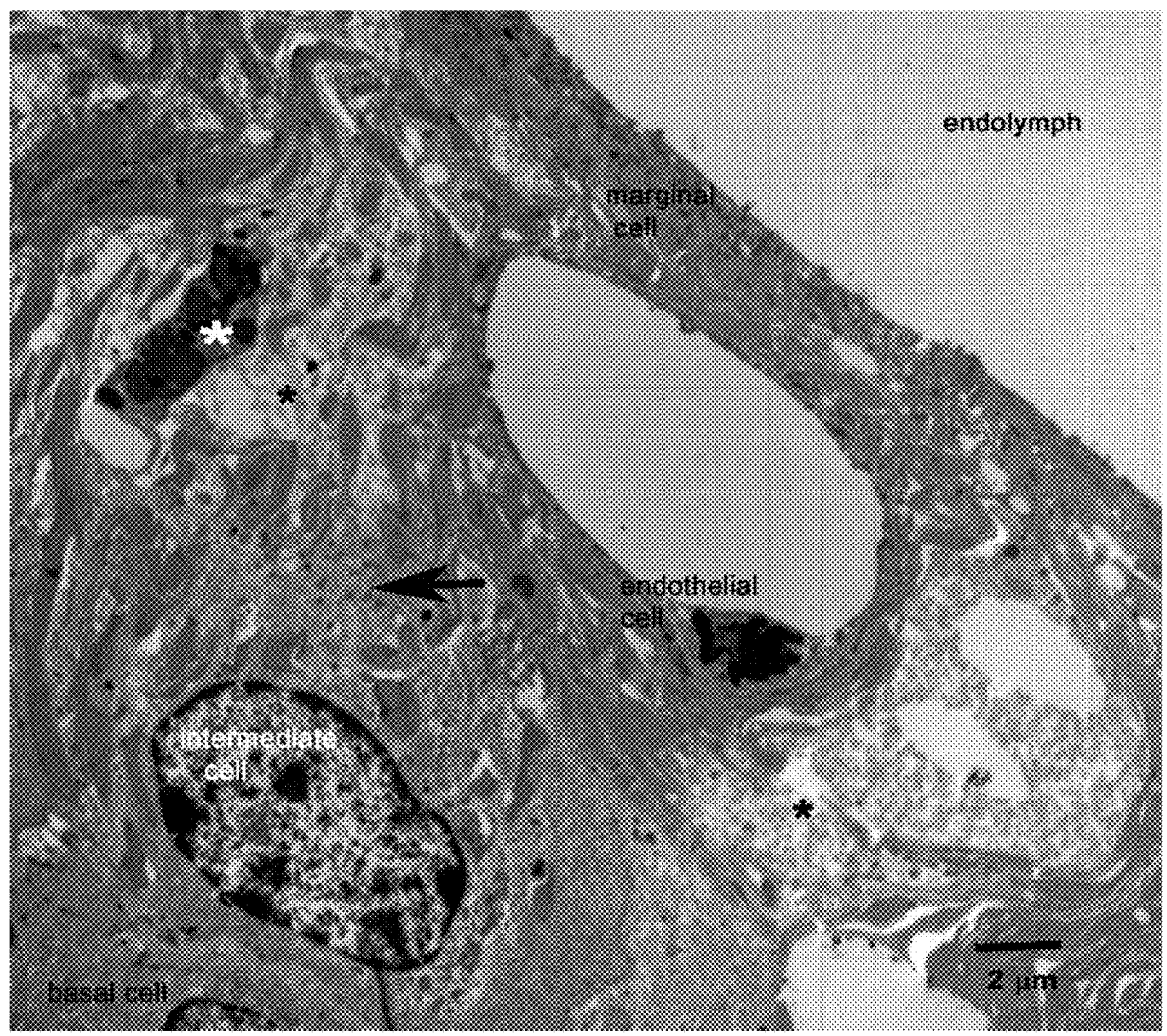
FIG. 22. TEM image of severe strial pathology in a losartan-treated Alport mouse.
Figure 23:
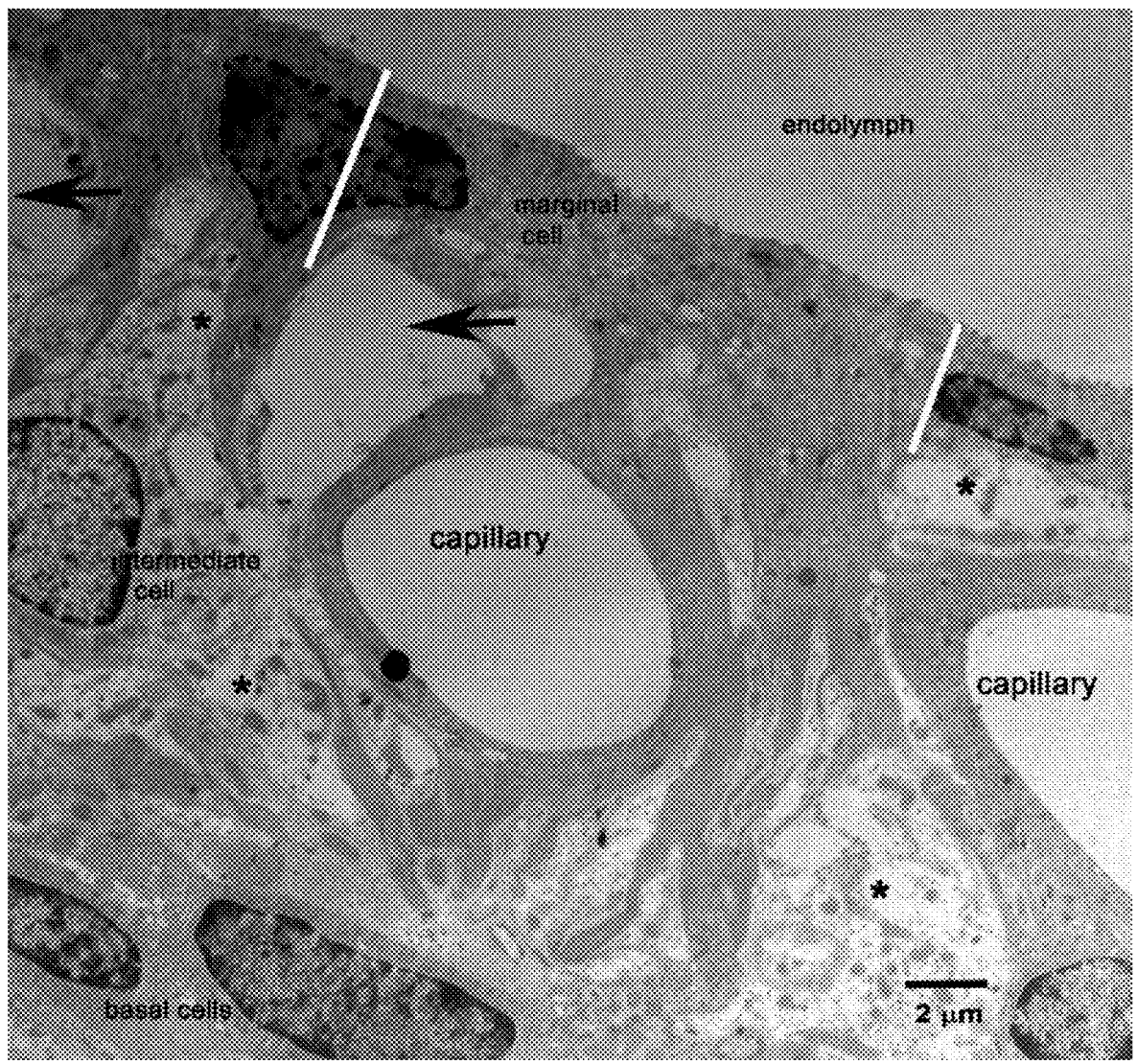
FIG. 23. TEM image of severe strial pathology in a losartan-treated Alport mouse.

Two examples of the most severe strial pathology observed in losartan-treated Alport mice are shown in FIGS. 22-23. In both, degenerating intermediate cell processes (indicated by the black asterisks) are observed, while cytosol surrounding the nucleus (FIG. 22, black arrow) remains more intact. Marginal cell processes remain present in reduced density in some cells but when the processes retract, the cytosol surrounding the nucleus also reduces (FIG. 23, shorter white line over right marginal cell vs longer on left marginal cell). Phagocytotic activity is observed (FIG. 22, white asterisk) in the region of the degenerating intermediate cell processes. Large membrane bound vacuoles are observed (FIG. 23, arrows) and may represent an expansion of the vacuoles noted in the other images with less severe strial pathology.

Figure 24:
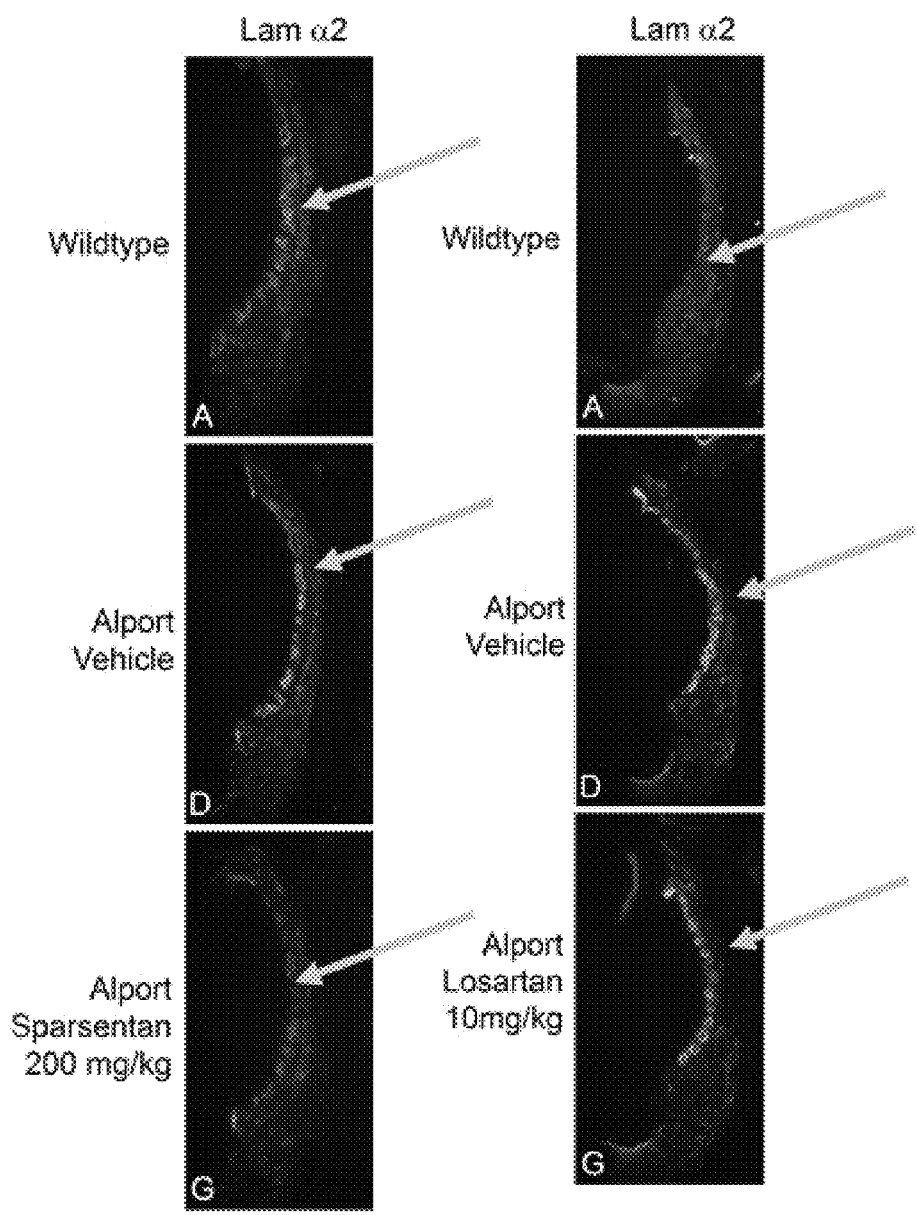
FIG. 24. Sparsentan prevented accumulation of extracellular matrix protein laminin α2 in stria of Alport mice. Immunofluorescent images of stria from wild-type mice treated with vehicle or Alport mice treated with vehicle, sparsentan (200 mg/kg), or losartan (10 mg/kg) from 3 to 7 weeks of age. Immunofluorescent images are following incubation with an antibody to laminin α2.

FIG. 24 shows the accumulation of the extracellular matrix protein laminin α2 in stria following immunofluorescent staining with an anti-laminin α2 antibody (green stain). Sparsentan treatment (200 mg/kg) from 3-7 weeks of age (from pilot study) prevented the accumulation of laminin α2, whereas accumulation of laminin α2 in losartan-treated Alport mice during the early intervention study did not appear different from vehicle-treated Alport mice.

In summary, sparsentan, but not losartan, significantly attenuated noise-induced hearing loss. These results suggest that, if translated to the clinic, sparsentan may reduce or prevent hearing loss for patients having Alport syndrome.

SUMMARY

These data demonstrate the ability of dual AT1/ETA inhibition with sparsentan to provide nephroprotection in Alport mice, in both glomerular and tubulointerstitial compartments. Sparsentan can significantly attenuate the development of functional and structural changes in Alport mice, and increase lifespan when administered prior to the onset of kidney injury (3 weeks of age) and when administered after the commencement of fibrosis and glomerulosclerosis (5 weeks age). TEM imaging highlighted the ability of sparsentan treatment to maintain the morphology of the GBM and attenuate podocyte effacement. In the late intervention study, sparsentan provided significant nephroprotection in Alport mice, and to a greater extent than in the losartan-treated group.

Sparsentan, but not losartan, significantly attenuated noise-induced hearing loss in Alport mice treated from 3 weeks of age. These results suggest that, if translated to the clinic, sparsentan may reduce or prevent hearing loss and renal injury for patients having Alport syndrome.

Example 2

Exemplary Liquid Formulations

Formulation A

Batch size was 3 L. Sodium benzoate was dissolved in 80% of total water quantity. Citric acid was added to achieve pH 3.0±0.2 units. Sucralose and flavor were added stirred until dissolved. Xanthan gum was added with stirring and stirring continued until fully dissolved. Sparsentan was added using homogenization until fully dispersed and a uniform suspension obtained, and the remaining water was added. Formulation A is described in Table 4. Stability data are provided in Tables 5-8. Satisfactory stability was observed for Formulation A, with no significant changes from the initial time-point in appearance or physical or chemical stability after storage for 14 weeks at 25° C./65% RH and 40° C./75% RH. Additionally, after storage for 14 weeks at 40° C./75% RH, Formulation A met the requirements of Ph Eur 5.1.3 for Preservative Efficacy Testing (PET).

TABLE 4

Description of Formulation A

| Ingredient | Quantity (mg/mL) |
|---|---|
| Sparsentan | 20.0 |
| Citric acid | 5.23 |
| Sodium benzoate | 2.30 |
| Xanthan gum | 8.00 |
| Sucralose | 0.75 |
| Strawberry flavor PHS120116 | 1.00 |
| Water | 962.72 |
| pH | 3.2 |

TABLE 5

Initial and 4 week stability for Formulation A at 25° C./60% relative humidity and accelerated conditions

| Test | Initial | 4 weeks 25° C./60% RH | 4 weeks 40° C./75% RH |
|---|---|---|---|
| Appearance | White, opaque suspension | White to off-white, opaque suspension | White to off-white, opaque suspension. Small amount of sedimentation which was easily re-suspended on shaking. |
| Assay of sparsentan (% Target) | 100, 101, 98, 99, 103 | 101, 102 | 103, 103 |
| Related substances (% relative to sparsentan) Individual | | | |
| Peak at RRT 0.98 | 0.12 | 0.12 | 0.12 |
| Peak at RRT 1.21 | 0.05 | 0.05 | 0.06 |
| Total | 0.17 | 0.17 | 0.18 |
| Assay of sodium benzoate (% Target) | 100, 102, 98, 100, 103 | 100, 101 | 101, 101 |
| Viscosity (cP) Spindle 3 at 50 rpm | 1186 | 1154 | 1090 |
| pH | 3.3 | 3.3 | 3.3 |
| Microbiological testing (PET) | | | |

TABLE 6

14 week stability for Formulation A at 25° C./60% relative humidity and accelerated conditions

| Test | 14 weeks 25° C./60% RH | 14 weeks 40° C./75% RH |
|---|---|---|
| Appearance | White to off-white, opaque suspension. Small amount of sedimentation which was easily re-suspended on shaking. | White to off-white, opaque suspension. Small amount of sedimentation which was easily re-suspended on shaking. |

TABLE 6-continued 14 week stability for Formulation A at 25° C./60% relative humidity and accelerated conditions

| | 14 weeks | |
|---|---|---|
| Test | 25° C./60% RH | 40° C./75% RH |
| Assay of sparsentan (% target) | 101, 101 | 101, 102 |
| Related substances (% relative to sparsentan) Individual | | |
| Peak at RRT 0.98 | 0.12 | 0.11 |
| Peak at RRT 1.21 | 0.05 | 0.05 |
| Total | 0.17 | 0.17 |
| Assay of sodium benzoate (% target) | 100, 100 | 100, 100 |
| Viscosity (cP) Spindle 3 at 50 rpm | 1073 | 1056 |
| pH | 3.3 | 3.3 |
| Microbiological testing (PET) | Complies Ph Eur 5.1.3 | Complies Ph Eur 5.1.3 |

TABLE 7

Dissolution of the API from suspension at stability time points for Formulation A

| | % sparsentan dissolved (n = 3) at specified time-points | | | | | | | | | | | |
|---|---|---|---|---|---|---|---|---|---|---|---|---|
| | 5 min | | 10 min | | 15 min | | 30 min | | 45 min | | 60 min | |
| | % | x | % | x | % | x | % | x | % | x | % | x |
| Initial | 92 | 95 | 101 | 100 | 103 | 103 | 104 | 104 | 104 | 104 | 104 | 104 |
| | 94 | | 99 | | 104 | | 105 | | 105 | | 105 | |
| | 98 | | 101 | | 102 | | 103 | | 103 | | 103 | |
| 4 weeks at 25° C./ 60% RH | 100 | 98 | 99 | 100 | 101 | 100 | 102 | 101 | 102 | 101 | 102 | 101 |
| | 98 | | 100 | | 101 | | 102 | | 102 | | 102 | |
| | 96 | | 100 | | 99 | | 100 | | 100 | | 100 | |
| 4 weeks at 40° C./ 75% RH | 97 | 99 | 102 | 102 | 102 | 103 | 103 | 103 | 103 | 104 | 103 | 104 |
| | 101 | | 102 | | 103 | | 104 | | 104 | | 104 | |
| | 100 | | 103 | | 103 | | 104 | | 104 | | 104 | |
| 14 weeks at 25° C./ 60% RH | 96 | 95 | 102 | 101 | 103 | 102 | 104 | 102 | 104 | 103 | 104 | 103 |
| | 93 | | 99 | | 100 | | 101 | | 101 | | 101 | |
| | 96 | | 101 | | 102 | | 103 | | 103 | | 103 | |
| 14 weeks at 40° C./ 75% RH | 99 | 98 | 102 | 103 | 105 | 104 | 106 | 104 | 106 | 104 | 106 | 104 |
| | 97 | | 103 | | 103 | | 103 | | 103 | | 103 | |
| | 98 | | 98 | | 103 | | 104 | | 104 | | 104 | | x = mean

TABLE 8

Particle size distribution at stability time points for Formulation A

| Time-point/storage condition | D10 (μm) | D50 (μm) | D90 (μm) |
|---|---|---|---|
| Initial | 11.729 | 49.271 | 130.978 |
| 4 weeks at 25° C./60% RH | 11.461 | 50.097 | 138.708 |
| 4 weeks at 40° C./75% RH | 11.473 | 49.364 | 132.287 |
| 14 weeks at 25° C./60% RH | 11.693 | 49.797 | 135.709 |
| 14 weeks at 40° C./75% RH | 11.498 | 48.710 | 131.655 |

Formulation B

Batch size was 3 L. Sodium benzoate was dissolved in 80% of total water quantity. Citric acid was added to achieve pH 3.0±0.2 units. Sucralose and flavor were added stirred until dissolved. Xanthan gum was added with stirring and stirring continued until fully dissolved. Sparsentan was adding using homogenization until fully dispersed and a uniform suspension obtained, and the remaining water was added. Formulation B is described in Table 9. Stability data are provided in Tables 10-13. Satisfactory stability was observed for Formulation B, with no significant changes from the initial time-point in appearance or physical or chemical stability after storage for 14 weeks at 25° C./65% RH and 40° C./75% RH. Additionally, after storage for 14 weeks at 40° C./75% RH, Formulation B met the requirements of Ph Eur 5.1.3 for Preservative Efficacy Testing (PET).

TABLE 9

Description of Formulation B

| Ingredient | Quantity (mg/mL) |
|---|---|
| Sparsentan | 20.00 |
| Citric acid | 5.50 |
| Sodium benzoate | 2.30 |
| Xanthan gum | 5.00 |
| Sucralose | 0.75 |
| Lemon Cream flavor PHS459630 | 1.00 |
| Water | 965.45 |
| pH | 3.3 |

TABLE 10

Initial and 4 week stability for Formulation B at 25° C./60% relative humidity and accelerated conditions

| | | 4 weeks | |
|---|---|---|---|
| Test | Initial | 25° C./60% RH | 40° C./75% RH |
| Appearance | White, opaque suspension | White, opaque suspension. Small amount of sedimentation which was easily re-suspended on shaking. | White, opaque suspension. Small amount of sedimentation which was easily re-suspended on shaking. |
| Assay of sparsentan (% target) | 102, 102, 100, 100, 101 | 102, 101 | 103, 102 |
| Related substances (% relative to sparsentan) Individual | | | |
| Peak at RRT 0.98 | 0.12 | 0.12 | 0.12 |
| Peak at RRT 1.21 | 0.05 | 0.06 | 0.06 |
| Total | 0.17 | 0.18 | 0.18 |
| Assay of sodium benzoate (% target) | 102, 102, 100, 100, 100 | 102, 102 | 101, 102 |
| Viscosity (cP) Spindle 3 at 50 rpm | 581 | 540 | 485 |
| pH | 3.2 | 3.2 | 3.2 |
| Microbiological testing (PET) | | | |

TABLE 11

14 week stability for Formulation B at 25° C./60% relative humidity and accelerated conditions

| | 14 weeks | |
|---|---|---|
| Test | 25° C./60% RH | 40° C./75% RH |
| Appearance | White, opaque suspension. Small amount of sedimentation which was easily re-suspended on shaking. | White, opaque suspension. Large amount of sedimentation which was easily re-suspended on shaking. |
| Assay of sparsentan (% target) | 102, 102 | 103, 101 |
| Related substances (% relative to sparsentan) Individual | | |
| Peak at RRT 0.98 | 0.12 | 0.11 |
| Peak at RRT 1.21 | 0.05 | 0.05 |
| Total | 0.17 | 0.16 |

TABLE 11-continued 14 week stability for Formulation B at 25° C./60% relative humidity and accelerated conditions

| | 14 weeks | |
|---|---|---|
| Test | 25° C./60% RH | 40° C./75% RH |
| Assay of sodium benzoate (% target) | 101, 101 | 101, 100 |
| Viscosity (cP) Spindle 3 at 50 rpm | 499 | 473 |
| pH | 3.2 | 3.2 |
| Microbiological testing (PET) | Complies Ph Eur 5.1.3 | Complies Ph Eur 5.1.3 |

TABLE 12c

Dissolution of the API from suspension at stability time points for Formulation B

| | % sparsentan dissolved (n = 3) at specified time-points | | | | | | | | | | | |
|---|---|---|---|---|---|---|---|---|---|---|---|---|
| | 5 min | | 10 min | | 15 min | | 30 min | | 45 min | | 60 min | |
| | % | x | % | x | % | x | % | x | % | x | % | x |
| Initial | 97 | 99 | 100 | 100 | 101 | 101 | 101 | 101 | 102 | 102 | 102 | 102 |
| | 96 | | 98 | | 99 | | 100 | | 100 | | 100 | |
| | 103 | | 102 | | 102 | | 103 | | 103 | | 103 | |
| 4 weeks at 25° C./ 60% RH | 98 | 98 | 101 | 102 | 102 | 102 | 103 | 103 | 103 | 103 | 103 | 103 |
| | 100 | | 102 | | 103 | | 104 | | 104 | | 104 | |
| | 97 | | 101 | | 102 | | 102 | | 102 | | 102 | |
| 4 weeks at 40° C./ 75% RH | 989 | 98 | 101 | 101 | 102 | 101 | 102 | 102 | 102 | 102 | 102 | 102 |
| | 9 98 | | 101 | | 102 | | 102 | | 102 | | 102 | |
| | | | 100 | | 101 | | 101 | | 101 | | 101 | |
| 14 weeks at 25° C./ 60% RH | 93 | 93 | 98 | 98 | 99 | 99 | 100 | 99 | 100 | 99 | 100 | 99 |
| | 93 | | 98 | | 99 | | 99 | | 99 | | 99 | |
| | 93 | | 97 | | 98 | | 99 | | 99 | | 99 | |
| 14 weeks at 40° C./ 75% RH | 95 | 95 | 101 | 100 | 102 | 101 | 103 | 102 | 103 | 102 | 103 | 102 |
| | 94 | | 100 | | 101 | | 101 | | 101 | | 101 | |
| | 95 | | 100 | | 101 | | 102 | | 102 | | 102 | | x = mean

TABLE 13

Particle size distribution at stability time points for Formulation B

| Time-point/storage condition | D10 (μm) | D50 (μm) | D90 (μm) |
|---|---|---|---|
| Initial | 11.687 | 49.445 | 138.997 |
| 4 weeks at 25° C./60% RH | 13.107 | 50.027 | 138.866 |
| 4 weeks at 40° C./75% RH | 13.205 | 50.647 | 138.482 |
| 14 weeks at 25° C./60% RH | 13.262 | 50.799 | 136.475 |
| 14 weeks at 40° C./75% RH | 13.457 | 52.655 | 137.738 |

Formulation C

Batch size was 3 L. Sodium benzoate was dissolved in 80% of total water quantity. Citric acid was added to achieve pH 3.0±0.2 units. Sucralose and flavor were added stirred until dissolved. Xanthan gum was added with stirring and stirring continued until fully dissolved. Sparsentan was added using homogenization until fully dispersed and a uniform suspension obtained, and the remaining water was added. Formulation C is described in Table 14. Stability data are provided in Tables 15-18. Satisfactory stability was observed for Formulation C, with no significant changes from the initial time-point in appearance or physical or chemical stability after storage for 14 weeks at 25° C./65% RH and 40° C./75% RH. Additionally, after storage for 14 weeks at 40° C./75% RH, Formulation C met the requirements of Ph Eur 5.1.3 for Preservative Efficacy Testing (PET).

TABLE 14

Description of Formulation C

| Ingredient | Quantity (mg/mL) |
|---|---|
| Sparsentan | 20.00 |
| Citric acid | 5.50 |
| Sodium benzoate | 2.30 |
| Xanthan gum | 8.00 |
| Sucralose | 0.75 |
| Lemon Cream flavor PHS459630 | 1.00 |
| Water | 962.45 |
| pH | 3.2 |

TABLE 15

Initial and 4 week stability for Formulation C at 25° C./60% relative humidity and accelerated conditions

| Test | Initial | 4 weeks | |
|---|---|---|---|
| | | 25° C./60% RH | 40° C./75% RH |
| Appearance | White, opaque suspension | White, opaque suspension. Small amount of sedimentation which was easily re-suspended on shaking | White, opaque suspension. Small amount of sedimentation which was easily re-suspended on shaking |
| Assay of sparsentan (% target) | 101, 102, 101, 101, 100 | 103, 102 | 103, 102 |
| Related substances (% relative to sparsentan) Individual | | | |
| Peak at RRT 0.98 | 0.12 | 0.12 | 0.11 |
| Peak at RRT 1.21 | 0.05 | 0.05 | 0.06 |
| Total | 0.17 | 0.17 | 0.17 |
| Assay of sodium benzoate (% target) | 102, 102, 101, 101, 101 | 101, 101 | 101, 101 |
| Viscosity (cP) Spindle 3 at 50 rpm | 1241 | 1212 | 1104 |
| pH | 3.2 | 3.2 | 3.3 |
| Microbiological testing (PET) | | | |

TABLE 16

14 week stability for Formulation C at 25° C./60% relative humidity and accelerated conditions

| Test | 14 weeks | |
|---|---|---|
| | 25° C./60% RH | 40° C./75% RH |
| Appearance | White, opaque suspension. Small amount of sedimentation which was easily re-suspended on shaking. Small amount of API rose to top of suspension was easily re-suspended on shaking. | White, opaque suspension. Large amount of sedimentation which was easily re-suspended on shaking. Small amount of API rose to top of suspension was easily re-suspended on shaking. |
| Assay of sparsentan (% target) | 102, 102 | 101, 102 |
| Related substances (% relative to sparsentan) Individual | | |
| Peak at RRT 0.98 | 0.12 | 0.11 |
| Peak at RRT 1.21 | 0.05 | 0.05 |
| Total | 0.17 | 0.16 |
| Assay of sodium benzoate (% target) | 101, 101 | 100, 99 |
| Viscosity (cP) Spindle 3 at 50 rpm | 1118 | 1078 |
| pH | 3.3 | 3.3 |
| Microbiological testing (PET) | Complies Ph Eur 5.1.3 | Complies Ph Eur 5.1.3 |

TABLE 17

Dissolution of the API from suspension at stability time points for Formulation C

| | % sparsentan dissolved (n = 3) at specified time-points | | | | | | | | | | | |
|---|---|---|---|---|---|---|---|---|---|---|---|---|
| | 5 min | | 10 min | | 15 min | | 30 min | | 45 min | | 60 min | |
| | % | x | % | x | % | x | % | x | % | x | % | x |
| Initial | 94 | 93 | 101 | 101 | 102 | 102 | 103 | 103 | 103 | 103 | 103 | 103 |
| | 94 | | 101 | | 102 | | 103 | | 103 | | 103 | |
| | 92 | | 100 | | 102 | | 104 | | 104 | | 104 | |
| 4 weeks at 25° C./60% RH | 96 | 96 | 101 | 100 | 101 | 102 | 102 | 102 | 102 | 102 | 102 | 102 |
| | 96 | | 99 | | 102 | | 102 | | 102 | | 102 | |
| | 96 | | 101 | | 102 | | 102 | | 103 | | 103 | |
| 4 weeks at 40° C./75% RH | 99 | 100 | 102 | 103 | 103 | 103 | 103 | 103 | 103 | 104 | 103 | 104 |
| | 99 | | 103 | | 103 | | 103 | | 103 | | 103 | |
| | 100 | | 103 | | 103 | | 104 | | 104 | | 104 | |
| 14 weeks at 25° C./60% RH | 97 | 98 | 102 | 103 | 103 | 103 | 103 | 104 | 103 | 104 | 103 | 104 |
| | 98 | | 103 | | 104 | | 104 | | 104 | | 104 | |
| | 100 | | 104 | | 104 | | 104 | | 104 | | 104 | |
| 14 weeks at 40° C./75% RH | 98 | 98 | 103 | 103 | 103 | 103 | 103 | 103 | 103 | 104 | 103 | 103 |
| | 101 | | 104 | | 105 | | 105 | | 105 | | 105 | |
| | 97 | | 101 | | 101 | | 102 | | 102 | | 101 | | x = mean

TABLE 18

Particle size distribution at stability time points for Formulation C

| Time-point/storage condition | D10 (μm) | D50 (μm) | D90 (μm) |
|---|---|---|---|
| Initial | 12.345 | 51.259 | 140.365 |
| 4 weeks at 25° C./60% RH | 11.057 | 45.460 | 120.005 |
| 4 weeks at 40° C./75% RH | 10.655 | 45.914 | 121.115 |
| 14 weeks at 25° C./60% RH | 11.264 | 45.802 | 120.935 |
| 14 weeks at 40° C./75% RH | 10.740 | 46.019 | 119.681 |

Formulation D

Batch size was 3 L. Sodium benzoate was dissolved in 80% of total water quantity. Citric acid was added to achieve pH 3.0±0.2 units. Sucralose and flavor were added stirred until dissolved. Xanthan gum was added with stirring and stirring continued until fully dissolved. Sparsentan was added using homogenization until fully dispersed and a uniform suspension obtained, and the remaining water was added. Formulation D is described in Table 19. Stability data are provided in Table 20. Satisfactory stability was observed for Formulation A, with no significant changes from the initial time-point in appearance or physical or chemical stability after storage for 12 weeks at 25° C./65% RH and 40° C./75% RH. Additionally, after storage for 12 weeks at 40° C./75% RH, Formulation D met the requirements of Ph Eur 5.1.3 for Preservative Efficacy Testing (PET).

TABLE 19

Description of Formulation D

| Ingredient | Quantity (mg/mL) |
|---|---|
| Sparsentan | 20.00 |
| Citric acid | 4.27 |
| Sodium benzoate | 0.50 |
| Xanthan gum | 5.00 |
| Sucralose | 0.75 |
| Strawberry flavor PHS120116 | 1.00 |
| Water | 968.48 |

TABLE 20

Initial and 12 week stability for Formulation D at 25° C./60% relative humidity and accelerated conditions

| | | 12 weeks | |
|---|---|---|---|
| Test | Initial | 25° C./60% RH | 40° C./75% RH |
| Appearance | White, opaque suspension | White, opaque suspension. Large amount of sedimentation which was easily re-suspended on shaking. | White, opaque suspension. Large amount of sedimentation which was easily re-suspended on shaking. |
| Assay of sparsentan (% target) | 100, 100 | 95, 96 | 101, 99 |
| Related substances (% relative to sparsentan) Individual | | | |
| Peak at RRT 0.98 | 0.12 | 0.14, 0.12 | 0.14, 0.13 |
| Peak at RRT 1.23 | ND | <0.05, <0.05 | <0.05, <0.05 |
| Peak at RRT 1.24 | 0.06 | 0.06, <0.05 | 0.05, 0.05 |
| Total | 0.18 | 0.20, 0.12 | 0.19, 0.18 |

TABLE 20-continued

Initial and 12 week stability for Formulation D at 25° C./60% relative humidity and accelerated conditions

| | | 12 weeks | |
|---|---|---|---|
| Test | Initial | 25° C./60% RH | 40° C./75% RH |
| Assay of sodium benzoate (% target) | 101, 101 | 100, 102 | 101, 101 |
| Viscosity (cP) Spindle 3 at 50 rpm | 530 | 422 | 389 |
| pH | 2.9 | 2.9 | 2.9 |
| Microbiological testing (PET) | Complies Ph Eur 5.1.3 | Complies Ph Eur 5.1.3 | Complies Ph Eur 5.1.3 |

All of the U.S. patents, U.S. patent application publications, U.S. patent applications, foreign patents, foreign patent applications, and non-patent publications referred to in this specification or listed in the Application Data Sheet, including U.S. Provisional Patent Application No. 62/741,270, filed Oct. 4, 2018, U.S. Provisional Patent Application No. 62/853,904, filed May 29, 2019, and U.S. Provisional Patent Application No. 62/894,559, filed Aug. 30, 2019, are incorporated herein by reference, in their entirety, unless otherwise stated.

The various embodiments described above can be combined to provide further embodiments. Aspects of the embodiments can be modified, if necessary, to employ concepts of the various patents, applications, and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating hearing loss in a subject having Alport syndrome, in a subject having a mutation in a COL4A3, COL4A4, or COL4A5 gene, comprising administering a pharmaceutical composition comprising a compound having structure (I),

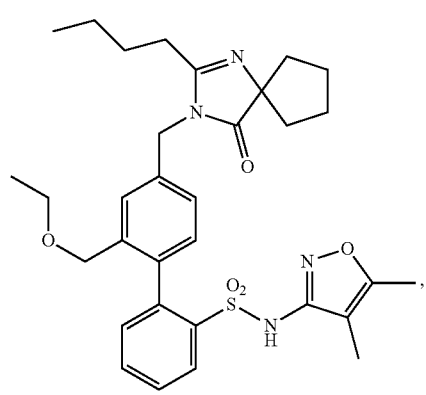

(I)

or a pharmaceutically acceptable salt thereof, to said subject.

2. The method according to claim 1, wherein said mutation is in a COL4A3 gene.

3. The method according to claim 1 wherein said mutation is in a COL4A4 gene.

4. The method according to claim 1, wherein said mutation is in a COL4A5 gene.

5. A method of treating a collagen type IV deficiency in a subject, comprising administering a pharmaceutical composition comprising a compound having structure (I),

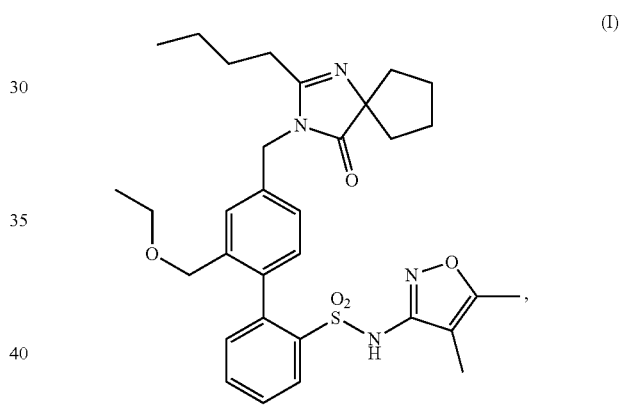

(I)

or a pharmaceutically acceptable salt thereof, to said subject.

6. The method according to claim 5, wherein said subject has Alport syndrome.

7. The method according to claim 1, wherein the amount of said compound having structure (I), or pharmaceutically acceptable salt thereof, administered to said subject is (a) from about 1 mg/kg to about 15 mg/kg; (b) from about 3 mg/kg to about 12 mg/kg; or (c) from about 3 mg/kg to about 6 mg/kg.

8. The method according to claim 1, wherein the amount of said compound having structure (I), or pharmaceutically acceptable salt thereof, administered to said subject is (a) from about 1 mg/kg to about 15 mg/kg per day; (b) from about 3 mg/kg to about 12 mg/kg per day; or (c) from about 3 mg/kg to about 6 mg/kg per day.

9. The method according to claim 1, wherein the amount of said compound having structure (I), or pharmaceutically acceptable salt thereof, administered to said subject is from about 50 mg/day to about 1000 mg/day.

10. The method according to claim 9, wherein the amount of the compound having structure (I), or pharmaceutically acceptable salt thereof, administered to said subject is from about 200 mg/day to about 800 mg/day.

11. The method according to claim 9, wherein the amount of the compound having structure (I), or pharmaceutically acceptable salt thereof, administered to said subject is from about 400 mg/day to about 800 mg/day.

12. The method according to claim 9, wherein the amount of said compound having structure (I), or pharmaceutically acceptable salt thereof, administered to said subject is about 100 mg/day, 200 mg/day, 300 mg/day, 400 mg/day, 500 mg/day, 600 mg/day, 700 mg/day, 800 mg/day, 900 mg/day, or 1000 mg/day.

13. The method according to claim 1, wherein the amount of said compound having structure (I), or pharmaceutically acceptable salt thereof, administered to said subject is about 200 mg/day.

14. The method according to claim 1, wherein the amount of said compound having structure (I), or pharmaceutically acceptable salt thereof, administered to said subject is about 400 mg/day.

15. The method according to claim 1, wherein the amount of said compound having structure (I), or pharmaceutically acceptable salt thereof, administered to said subject is about 800 mg/day.

16. The method according to claim 1, wherein said compound has structure (I).

17. The method according to claim 1, wherein said subject is administered one or more additional therapeutic agents.

18. The method according to claim 1, wherein said subject is an adult.

19. The method according to claim 1, wherein said subject is 18 years old or younger.

20. The method according to claim 19, wherein the pharmaceutical composition is a liquid formulation for oral administration.

21. The method according to claim 19, wherein the amount of said compound having structure (I), or pharmaceutically acceptable salt thereof, administered to said subject is (a) from about 1 mg/kg to about 15 mg/kg; (b) from about 3 mg/kg to about 12 mg/kg; or (c) from about 3 mg/kg to about 6 mg/kg.

22. The method according to claim 19, wherein the amount of said compound having structure (I), or pharmaceutically acceptable salt thereof, administered to said subject is (a) from about 1 mg/kg to about 15 mg/kg per day; (b) from about 3 mg/kg to about 12 mg/kg per day; or (c) from about 3 mg/kg to about 6 mg/kg per day.

* * * * *